US 12,274,716 B2

(12) United States Patent
Hannen et al.

(10) Patent No.: US 12,274,716 B2
(45) Date of Patent: Apr. 15, 2025

(54) PEPTIDES DISPLAYED BY HLA FOR USE IMMUNOTHERAPY AGAINST DIFFERENT TYPES OF CANCERS

(71) Applicant: Immatics Biotechnologies GmbH, Tuebingen (DE)

(72) Inventors: Ricarda Hannen, Tuebingen (DE); Jens Hukelmann, Tuebingen (DE); Florian Koehler, Tuebingen (DE); Daniel Johannes Kowalewski, Tuebingen (DE); Heiko Schuster, Tuebingen (DE); Oliver Schoor, Tuebingen (DE); Michael Roemer, Tuebingen (DE); Chih-Chiang Tsou, Houston, TX (US); Jens Fritsche, Tuebingen (DE)

(73) Assignee: Immatics Biotechnologies GmbH, Tübingen (DE)

( * ) Notice: Subject to any disclaimer, the term of this patent is extended or adjusted under 35 U.S.C. 154(b) by 0 days.

(21) Appl. No.: 18/599,849

(22) Filed: Mar. 8, 2024

(65) Prior Publication Data

US 2024/0366669 A1    Nov. 7, 2024

Related U.S. Application Data

(62) Division of application No. 17/576,866, filed on Jan. 14, 2022, now Pat. No. 11,957,716.

(Continued)

(30) Foreign Application Priority Data

Jan. 15, 2021   (DE) .......................... 102021100809.3

(51) Int. Cl.
*A61K 35/17*   (2015.01)
*A61K 39/00*   (2006.01)
(Continued)

(52) U.S. Cl.
CPC .......... *A61K 35/17* (2013.01); *A61K 39/0011* (2013.01); *A61K 39/4611* (2023.05);
(Continued)

(58) Field of Classification Search
CPC ..... A61K 35/17; A61K 39/0011; A61P 35/00; C07K 14/4748; C12N 5/0636
See application file for complete search history.

(56) References Cited

U.S. PATENT DOCUMENTS 7,807,642 B2   10/2010   Dengjel et al.
7,833,969 B2   11/2010   Dengjel et al.
(Continued)

FOREIGN PATENT DOCUMENTS

EP           1760088 B1      3/2008
WO    WO-2005049642 A2 *   6/2005   ........... C07K 14/195
(Continued)

OTHER PUBLICATIONS

Ankur Dhanik, et al., "In-silico discovery of cancer-specific peptide-HLA complexes for targeted therapy", BMC Bioinformatics, 2016, vol. 17, No. 286.

(Continued)

*Primary Examiner* — Scarlett Y Goon
*Assistant Examiner* — Audrey L Buttice
(74) *Attorney, Agent, or Firm* — McBee, Moore & Vanik IP, LLC

(57) ABSTRACT

The invention relates to a peptide comprising an amino acid sequence selected from the group consisting of (i) SEQ ID NO: 1 to SEQ ID NO: 216, and (ii) a variant sequence thereof which maintains capacity to bind to MHC molecule(s) and/or induce T cells cross-reacting with said variant peptide, or a pharmaceutically acceptable salt thereof.

20 Claims, 27 Drawing Sheets

Specification includes a Sequence Listing.

Related U.S. Application Data

(60) Provisional application No. 63/272,878, filed on Oct. 28, 2021, provisional application No. 63/137,985, filed on Jan. 15, 2021.

(51) Int. Cl.
*A61P 35/00* (2006.01)
*C07K 14/47* (2006.01)
*C12N 5/0783* (2010.01)

(52) U.S. Cl.
CPC .......... *A61K 39/4644* (2023.05); *A61P 35/00* (2018.01); *C07K 14/4748* (2013.01); *C12N 5/0636* (2013.01)

(56) References Cited

U.S. PATENT DOCUMENTS

| | | |
|---|---|---|
| 7,833,970 B2 | 11/2010 | Dengjel et al. |
| 8,084,592 B2 | 12/2011 | Bot et al. |
| 10,196,432 B2 | 2/2019 | Dengjel et al. |
| 10,618,945 B2 | 4/2020 | Dengjel et al. |
| 2008/0044484 A1 | 2/2008 | Minev |
| 2008/0206216 A1 | 8/2008 | Dengjel et al. |
| 2018/0148503 A1 | 5/2018 | Scheinberg et al. |
| 2020/0040057 A1 | 2/2020 | Schuster et al. |
| 2022/0002374 A1 | 1/2022 | Schuster et al. |
| 2022/0211760 A1 | 7/2022 | Kassiotis et al. |

FOREIGN PATENT DOCUMENTS

| | | |
|---|---|---|
| WO | 2007/028574 A2 | 3/2007 |
| WO | 2011050344 A2 | 4/2011 |
| WO | 2011/119484 A1 | 9/2011 |
| WO | 2020/025576 A1 | 2/2020 |
| WO | 2020/131586 A2 | 6/2020 |
| WO | 2021/005339 A1 | 1/2021 |
| WO | 2023039673 A1 | 3/2023 |

OTHER PUBLICATIONS

DE Search Report of DE Application No. 102021100809.3, dated Jun. 10, 2021.
Brossart, Peter and Bevan, Michael J. "Presentation of Exogenous Protein Antigens on Major Histocompatability Complex Class I Molecules by Dendritic Cells: Pathway of Presentation and Regulation by Cytokines" Blood, vol. 90, No. 4, pp. 1594-1599, Aug. 15, 1997.
Dengjel, Joern, et al. "Unexpected Abundance of HLA Class II Presented Peptides in Primary Renal Cell Carcinomas" Clinical Cancer Research, vol. 12, No. 14, pp. 4163-4170, Jul. 15, 2006.
Fritsche, Jens, et al. "Translating Immunopeptidomics to Immunotherapy-Decision-Making for Patient and Personalized Target Selection" Proteomics, vol. 18, No. 12, e1700284, Jun. 2018.
International Search Report and Written Opinion mailed May 12, 2022 in PCT/EP2022/050797 (12 pages).
NCBI Reference Sequence: XP_055915951.1, Database Accession No. BIV41878, "uncharacterized protein LOC129948858 [Eupeodes corollae]" Retrieved on Sep. 5, 2023 from URL: https://www.ncbi.nlm.nih.gov/protein/XP_055915951.1/?report=fasta.
NCBI Reference Sequence: XP_055916174.1, Database Accession No. WO2011119484.368552, "serine-rich adhesin for platelets isoform X1 [Eupeodes corollae]" Retrieved on Sep. 5, 2023 from URL: https://www.ncbi.nlm.nih.gov/protein/XP_055916174.1/?report=fasta.
Rock, K.L., et al. "Presentation of exogenous antigen with class I major histocompatibility complex molecules" Science, vol. 249, No. 4971, pp. 918-921, Aug. 1990.
Singh-Jasuja, Harpreet et al. "The Tuebingen approach: identification, selection, and validation of tumor-associated HLA peptides for cancer therapy" Cancer Immunology, Immunotherapy, vol. 53, pp. 187-185, Jan. 2004.

\* cited by examiner

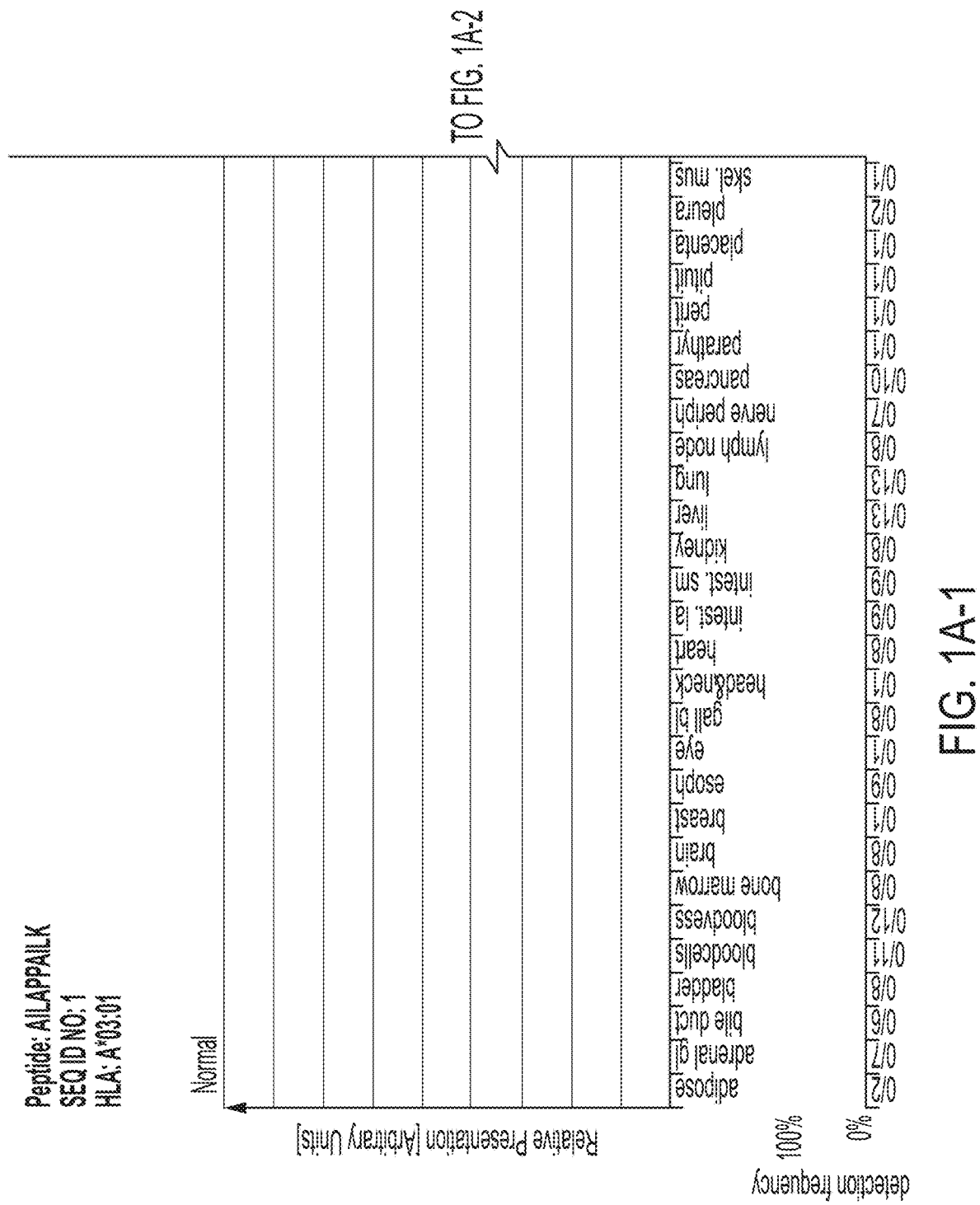

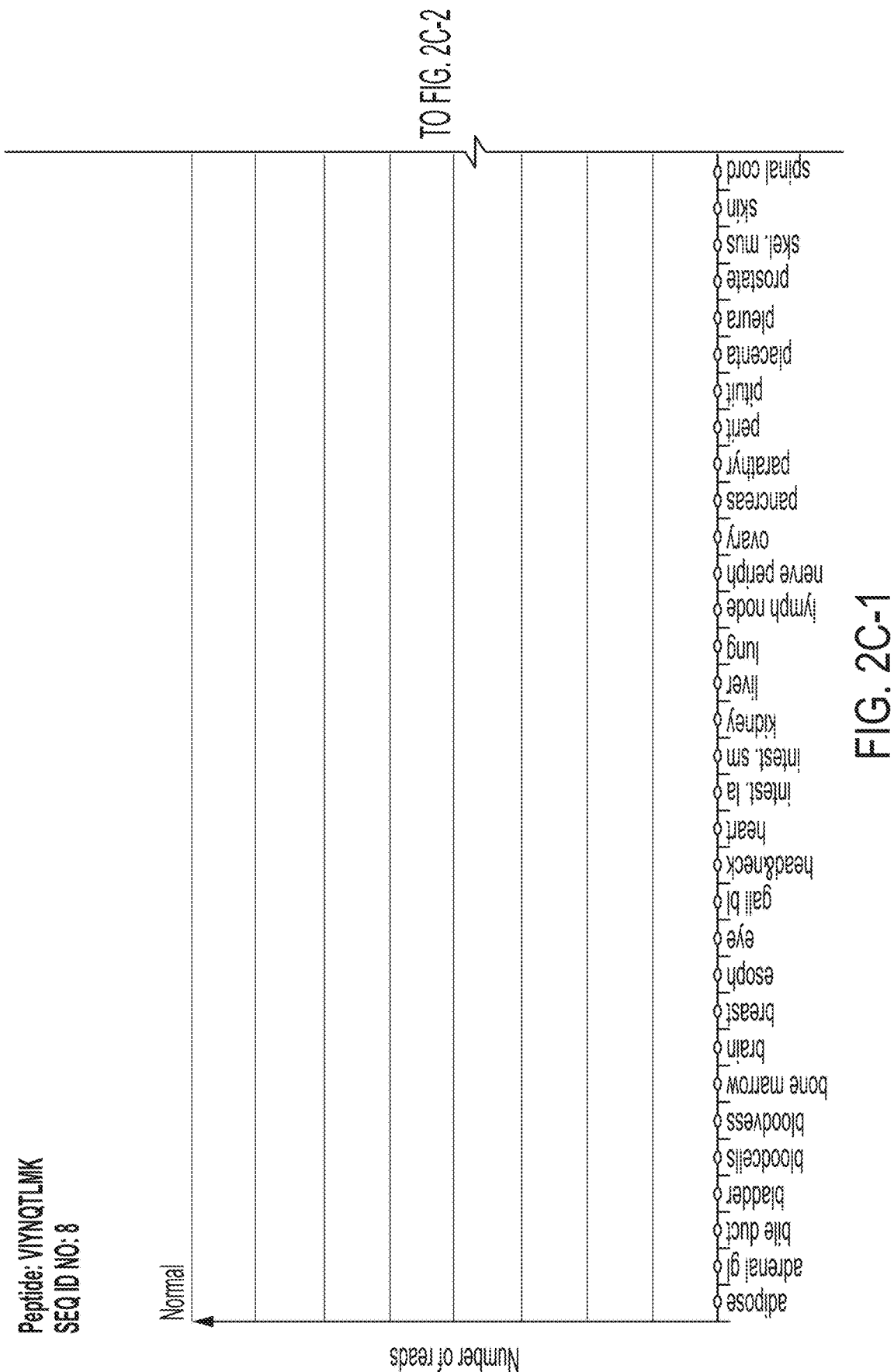

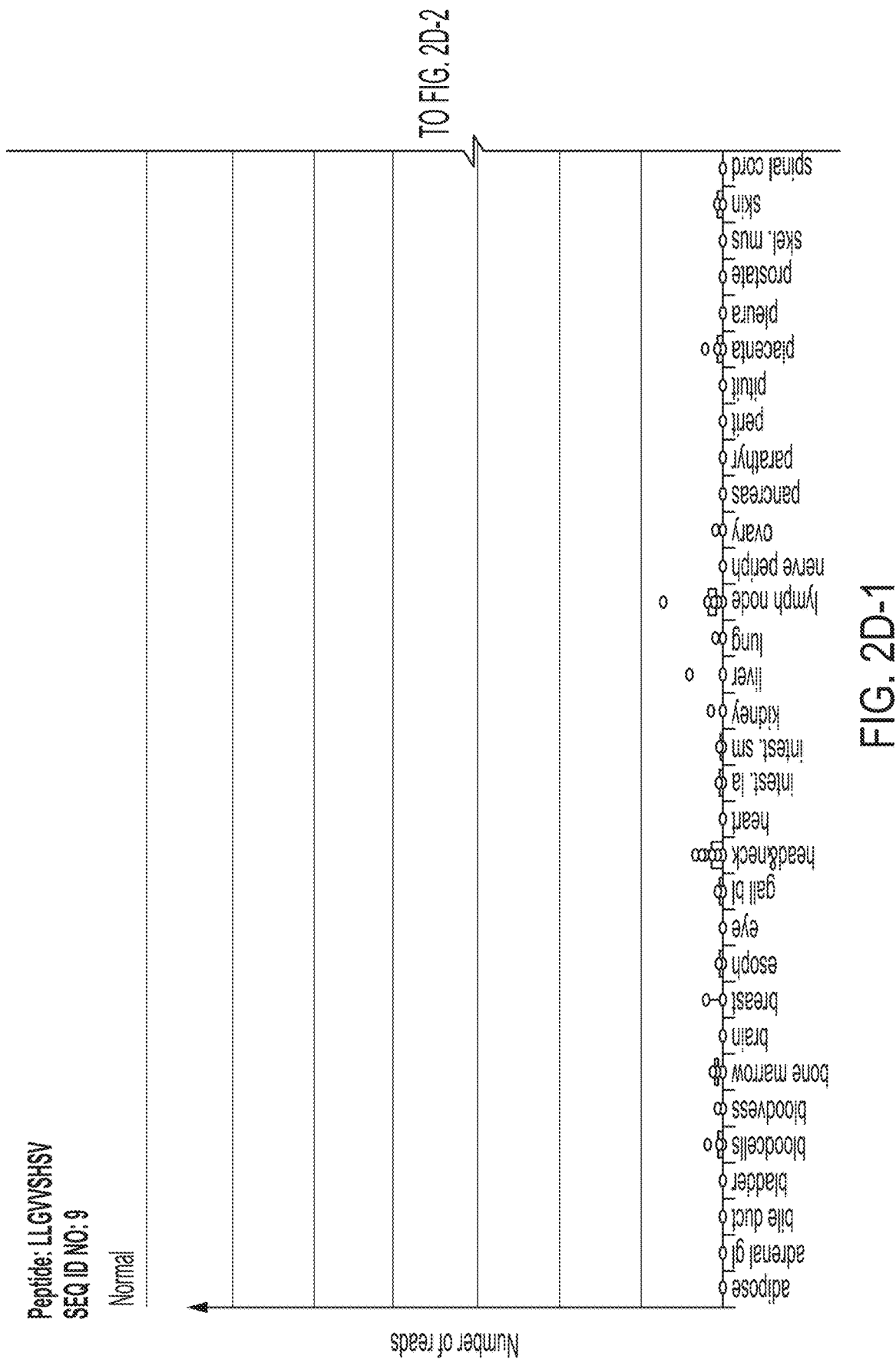

PEPTIDES DISPLAYED BY HLA FOR USE IMMUNOTHERAPY AGAINST DIFFERENT TYPES OF CANCERS

CROSS-REFERENCE TO RELATED APPLICATIONS

The present application is a divisional of, and claims priority to, U.S. patent application Ser. No. 17/576,866, filed Jan. 14, 2022, which claims priority to U.S. Provisional Patent Application No. 63/272,878, filed Oct. 28, 2021, and U.S. Provisional Patent Application No. 63/137,985, filed Jan. 15, 2021. Each of these applications is incorporated by reference in its entirety for all purposes.

REFERENCE TO SEQUENCE LISTING SUBMITTED AS A COMPLIANT XML FILE (.xml)

Pursuant to the EFS-Web legal framework and 37 C.F.R. $1.821-825 (see M.P.E.P. S 2442.03 (a)), a Sequence Listing in the form of a compliant XML file (entitled "2912919-106005_Sequence_Listing_ST26.xml" created on Mar. 7, 2024, and 187,978 bytes in size) is submitted concurrently with the instant application, and the entire contents of the Sequence Listing are incorporated herein by reference.

BACKGROUND OF THE INVENTION

The present invention relates to peptides, proteins, nucleic acids and cells for use in immunotherapeutic methods. In particular, the present invention relates to the immunotherapy of cancer. The present invention furthermore relates to tumor-associated T cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T cell receptors, and other binding molecules.

The present invention relates to several novel peptide sequences and their variants derived from HLA class I molecules of human tumor cells that can be used in vaccine compositions for eliciting anti-tumor immune responses, or as targets for the development of pharmaceutically/immunologically active compounds and cells.

According to the World Health Organization (WHO), cancer ranked among the four major non-communicable deadly diseases worldwide in 2012. For the same year, colorectal cancer, breast cancer and respiratory tract cancers were listed within the top 10 causes of death in high income countries.

Considering the severe side-effects and expense associated with treating cancer, there is a need to identify factors that can be used in the treatment of cancer.

There is also a need to identify factors representing biomarkers for cancer, leading to better diagnosis of cancer, assessment of prognosis, and prediction of treatment success.

Cancer Immunotherapy

Immunotherapy of cancer represents an option of specific targeting of cancer cells while minimizing side effects. Cancer immunotherapy makes use of the existence of tumor associated antigens.

The current classification of tumor associated antigens (TAAs) comprises the following major groups:

a) Cancer-testis antigens: The first TAAs ever identified that can be recognized by T cells belong to this class, which was originally called cancer-testis (CT) antigens. Since the cells of testis do not express class I and II HLA molecules, these antigens cannot be recognized by T cells in normal tissues and can therefore be considered as immunologically tumor specific. Well-known examples for CT antigens are the MAGE family members and NY-ESO-1.

b) Differentiation antigens: These TAAs are shared between tumors and the normal tissue from which the tumor arose. Most of the known differentiation antigens are found in melanomas and normal melanocytes. Examples include, but are not limited to, tyrosinase and Melan-A/MART-1 for melanoma or PSA for prostate cancer.

c) Overexpressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T cell recognition, while their overexpression in tumor cells can trigger an anticancer response by breaking previously established tolerance. Prominent examples for this class of TAAs are Her-2/neu, survivin, telomerase, or WT1.

d) Tumor specific antigens: These unique TAAs arise from mutations of normal genes (such as β-catenin, CDK4, etc.). Some of these molecular changes are associated with neoplastic transformation and/or progression. Tumor specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor specificity (or -association) of a peptide may also arise if the peptide originates from a tumor specific (-associated) exon in case of proteins with tumor specific (-associated) isoforms.

e) Oncoviral proteins: These TAAs are viral proteins that may play a critical role in the oncogenic process and, because they are foreign (not of human origin), they can evoke a T cell response. Examples of such proteins are the human papilloma type 16 virus proteins, E6 and E7, which are expressed in cervical carcinoma.

Human endogenous retroviruses (HERVs) make up a significant portion (~8%) of the human genome. These viral elements integrated into the genome millions of years ago and were since then vertically transmitted through generations. The huge majority of HERVs have lost functional activity through mutation or truncation, yet some endogenous retrovirus, such as the members of the HERV-K clade, still encode functional genes and have been shown to form retrovirus-like particles. Transcription of HERV proviruses is epigenetically controlled and remains silenced under normal physiological conditions. Reactivation and overexpression resulting in active translation of viral proteins has however been described in certain diseases and especially for different types of cancer. This tumor-specific expression of HERV derived proteins can be harnessed for different types of cancer immunotherapy.

f) TAAs arising from abnormal post-translational modifications: Such TAAs may arise from proteins which are neither specific nor overexpressed in tumors but nevertheless become tumor associated by post-translational processes primarily active in tumors. Examples for this class arise from altered glycosylation patterns leading to novel epitopes in tumors as for MUC1 or events like protein splicing during degradation which may or may not be tumor specific.

T cell-based immunotherapy targets peptide epitopes derived from tumor-associated or tumor specific proteins, which are presented by MHC molecules. The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides.

MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation in the literature (Brossart and Bevan, 1997; Rock et al., 1990). MHC class II molecules can be found predominantly on professional antigen presenting cells (APCs), and primarily present peptides of exogenous or transmembrane proteins that are taken up by APCs e.g. during endocytosis and are subsequently processed.

Complexes of peptide and MHC class I are recognized by CD8-positive T cells bearing the appropriate T cell receptor (TCR), whereas complexes of peptide and MHC class II molecules are recognized by CD4-positive helper T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T cell epitopes derived from tumor associated antigens (TAA) is of great importance for the development of pharmaceutical products for triggering anti-tumor immune responses. At the tumor site, T helper cells, support a cytotoxic T cell (CTL) friendly cytokine milieu and attract effector cells, e.g. CTLs, natural killer (NK) cells, macrophages, and granulocytes.

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006).

Elongated (longer) peptides of the invention can act as MHC class II active epitopes.

T helper cells, activated by MHC class II epitopes, play an important role in orchestrating the effector function of CTLs in anti-tumor immunity. T helper cell epitopes that trigger a T helper cell response of the TH1 type support effector functions of CD8-positive killer T cells, which include cytotoxic functions directed against tumor cells displaying tumor-associated peptide-MHC complexes on their cell surfaces. In this way tumor-associated T helper cell peptide epitopes, alone or in combination with other tumor-associated peptides, can serve as active pharmaceutical ingredients of vaccine compositions that stimulate anti-tumor immune responses.

Since the constitutive expression of HLA class II molecules is usually limited to immune cells, the possibility of isolating class II peptides directly from primary tumors was previously not considered possible. However, Dengjel et al. were successful in identifying a number of MHC class II epitopes directly from tumors (WO 2007/028574, EP 1 760 088 B1, the contents of which are herein incorporated by reference in their entirety).

For an MHC class I peptide to trigger (elicit) a cellular immune response, it also must bind to an MHC molecule. This process is dependent on the allele of the MHC molecule and specific polymorphisms of the amino acid sequence of the peptide. MHC class I binding peptides are usually 8-12 amino acid residues in length and usually contain two conserved residues ("anchors") in their sequence that interact with the corresponding binding groove of the MHC molecule. In this way each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T cells bearing specific TCRs.

For proteins to be recognized by T-lymphocytes as tumor specific or associated antigens, and to be used in therapy, particular prerequisites must be fulfilled. The antigen should be expressed mainly by tumor cells and not, or in comparably small amounts, by normal healthy tissues. It may be advantageous that a peptide is over-presented by tumor cells as compared to normal healthy tissues. It is furthermore desirable that the respective antigen is not only present in a type of tumor, but also in high concentrations (i.e., copy numbers of the respective peptide per cell). Tumor specific and tumor-associated antigens are often derived from proteins directly involved in transformation of a normal cell to a tumor cell due to their function, e.g. in cell cycle control or suppression of apoptosis. Additionally, downstream targets of the proteins directly causative for a transformation may be up-regulated und thus may be indirectly tumor-associated. Such indirect tumor-associated antigens may also be targets of a vaccination approach (Singh-Jasuja et al., 2004, the contents of which are herein incorporated by reference in their entirety). It is essential that epitopes are present in the amino acid sequence of the antigen, in order to ensure that such a peptide ("immunogenic peptide"), being derived from a tumor associated antigen, leads to an in vitro or in vivo T cell response.

TAAs may be a starting point for the development of T cell-based immunotherapy. The methods for identifying and characterizing the TAAs are usually based on the use of T cells that can be isolated from patients or healthy subjects, or they are based on the generation of differential transcription profiles or differential peptide expression patterns between tumors and normal tissues. However, the identification of genes overexpressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and the immunological tolerance for this particular epitope needs to be absent or minimal.

In case of targeting peptide-MHC by specific TCRs (e.g. soluble TCRs) and antibodies or other binding molecules (scaffolds) according to the invention, the immunogenicity of the underlying peptides is secondary. In these cases, the presentation is the determining factor.

SUMMARY OF THE INVENTION

In a first aspect, the present invention relates to a peptide comprising an amino acid sequence selected from the group consisting of SEQ ID NO 1 to SEQ ID NO 216, and variant sequences thereof which binds to MHC molecule(s) and/or induces T cells cross-reacting with said variant peptide, or a pharmaceutically acceptable salt thereof.

The following table (Table 1A) shows the peptides according to the present invention and their respective SEQ ID NOS.

TABLE 1A

Peptides according to the invention and their respective SEQ ID NO.

| SEQ ID NO | Sequence |
| --- | --- |
| 1 | AILAPPAILK |
| 2 | GTVFVLLSK |
| 3 | VYIASSFKI |
| 4 | IQAPALLKV |
| 5 | METADRPEW |
| 6 | SHSLPAFTL |
| 7 | IYIPTNSIYKF |
| 8 | VIYNQTLMK |
| 9 | LLGVVSHSV |
| 10 | ILMILQPQL |
| 11 | TEIGTVIKLF |
| 12 | RLQEGLAAL |
| 13 | LYDTVTHTF |
| 14 | ILAPPQRISF |
| 15 | SPVETRSLL |
| 16 | NFHTLAQQLLF |
| 17 | MVNWSLTNK |
| 18 | SLSKLVATV |
| 19 | RILEVVRQPK |
| 20 | ILAPPAILK |
| 21 | MLSAQFILK |
| 22 | RVIEVVMNSK |
| 23 | AETKQFWSA |
| 24 | LIYIPTNSIYK |
| 25 | GVCSTLTIK |
| 26 | ETNTIEFIY |

TABLE 1A-continued

Peptides according to the invention and their respective SEQ ID NO.

| SEQ ID NO | Sequence |
| --- | --- |
| 27 | SQAKQITIW |
| 28 | ATLQAVTLYKK |
| 29 | GTFIAPVMK |
| 30 | SLKSSILFL |
| 31 | VFLLLPYPRF |
| 32 | TAMTTLMAF |
| 33 | AYIPFPPLI |
| 34 | LLFKGLMWK |
| 35 | SLATAISAK |
| 36 | KEIEAQEAA |
| 37 | RLYSGSSFLY |
| 38 | AVVSHFILY |
| 39 | RELGVGIAL |
| 40 | LYQTTIELF |
| 41 | APQPRSLAA |
| 42 | LLSRGILIL |
| 43 | VFIPSVINL |
| 44 | SLFPYFLNK |
| 45 | SLFPISLTV |
| 46 | GESIYLLVRKW |
| 47 | LYIFTTRPF |
| 48 | TEMSVSALY |
| 49 | IYFHLNNWTI |
| 50 | KTIDLVIVR |
| 51 | SVFSLVHLFDK |
| 52 | SPLPHLGPL |
| 53 | TTLENLPQK |
| 54 | ASSPVILLL |
| 55 | SPVSASWIL |
| 56 | DVDIHKDLY |
| 57 | IIIDRILLL |
| 58 | REQLDGATL |
| 59 | AVDLGVLEL |
| 60 | VSPDEVLALW |
| 61 | GLIAFAIFK |
| 62 | SFSLLLPYL |
| 63 | MPANFETIGF |
| 64 | LPTRSLPAF |

TABLE 1A-continued

Peptides according to the invention and their respective SEQ ID NO.

| SEQ ID NO | Sequence |
|---|---|
| 65 | NSDLFYLLL |
| 66 | RPLILIRI |
| 67 | GRFWLPFNF |
| 68 | TVDKGELLY |
| 69 | KYPTIICGF |
| 70 | LIAGLIFLK |
| 71 | LIDSLLLLL |
| 72 | GSCSFALSR |
| 73 | NQKGLISL |
| 74 | TLNVLITL |
| 75 | TTAAVYILK |
| 76 | VQSGVPSRF |
| 77 | YPDVPIGQL |
| 78 | TPSHSTPSF |
| 79 | SLFRLSISF |
| 80 | IFDLSDPRF |
| 81 | KLIAGLIFLK |
| 82 | VLQSLQHEL |
| 83 | EAAPNIMHY |
| 84 | KEFAFLEHSL |
| 85 | LPHPVNSGL |
| 86 | VANDRLSFL |
| 87 | LHLNPGLSF |
| 88 | KVGAVVHLK |
| 89 | SPSSPLLLLA |
| 90 | LALLGAPPPK |
| 91 | RIVTYIVAK |
| 92 | LNFSDVFLY |
| 93 | SPIGLSLIL |
| 94 | AVFLGNPSNQK |
| 95 | YAFRNQTL |
| 96 | HPRESLNMLVAF |
| 97 | ALIVLHLSL |
| 98 | FSEIFQDFL |
| 99 | RADEEQASF |
| 100 | SPAPSLARFLSL |
| 101 | ATNSFLLIK |

TABLE 1A-continued

Peptides according to the invention and their respective SEQ ID NO.

| SEQ ID NO | Sequence |
|---|---|
| 102 | FLLLEKGGEL |
| 103 | RPWLSSPTGL |
| 104 | GSLQTLPPK |
| 105 | LVFESVVAA |
| 106 | GLLDAFLRL |
| 107 | SVISVLTTPK |
| 108 | SLQESLPNA |
| 109 | MPKLFLTAC |
| 110 | APSLARFLSL |
| 111 | RPIWDVRSA |
| 112 | ETYGTFVLR |
| 113 | ALGPMAFRV |
| 114 | VPHHLLSSV |
| 115 | LWEEKPVCL |
| 116 | IYLTKSNLVNM |
| 117 | GEAAAARPV |
| 118 | RLLRLIPIL |
| 119 | VLHGLLFTL |
| 120 | APGPRSQGL |
| 121 | ILVTAWKGV |
| 122 | FTQKINSTW |
| 123 | TYLESSVRI |
| 124 | SPSSNSREL |
| 125 | ALAQGANLK |
| 126 | NPELLVILL |
| 127 | TVATQVATSK |
| 128 | MTFVPLLAR |
| 129 | IPISIFKMA |
| 130 | ITPDSIPSV |
| 131 | TILAKQNVL |
| 132 | LYLETRSEF |
| 133 | KFPPSASEF |
| 134 | MPCTTILRI |
| 135 | SADTAELLL |
| 136 | YSSEIWDLY |
| 137 | MPIQVLKGL |
| 138 | RTLPLEGSPK |
| 139 | EEGRIITKW |

TABLE 1A-continued

Peptides according to the invention and their respective SEQ ID NO.

| SEQ ID NO | Sequence |
|---|---|
| 140 | QPAPQPLL |
| 141 | REVAGASAL |
| 142 | YMLEMDNSMKI |
| 143 | AVLGALLRH |
| 144 | IIVPSFYK |
| 145 | HLFSVLSAI |
| 146 | KVLVDFLLK |
| 147 | VEAPHLPSF |
| 148 | SVYMATTLK |
| 149 | SMNSKALRWK |
| 150 | IVFLLQQGEK |
| 151 | AVFVNWEQTKK |
| 152 | KIMEILNLK |
| 153 | ALNLSRLTV |
| 154 | TVTSAIVNR |
| 155 | MPWVLMSPF |
| 156 | SLRVPSPAL |
| 157 | APLRAGWAA |
| 158 | FQLSGPVTF |
| 159 | ASAIPAGAK |
| 160 | EYLGSENVF |
| 161 | ILAASFQAR |
| 162 | LPVHGPLPLLL |
| 163 | LWALAIPSL |
| 164 | SHSSPTVSF |
| 165 | FYNPRPPLI |
| 166 | VIFLHQPPK |
| 167 | FALGPIIKQL |
| 168 | AEGPDHHSL |
| 169 | RPQGVGPAA |
| 170 | LLDSWNILI |
| 171 | NVSFEVSLLY |
| 172 | LLYKTLIIL |
| 173 | IFTGRNAYF |
| 174 | LSGPVTFLR |
| 175 | MPFLKVPPL |
| 176 | AFLLSLISL |
| 177 | SYLKDHLSL |
| 178 | SLFGGLFTR |
| 179 | MIFSGVFLR |
| 180 | QYLTYYPSF |
| 181 | FDLNIGSAY |
| 182 | RPSLPCRSF |
| 183 | VFVISGSHLF |
| 184 | VVHGGMSIF |
| 185 | MPAFLSRASAL |
| 186 | SQIKSPVVF |
| 187 | RLCPAAPTGK |
| 188 | KLPFFTNFL |
| 189 | IWRALGSLF |
| 190 | STQSSLLYLK |
| 191 | APLLPGPAA |
| 192 | IPLHFSTAF |
| 193 | ILQLITVNR |
| 194 | VLYPSHSSF |
| 195 | AWNESSAWLL |
| 196 | NSENLLVY |
| 197 | HHTQLVFVF |
| 198 | MTYQQPFSNR |
| 199 | RAPLPLLLL |
| 200 | GLLGTLRVL |
| 201 | VWILQKVNLAF |
| 202 | KLLLLSSVK |
| 203 | AILVPQPPK |
| 204 | VVRASSGLK |
| 205 | SLIPIVPFKS |
| 206 | VEGVHFVQLL |
| 207 | LPALLRSL |
| 208 | YVGPTRLEL |
| 209 | AILLPQLPK |
| 210 | ASRIQVILL |
| 211 | VVTIVMHIYK |
| 212 | WETRLHNLW |
| 213 | TLLSFKTVLFK |
| 214 | RPSPVRVAAL |

TABLE 1A-continued

Peptides according to the invention and their respective SEQ ID NO.

| SEQ ID NO | Sequence |
| --- | --- |
| 215 | TPLTRTTL |
| 216 | ILRTVLPSL |

TABLE 1B

Peptides according to the invention.

| SEQ ID NO | SEQUENCE |
| --- | --- |
| 217 | ELAGIGILTV |
| 218 | YLLPAIVHI |

The present invention furthermore generally relates to the peptides according to the present invention for use in the treatment of proliferative diseases. Proliferative diseases in the context are, for example, acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer.

Particularly preferred are the peptides—alone or in combination—according to the present invention selected from the group consisting of SEQ ID NO: 1 to SEQ ID NO: 216.

Thus, another aspect of the present invention relates to the use of the peptides according to the present invention for the—preferably combined—treatment of a proliferative disease.

The present invention furthermore relates to peptides according to the present invention that have the ability to bind to an MHC molecule class I or in an elongated form, such as a length-variant-MHC class II.

The present invention further relates to elongated peptides, which after administration (e.g. as vaccine) can be processed intracellularly, leading to shorter peptides consisting or consisting essentially of the amino acid sequences according to SEQ ID NO: 1 to SEQ ID NO: 216 which is then presented by HLA on the cell surface.

The present invention further relates to the peptides according to the present invention wherein said peptides (each) consist or consist essentially of an amino acid sequence according to SEQ ID NO: 1 to SEQ ID NO: 216.

The present invention further relates to the peptides according to the present invention, wherein said peptide includes non-peptide bonds.

The present invention further relates to the peptides according to the present invention, wherein said peptide is part of a fusion protein, in particular fused to the N-terminal amino acids of the HLA-DR antigen-associated invariant chain (Ii) or fused to (or into the sequence of) an antibody, such as, for example, an antibody that is specific for dendritic cells.

The present invention further relates to nucleic acids, encoding the peptides according to the present invention.

The present invention further relates to the nucleic acid according to the present invention, that is DNA, cDNA, PNA, RNA or combinations thereof.

The present invention further relates to an expression vector capable of expressing and/or expressing a nucleic acid according to the present invention.

The present invention further relates to a peptide according to the present invention, a nucleic acid according to the present invention or an expression vector according to the present invention for use in the treatment of diseases and in medicine, in particular in the treatment of cancer.

The present invention further relates to antibodies that are specific against the peptides according to the present invention or complexes of said peptides according to the present invention with MHC, and methods of making these.

The present disclosure may also relate to methods of producing an antibody specifically binding to an MHC class I molecule complexed with an peptide comprising, consisting of, or consisting essentially of an amino acid sequence according to SEQ ID NO: 1 to SEQ ID NO: 216, including immunizing genetically engineered non-human mammal containing cells expressing said MHC class I molecule with a soluble form of an MHC class I molecule complexed with a peptide consisting or consisting essentially of an amino acid sequence according to SEQ ID NO: 1 to SEQ ID NO: 216; isolating mRNA molecules from antibody producing cells of said non-human mammal; producing a phage display library displaying protein molecules encoded by said mRNA molecules; and isolating at least one phage from said phage display library, wherein said at least one phage displays said antibody specifically binding to said MHC class I molecule complexed with a peptide comprising, consisting of, or consisting essentially of an amino acid sequence according to SEQ ID NO: 1 to SEQ ID NO: 216. In another aspect, the antibody may be a monoclonal antibody.

In an aspect, the antibody may bind to said MHC class I molecule complexed with an antigen comprising, consisting of, or consisting essentially of an amino acid sequence according to SEQ ID NO: 1 to SEQ ID NO: 216 with a binding affinity ($K_d$) of <100 nM, more preferably <50 nM, more preferably <10 nM, more preferably <1 nM, more preferably <0.1 nM, more preferably <0.01 nM.

In another aspect, methods of producing an antibody may further include humanizing the antibody. In aspects, methods of producing an antibody may further include conjugating the antibody with a toxin. In another aspect, methods of producing an antibody may further include conjugating the antibody with an immune stimulating domain.

In an aspect, methods of producing an antibody may further include modifying the antibody in the form of a bispecific antibody. In another aspect, methods of producing an antibody may further include modifying the antibody in the form of a chimeric antibody. In another aspect, methods of producing an antibody may further include modifying the antibody in the form of an Fv. In an aspect, methods of producing an antibody may further include modifying the antibody in the form of a Fab. In another aspect, methods of producing an antibody may further include modifying the antibody in the form of a Fab'. In another aspect, methods of producing an antibody may further include labeling the antibody with a radionucleotide, which may be selected from the group consisting of $^{111}$In, $^{99}$Tc, $^{14}$C, $^{131}$I, $^{3}$H, $^{32}$P, and $^{35}$S. In another aspect, the non-human mammal may be a mouse.

The present invention further relates to TCRs, in particular soluble TCRs and cloned TCRs engineered into autologous or allogeneic T cells, and methods of making these, as well as NK cells or other cells bearing said TCR or cross-reacting with said TCRs. The soluble TCR may have a binding affinity ($K_d$)<100 nM, more preferably <50 nM, more preferably <10 nM, more preferably <1 nM, more preferably <0.1 nM, more preferably <0.01 nM. Whereas the cloned cell based TCR may have a binding affinity ($K_d$)<50 UM, more preferably <25 µM, more preferably <10 UM, more preferably <1 µM, more preferably <0.1 µM.

The antibodies and TCRs are additional embodiments of the immunotherapeutic use of the peptides according to the invention at hand.

The present invention further relates to a host cell comprising a nucleic acid according to the present invention or an expression vector as described before. The present invention further relates to the host cell according to the present invention that is an antigen presenting cell, and preferably is a dendritic cell.

The present invention further relates to said method according to the present invention, wherein the antigen is loaded onto class I or II MHC molecules expressed on the surface of a suitable antigen-presenting cell or artificial antigen-presenting cell by contacting a sufficient amount of the antigen with an antigen-presenting cell.

The present invention further relates to the method according to the present invention, wherein the antigen-presenting cell comprises an expression vector capable of expressing said peptide containing SEQ ID NO: 1 to SEQ ID NO: 216.

The present invention further relates to activated T cells, produced by the method according to the present invention, wherein said T cell selectively recognizes a cell which expresses a polypeptide comprising an amino acid sequence according to the present invention.

The present invention further relates to a method of killing target cells in a patient whose target cells aberrantly express a polypeptide comprising any amino acid sequence according to the present invention, the method comprises administering an effective number of T cells to the patient as produced according to the present invention.

The present invention further relates to the use of any peptide as described, the nucleic acid according to the present invention, the expression vector according to the present invention, the cell according to the present invention, the activated T lymphocyte, the TCR or the antibody or other peptide and/or peptide-MHC binding molecules according to the present invention as a medicament or in the manufacture of a medicament. Preferably, said medicament is active against cancer. Preferably, said medicament is a cellular therapy, a vaccine or a protein based on a soluble TCR or antibody.

The present invention further relates to a use according to the present invention, wherein said cancers are acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer, and preferably acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer cells.

The present invention further relates to biomarkers based on the peptides according to the present invention, herein called "targets" that can be used in the diagnosis of cancer, preferably acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer. The marker can be over-presentation of the peptide(s) themselves, or overexpression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC.

Optionally, the antibody carries a further effector function such as an immune stimulating domain or toxin.

The present invention also relates to the use of these novel targets in the context of cancer treatment.

Provided are also one or more elongated peptides, which after administration (e.g. as vaccine) can be processed intracellularly, leading to shorter peptides consisting or consisting essentially of the amino acid sequences according to SEQ ID NO: 1 to SEQ ID NO: 216 which is then presented by HLA on the cell surface.

In some embodiments a peptide as disclosed herein is provided as a chemically synthesized peptide. The peptide may for example have been synthesized by means of solid phase synthesis.

In some embodiments a peptide as disclosed herein is provided as a recombinant peptide. The peptide may for example have been secreted by a recombinant host cell expressing the peptide. In such embodiments the peptide may have been isolated from the media encompassing the cells. In such embodiments the cells can be sedimented, and the supernatant be collected for isolating the peptide. The peptide may in some embodiments have been expressed in a recombinant host cell without being secreted. In such embodiments the peptide may have been isolated from the cells.

DETAILED DESCRIPTION OF THE INVENTION

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T cells from tumor-infiltrating cell populations or from peripheral blood suggests that such cells play an important role in natural immune defense against cancer. CD8-positive T cells in particular, which recognize MHC class I molecules bearing peptides of usually 8 to 12 amino acid residues derived from proteins or defect ribosomal products (DRIPS) located in the cytosol, play an important role in this response. The MHC molecules of the human are also designated as human leukocyte-antigens (HLA).

As used herein and except as noted otherwise all terms are defined as given below.

The term "T cell response" means the specific proliferation and activation of effector functions induced by a peptide in vitro or in vivo. For MHC class I restricted cytotoxic T cells, effector functions may be lysis of peptide pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carboxyl groups of the adjacent amino acids.

Furthermore, the term "peptide" shall include salts of a series of amino acid residues, connected one to the other typically by peptide bonds between the alpha-amino and carboxyl groups of the adjacent amino acids. Preferably, the salts are pharmaceutically acceptable salts of the peptides, such as, for example, the chloride or acetate (trifluoroacetate) salts. It has to be noted that the salts of the peptides according to the present invention differ substantially from the peptides in their state(s) in vivo, as the peptides are not in the form of salts or associated with counterions in vivo.

The term "peptide" shall also include "oligopeptide". The term "oligopeptide" is used herein to designate a series of amino acid residues, connected one to the other typically by peptide bonds between the alpha-amino and carboxyl groups of the adjacent amino acids. The length of the oligopeptide is not critical to the invention, as long as the correct epitope or epitopes are maintained therein.

The term "polypeptide" designates a series of amino acid residues, connected one to the other typically by peptide bonds between the alpha-amino and carboxyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T cell response. Thus, an "immunogen" would be a molecule that is capable of inducing an immune response, and in the case of the present invention, a molecule capable of inducing a T cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC molecule, forming a ternary complex (MHC class I alpha chain, beta-2-microglobulin, and peptide) that can be recognized by a T cell bearing a matching T cell receptor binding to the MHC-peptide complex with appropriate affinity. Peptides binding to MHC class I molecules are typically 8-12 amino acids in length, and most typically 9 amino acids in length.

The peptides of the invention, preferably when included into a vaccine of the invention as described herein bind to at least one selected from the group consisting of HLA-A*01:01, HLA-A*02:01, HLA-A*03:01, HLA-A*24:02, HLA-B*07:02, HLA-B*08:01 and HLA-B*44:02, plus optionally other HLA allotypes. Due to similarities in binding pattern such as the relevant anchoring positions some peptides bind to more than one allele, such an overlap is most likely, but not limited to, HLA-A*01 binding peptides also binding to HLA-B*15, HLA-A*03 binding peptides also binding to HLA-A*11, HLA-B*07 binding peptides also binding to HLA-B*35 and HLA-B*51.

A vaccine may also include pan-binding MHC class II peptides. Therefore, the vaccine of the invention can be used to treat cancer in patients that are positive for the respective HLA, whereas no selection for MHC class II allotypes is necessary due to the pan-binding nature of these peptides.

If peptides of the invention are combined with peptides binding to another allele, a higher percentage of any patient population can be treated compared with addressing either MHC class I allele alone. For example, with the combination of an HLA-A*02:01 binding peptide with an HLA-A*24:02 binding peptide 60% of patients in any relevant population can be treated, whereas in most populations less than 50% of patients could be addressed by either allele alone.

In a preferred embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in a substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —$NH_2$ group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like. In a preferred embodiment, the pharmaceutical compositions comprise the peptides as salts of acetic acid (acetates), trifluor acetates or hydrochloric acid (chlorides).

The term "promoter" means a region of DNA involved in binding of RNA polymerase to initiate transcription.

The term "isolated" means that the material is removed from its original environment (e.g., the natural environment, if it is naturally occurring). For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity, rather it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptides expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in an enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, mouse, rat, llama, sheep, goat, dog, or horse, and also including a human, such immune response taking the form of stimulating a T cell response within the recipient animal, such as a human. Alternatively, the "active fragment" may also be used to induce a T cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any endonucleases.

In accordance with the present invention, the term "percent identity" or "percent identical", when referring to a sequence, means that a sequence is compared to a claimed or described sequence after alignment of the sequence to be compared (the "compared sequence") with the described or claimed sequence (the "reference sequence"). The percent identity is then determined according to the following formula:

$$\text{percent identity} = 100[1-(C/R)]$$

wherein C is the number of differences between the reference sequence and the compared sequence over the length of alignment between the reference sequence and the compared sequence, wherein
(i) each base or amino acid in the reference sequence that does not have a corresponding aligned base or amino acid in the compared sequence and
(ii) each gap in the reference sequence and
(iii) each aligned base or amino acid in the reference sequence that is different from an aligned base or amino acid in the compared sequence, constitutes a difference and
(iiii) the alignment has to start at position 1 of the aligned sequences;
and R is the number of bases or amino acids in the reference sequence over the length of the alignment with the compared sequence with any gap created in the reference sequence also being counted as a base or amino acid.

If an alignment exists between the compared sequence and the reference sequence for which the percent identity as calculated above is about equal to or greater than a specified minimum percent identity then the compared sequence has the specified minimum percent identity to the reference sequence even though alignments may exist in which the herein above calculated percent identity is less than the specified percent identity.

As mentioned above, the present invention thus provides a peptide comprising a sequence that is selected from the group consisting of SEQ ID NO: 1 to SEQ ID NO: 216 or a variant thereof that will induce T cells cross-reacting with said peptide. The peptides of the invention have the ability to bind to an MHC molecule class I or elongated versions of said peptides to class II.

In the present invention, the term "homologous" refers to the degree of identity (see percent identity above) between sequences of two amino acid sequences, i.e., peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess whether T cells induced by a variant of a specific peptide will be able to cross-react with the peptide itself (see, for example, Appay et al., 2006; Colombetti et al., 2006; Fong et al., 2001; Zaremba et al., 1997, the contents which are incorporated by reference in their entireties).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in SEQ ID NO: 1 to SEQ ID NO: 216. For example, a peptide may be modified so that it at least maintains, if not improves, the ability to interact with and bind to the binding groove of a suitable MHC molecule, and in that way, it at least maintains, if not improves, the ability to bind to the TCR of activated T cells.

These T cells can subsequently cross-react with cells and kill cells that express a polypeptide that contains the natural amino acid sequence of the cognate peptide as defined in the aspects of the invention. As can be derived from scientific literature and databases (Rammensee et al., 1999; Godkin et al., 1997, which are incorporated by reference in their entireties), certain positions of HLA binding peptides are typically anchor residues forming a core sequence fitting to the binding motif of the HLA molecule, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO: 216, by maintaining the known anchor residues, and would be able to determine whether such variants maintain the ability to bind MHC class I or II molecules. The variants of the present invention retain the ability to bind to the TCR of activated T cells, which can subsequently cross-react with and kill cells that express a polypeptide containing the natural amino acid sequence of the cognate peptide as defined in the aspects of the invention.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these often show similarities in size, charge, polarity, and hydrophobicity between the original amino acid and its replacement, and such is the basis for defining "conservative substitutions".

Conservative substitutions are herein defined as exchanges within one of the following five groups: Group 1—small aliphatic, nonpolar or slightly polar residues (Ala, Ser, Thr, Pro, Gly); Group 2—polar, negatively charged residues and their amides (Asp, Asn, Glu, Gln); Group 3—polar, positively charged residues (His, Arg, Lys); Group 4—large, aliphatic, nonpolar residues (Met, Leu, Ile, Val, Cys); and Group 5—large, aromatic residues (Phe, Tyr, Trp).

In an aspect, conservative substitutions may include those, which are described by Dayhoff in "The Atlas of Protein Sequence and Structure. Vol. 5", Natl. Biomedical Research, the contents of which are incorporated by reference in their entirety. For example, in an aspect, amino acids, which belong to one of the following groups, can be exchanged for one another, thus, constituting a conservative exchange: Group 1: alanine (A), proline (P), glycine (G), asparagine (N), serine(S), threonine (T); Group 2: cysteine (C), serine(S), tyrosine (Y), threonine (T); Group 3: valine (V), isoleucine (I), leucine (L), methionine (M), alanine (A), phenylalanine (F); Group 4: lysine (K), arginine (R), histidine (H); Group 5: phenylalanine (F), tyrosine (Y), tryptophan (W), histidine (H); and Group 6: aspartic acid (D), glutamic acid (E). In an aspect, a conservative amino acid substitution may be selected from the following of T→A, G→A, A→I, T→V, A→M, T→I, A→V, T→G, and/or T→S.

In an aspect, a conservative amino acid substitution may include the substitution of an amino acid by another amino acid of the same class, for example, (1) nonpolar: Ala, Val, Leu, Ile, Pro, Met, Phe, Trp; (2) uncharged polar: Gly, Ser, Thr, Cys, Tyr, Asn, Gln; (3) acidic: Asp, Glu; and (4) basic: Lys, Arg, His. Other conservative amino acid substitutions may also be made as follows: (1) aromatic: Phe, Tyr, His; (2) proton donor: Asn, Gln, Lys, Arg, His, Trp; and (3) proton acceptor: Glu, Asp, Thr, Ser, Tyr, Asn, Gln (see, for example, U.S. Pat. No. 10,106,805, the contents of which are incorporated by reference in their entirety).

In another aspect, conservative substitutions may be made in accordance with table 2. Methods for predicting tolerance to protein modification may be found in literature (for example, Guo et al., 2004 the contents of which are incorporated by reference in their entirety).

TABLE 2

| List of conservative amino acid substitutions. | |
| --- | --- |
| Original residue | Conservative substitutions (others are known in the art) |
| Ala | Ser, Gly, Cys |
| Arg | Lys, Gln, His |

TABLE 2-continued

List of conservative amino acid substitutions.

| Original residue | Conservative substitutions (others are known in the art) |
|---|---|
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |
| Ser | Thr, Cys, Ala |
| Thr | Ser, Val, Ala |
| Trp | Tyr, Phe |
| Tyr | Trp, Phe, His |
| Val | Ile, Leu, Met, Ala, Thr |

In another aspect, substitutions may be those shown in table 3. If such substitutions result in a change in biological activity, then more substantial changes, denominated "exemplary substitutions" in table 3, may be introduced and the products screened if needed.

TABLE 3

Exemplary amino acid substitutions.

| Original residue | Exemplary substitutions (other are known in the art) |
|---|---|
| Ala | Val, Leu, Ile |
| Arg | Lys, Gln, Asn |
| Asn | Gln, His, Asp, Lys, Arg |
| Asp | Glu, Asn |
| Cys | Ser, Ala |
| Gln | Asn, Glu |
| Glu | Asp, Gln |
| Gly | Ala |
| His | Asn, Gln, Lys, Arg |
| Ile | Leu, Val, Met, Ala, Phe, Norleucin |
| Leu | Norleucin, Ile, Val, Met, Ala, Phe |
| Lys | Arg, Gln, Asn |
| Met | Leu, Phe, Ile |
| Phe | Leu, Val, Ile, Ala, Tyr |
| Pro | Ala |
| Ser | Thr |
| Thr | Ser, Ala |
| Trp | Tyr, Phe |
| Tyr | Trp, Phe, Thr, Ser |
| Val | Ile, Leu, Met, Phe, Ala, Norleucin |

Of course, such substitutions may involve structures other than the common L-amino acids. Thus, D-amino acids might be substituted for the L-amino acids commonly found in the antigenic peptides of the invention and yet still be encompassed by the disclosure herein. In addition, non-standard amino acids (i.e., other than the common naturally occurring proteinogenic amino acids) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide.

A peptide consisting essentially of the amino acid sequence as indicated herein can have one or two non-anchor amino acids (see below regarding the anchor motif) exchanged without its ability to bind to an MHC molecule class I or II being substantially changed or negatively affected, when compared to the non-modified peptide. In another embodiment, in a peptide consisting essentially of the amino acid sequence as indicated herein, one or two amino acids can be exchanged with their conservative exchange partners (see herein below) without the ability to bind to an MHC molecule class I or II being substantially changed, or is negatively affected, when compared to the non-modified peptide.

The amino acid residues that do not substantially contribute to interactions with the T cell receptor can be modified by replacement with other amino acids whose incorporation does not substantially affect T cell reactivity and does not eliminate binding to the relevant MHC. Thus, apart from the proviso given, the peptide of the invention may be any peptide (by which term the inventors include oligopeptide or polypeptide), which includes the amino acid sequences, or a portion or variant thereof as given.

Longer (elongated) peptides may also be suitable. It is possible that MHC class I epitopes, although usually between 8 and 12 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

The peptides of the invention can be elongated by up to four amino acids, that is 1, 2, 3 or 4 amino acids can be added to either end in any combination between 4:0 and 0:4. Combinations of the elongations according to the invention can be found in table 4.

TABLE 4

Combinations of the elongations of peptides of the invention

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

| N-terminus | C-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present invention may be identical to naturally occurring tumor-associated or tumor specific epitopes or may include epitopes that differ by no more than four residues from the reference peptide, as long as they have substantially identical antigenic activity.

In an alternative embodiment, the peptide is elongated on either or both sides by more than 4 amino acids, preferably to a total length of up to 30 amino acids. This may lead to MHC class II binding peptides. Binding to MHC class II can be tested by methods known in the art.

Accordingly, the present invention provides peptides and variants of MHC class I epitopes, wherein the peptide or variant has an overall length of between 8 and 100, preferably between 8 and 30, and most preferred between 8 and 12, namely 8, 9, 10, 11, 12 amino acids, in case of the elongated class II binding peptides the length can also be 13, 14, 15, 16, 17, 18, 19, 20, 21 or 22 amino acids.

Of course, the peptide or variant according to the present invention will have the ability to bind to an MHC molecule class I or II. Binding of a peptide or a variant to an MHC complex may be tested by methods known in the art.

Preferably, when the T cells specific for a peptide according to the present invention are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 pM, and most preferably no more than about 10 pM. It is also preferred that the substituted peptide be recognized by T cells from more than one individual, at least two, and more preferably three individuals.

In a particularly preferred embodiment of the invention the peptide consists or consists essentially of an amino acid sequence according to SEQ ID NO: 1 to SEQ ID NO: 216.

"Consisting essentially of" shall mean that a peptide according to the present invention, in addition to the sequence according to any of SEQ ID NO: 1 to SEQ ID NO: 216 or a variant thereof contains additional N- and/or C-terminally located stretches of amino acids that are not necessarily forming part of the peptide that functions as an epitope for MHC molecules.

Nevertheless, these stretches can be important to provide an efficient introduction of the peptide according to the present invention into the cells. In one embodiment of the present invention, the peptide is part of a fusion protein which comprises, for example, the 80 N-terminal amino acids of the HLA-DR antigen-associated invariant chain (p33, in the following "li") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells as described herein.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond, amino acid residues are not joined by peptide (—CO—NH—) linkages but the peptide bond is reversed. Such retro-inverso peptidomimetics may be made using methods known in the art, for example such as those described by Meziere and colleagues (Meziere et al., 1997, incorporated herein by reference). This approach involves making pseudopeptides containing changes involving the backbone, and not the orientation of side chains. They show that for MHC binding and T helper cell responses, these pseudopeptides are useful. Retro-inverse peptides, which contain NH—CO bonds instead of CO—NH peptide bonds, are much more resistant to proteolysis (Meziere et al., 1997).

A non-peptide bond is, for example, —CH$_2$—NH, —CH$_2$S—, —CH$_2$CH$_2$—, —CH=CH—, —COCH$_2$—, —CH(OH) CH$_2$—, and —CH$_2$SO—. U.S. Pat. No. 4,897,445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the bonds described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenyl-methoxy-carbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention. Similarly, a peptide or variant of the invention may be modified chemically by reacting specific amino acids either before or after synthesis of the peptide. Examples of such modifications are well known in the art (Lundblad, 2004, which is incorporated herein by reference). Chemical modification of amino acids includes, but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto (Coligan et al., 1995, the contents of which are herein incorporated by reference in their entirety).

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginyl residues. Cysteine can be modified without concomitant modification of other nucleophilic sites such as lysine and histidine. As a result, a large number of reagents are available for the modification of cysteine. The websites of companies such as Sigma-Aldrich (www.sigma-aldrich.com) provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino) propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly (ethylene)glycol and the major site of modification in the glycosylation of proteins. Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking proteins with glutaraldehyde, polyethylene glycol diacrylate and formaldehyde is used for the preparation of hydrogels. Chemical modification of allergens for immunotherapy is often achieved by carbamylation with potassium cyanate.

Another embodiment of the present invention relates to a non-naturally occurring peptide wherein said peptide consists or consists essentially of an amino acid sequence according to SEQ ID NO: 1 to SEQ ID NO: 216 and has been synthetically produced (e.g. synthesized) as a pharmaceutically acceptable salt. Methods to synthetically produce peptides are well known in the art. The salts of the peptides according to the present invention differ substantially from the peptides in their state(s) in vivo, as the peptides generated in vivo are no salts. The non-natural salt form of the peptide mediates the solubility of the peptide, in particular in the context of pharmaceutical compositions comprising the peptides, e.g. the peptide vaccines as disclosed herein. A sufficient and at least substantial solubility of the peptide(s) is required in order to efficiently provide the peptides to the subject to be treated. Preferably, the salts are pharmaceutically acceptable salts of the peptides. These salts according to the invention include alkaline and earth alkaline salts such as salts of the Hofmeister series comprising as anions $PO_4^{3-}$, $SO_4^{2-}$, $CH_3COO^-$, $Cl^-$, $Br^-$, $NO_3^-$, $ClO_4^-$, $I^-$, $SCN^-$ and as cations $NH_4^+$, $Rb^+$, $K^+$, $Na^+$, $Cs^+$, $Li^+$, $Zn_2^+$, $Mg_2^+$, $Ca_2^+$, $Mn_2^+$, $Cu_2^+$ and $Ba_2^+$. Particularly salts are selected from $(NH_4)_3PO_4$, $(NH_4)_2HPO_4$, $(NH_4)H_2PO_4$, $(NH_4)_2SO_4$, $NH_4CH_3COO$, $NH_4Cl$, $NH_4Br$, $NH_4NO_3$, $NH_4ClO_4$, $NH_4I$, $NH_4SCN$, $Rb_3PO_4$, $Rb_2HPO_4$, $RbH_2PO_4$, $Rb_2SO_4$, $Rb_4CH_3COO$, $Rb_4Cl$, $Rb_4Br$, $Rb_4NO_3$, $Rb_4ClO_4$, $Rb_4I$, $Rb_4SCN$, $K_3PO_4$, $K_2HPO_4$, $KH_2PO_4$, $K_2SO_4$, $KCH_3COO$, $KCl$, $KBr$, $KNO_3$, $KClO_4$, $KI$, $KSCN$, $Na_3PO_4$, $Na_2HPO_4$, $NaH_2PO_4$, $Na_2SO_4$, $NACH_3COO$, $NaCl$, $NaBr$, $NaNO_3$, $NaClO_4$, $NaI$, $NaSCN$, $ZnCl_2CS_3PO_4$, $CS_2HPO_4$, $CsH_2PO_4$, $CS_2SO_4$, $CsCH_3COO$, $CsCl$, $CsBr$, $CsNO_3$, $CsClO_4$, $CsI$, $CsSCN$, $Li_3PO_4$, $Li_2HPO_4$, $LiH_2PO_4$, $Li_2SO_4$, $LiCH_3COO$, $LiCl$, $LiBr$, $LiNO_3$, $LiClO_4$, $LiI$, $LiSCN$, $Cu_2SO_4$, $Mg_3(PO_4)_2$, $Mg_2HPO_4$, $Mg(H_2PO_4)_2$, $Mg_2SO_4$, $Mg(CH_3COO)_2$, $MgCl_2$, $MgBr_2$, $Mg(NO_3)_2$, $Mg(ClO_4)_2$, $MgI_2$, $Mg(SCN)_2$, $MnCl_2$, $Ca_3(PO_4)_2$, $Ca_2HPO_4$, $Ca(H_2PO_4)_2$, $CaSO_4$, $Ca(CH_3COO)_2$, $CaCl_2$, $CaBr_2$, $Ca(NO_3)_2$, $Ca(ClO_4)_2$, $CaI_2$, $Ca(SCN)_2$, $Ba_3(PO_4)_2$, $Ba_2HPO_4$, $Ba(H_2PO_4)_2$, $BaSO_4$, $Ba(CH_3COO)_2$, $BaCl_2$, $BaBr_2$, $Ba(NO_3)_2$, $Ba(ClO_4)_2$, $BaI_2$, and $Ba(SCN)_2$. Particularly preferred are NH acetate, $MgCl_2$, $KH_2PO_4$, $Na_2SO_4$, KCl, NaCl, and $CaCl_2$), such as, for example, the chloride or acetate (trifluoroacetate) salts (see, e.g. Berge et al., 1977, the contents of which are incorporated by reference in their entirety).

Generally, peptides and variants (at least those containing peptide linkages between amino acid residues) may be synthesized by the Fmoc-polyamide mode of solid-phase peptide synthesis as disclosed by Lukas et al. (Lukas et al., 1981, the content of which is incorporated by reference in its entirety) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine, threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1 hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also, a combination of solid phase and solution phase methodologies for the synthesis of peptides is possible (see for example Bruckdorfer et al., 2004 and the references as cited therein, the content of which is incorporated by reference in its entirety).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by anyone, or a combination of techniques such as re-crystallization, size exclusion chromatography, ion-exchange chromatography, hydrophobic interaction chromatography and (usually) reverse-phase high performance liquid chromatography using e.g. acetonitrile/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

In order to select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (Pinheiro et al., 2015) adjusting for multiple testing by False Discovery Rate (Benjamini and Hochberg, 1995, the content of which is incorporated by reference in its entirety).

For the identification and relative quantitation of HLA ligands by mass spectrometry, HLA molecules from shock-frozen tissue samples were purified and HLA associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural tumor-associated peptides (TUMAPs) recorded from acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer samples (N>750 samples) with the fragmentation patterns of corresponding synthetic reference peptides of identical sequences. Since the peptides were directly identified as ligands of HLA molecules of primary tumors, these results provide direct evidence for the natural processing and presentation of the identified peptides on primary cancer tissue obtained from acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer patients (cf. Example 1, FIGS. 1A-1-1E-2). The discovery pipeline XPRESIDENT® v2.1 allows the identification and selection of relevant over-presented peptides which are potential targets for immunotherapy based on direct relative quantitation of HLA restricted peptide levels on cancer tissues in comparison to several different non-cancerous tissues and organs. See, e.g. U.S. Patent Application Publication No. 2013/0096016 the contents of which are incorporated by reference in their entirety. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Additional sequence information from public resources (Olexiouk et al., 2016; Subramanian et al., 2011, the contents which are incorporated by reference in their entirety) were integrated into the XPRESIDENT® discovery pipeline to enable the identification of TUMAPs from non-canonical origin. Presentation levels including error estimates for each peptide and sample were established. Peptides exclusively presented on tumor tissue and peptides over-presented in tumor versus non-cancerous tissues and organs have been identified.

HLA-peptide complexes from acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer tissue samples were purified and HLA associated peptides were isolated and analyzed by LC-MS (see Example 1). All TUMAPs contained in the present application were identified with this approach on acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer samples confirming their presentation on acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, uterine endometrial cancer, and combinations thereof.

TUMAPs identified on multiple acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

Besides over-presentation of the peptide, mRNA expression of the underlying gene was tested. mRNA data were obtained via RNASeq analyses of normal tissues and cancer tissues (see Example 2, FIGS. 2A-1-2E-2). An additional source of normal tissue data was a database of publicly available RNA expression data from around 3000 normal tissue samples (Lonsdale, 2013, the content of which is incorporated by reference in its entirety). Peptides which are derived from proteins whose coding mRNA is highly expressed in cancer tissue, but very low or absent in vital normal tissues, were preferably included in the present invention.

The present invention provides peptides that are useful in treating cancers/tumors, preferably acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer that over- or exclusively present the peptides of the invention. These peptides were shown by MS to be naturally presented by HLA molecules on primary human acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer samples.

Many of the source genes/proteins (also designated "full-length proteins" or "underlying proteins") from which the peptides are derived were shown to be highly overexpressed in cancer compared with normal tissues-"normal tissues" in relation to this invention shall mean either healthy blood, brain, heart, liver, lung, adipose tissue, adrenal gland, bile duct, bladder, bone, bone marrow, esophagus, eye, gallbladder, head&neck, large intestine, small intestine, kidney, lymph node, central nerve, peripheral nerve, pancreas, parathyroid gland, peritoneum, pituitary, pleura, skeletal muscle, skin, spinal cord, spleen, stomach, thyroid, trachea, and ureter cells or other normal tissue cells such as breast, ovary, placenta, prostate, testis, thymus and uterus, demonstrating a high degree of tumor association of the source genes (see Example 2). Moreover, the peptides themselves are strongly over-presented on tumor tissue-"tumor tissue" in relation to this invention shall mean a sample from a patient suffering from acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer, but not on normal tissues (see Example 1).

HLA bound peptides can be recognized by the immune system, specifically T lymphocytes. T cells can destroy the cells presenting the recognized HLA-peptide complex, e.g. acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer cells presenting the derived peptides.

The peptides of the present invention are over-presented in cancer tissue compared to normal tissues and thus can be used for the production of antibodies and/or TCRs, such as soluble TCRs, according to the present invention (see Table 9). Furthermore, the peptides when complexed with the respective MHC can be used for the production of antibodies and/or TCRs, in particular soluble TCRs, according to the present invention, as well. Respective methods are well known to the person of skill and can be found in the respective literature as well (see also below). Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e., an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The present description further relates to TCRs comprising an alpha chain and a beta chain ("alpha/beta TCRs"). Also provided are peptides according to the invention capable of binding to TCRs and antibodies when presented by an MHC molecule.

The present description also relates to fragments of the TCRs according to the invention that are capable of binding to a peptide antigen according to the present invention when presented by an HLA molecule. The term particularly relates to soluble TCR fragments, for example TCRs missing the transmembrane parts and/or constant regions, single chain TCRs, and fusions thereof for example to Immunoglobulin.

The present description also relates to nucleic acids, vectors and host cells expressing TCRs and peptides of the present description; and methods of using the same.

The term "T cell receptor" (abbreviated TCR) refers to a heterodimeric molecule comprising an alpha polypeptide chain (alpha chain) and a beta polypeptide chain (beta chain), wherein the heterodimeric receptor is capable of binding to a peptide antigen presented by an HLA molecule. The term also includes so-called gamma/delta TCRs.

In one embodiment the description provides a method of producing a TCR as described herein, the method comprising culturing a host cell capable of expressing the TCR under conditions suitable to promote expression of the TCR.

The description in another aspect relates to methods according to the description, wherein the antigen is loaded onto class I or II MHC molecules expressed on the surface of a suitable antigen-presenting cell or artificial antigen-presenting cell by contacting a sufficient amount of the antigen with an antigen-presenting cell or the antigen is loaded onto class I or II MHC tetramers by tetramerizing the antigen/class I or II MHC complex monomers.

The alpha and beta chains of alpha/beta TCR's, and the gamma and delta chains of gamma/delta TCRs, are generally regarded as each having two "domains", namely variable and constant domains. The variable domain consists of a concatenation of the variable region (V) and the joining region (J). The variable domain may also include a leader region (L). Beta and delta chains may also include a diversity region (D). The alpha and beta constant domains may also include C-terminal transmembrane (TM) domains that anchor the alpha and beta chains to the cell membrane.

With respect to gamma/delta TCRs, the term "TCR gamma variable domain" as used herein refers to the concatenation of the TCR gamma V (TRGV) region without leader region (L), and the TCR gamma J (TRGJ) region, and the term TCR gamma constant domain refers to the extracellular TRGC region, or to a C-terminal truncated TRGC sequence. Likewise, the term "TCR delta variable domain" refers to the concatenation of the TCR delta V (TRDV) region without leader region (L) and the TCR delta D/J (TRDD/TRDJ) region, and the term "TCR delta constant domain" refers to the extracellular TRDC region, or to a C-terminal truncated TRDC sequence.

Alpha/beta heterodimeric TCRs of the present description may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned above, alpha/beta hetero-dimeric TCRs of the present description may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

TCRs of the present description may comprise a detectable label selected from the group consisting of a radionuclide, a fluorophore and biotin. TCRs of the present description may be conjugated to a therapeutically active agent, such as a radionuclide, a chemotherapeutic agent, or a toxin.

Detectable Labels

Detectable labels may be for example fluorescent dyes, enzymes, substrates, bioluminescent materials, radioactive materials, and chemiluminescent labels. Exemplary enzymes labels include, but are not limited to, horseradish peroxidase, acetylcholinesterase, alkaline phosphatase, b-galactosidase and luciferase. Exemplary fluorophores (fluorescent materials) include, but are not limited to, rhodamine, fluorescein, fluorescein isothiocyanate, umbelliferone, dichlorotriazinylamine, phycoerythrin and dansyl chloride. Exemplary chemiluminescent labels include, but are not limited to, luminol. Exemplary bioluminescent materials include, but are not limited to, luciferin and aequorin. Exemplary radioactive materials include, but are not limited to, bismuth-213 ($^{213}$Bs), carbon-14 ($^{14}$C), carbon-11 ($^{11}$C), chlorine-18 ($^{18}$Cl), chromium-51 ($^{51}$Cr), cobalt-57 ($^{57}$Co), cobalt-60 ($^{60}$Co), copper-64 ($^{64}$Cu), copper-67 ($^{67}$Cu), dysprosium-165 ($^{165}$Dy), erbium-169 ($^{169}$Er), fluorine-18 ($^{18}$F), gallium-67 ($^{67}$Ga), gallium-68 ($^{68}$Ga), germanium-68 ($^{68}$Ge), holmium-166 ($^{166}$Ho), indium-111 ($^{111}$In), iodine-123 ($^{123}$I), iodine-124 ($^{124}$I), iodine-125 ($^{125}$I), iodine-131 ($^{131}$I), iridium-192 ($^{192}$Ir), iron-59 ($^{59}$Fe), krypton-81 ($^{81}$Kr), lead-212 ($^{212}$Pb), lutetium-177 ($^{177}$Lu), molybdenum-99 ($^{99}$Mo), nitrogen-13 ($^{13}$N), oxygen-15 ($^{15}$O), palladium-103 ($^{103}$Pd), phosphorus-32 ($^{32}$P), potassium-42 ($^{42}$K), rhenium-186 ($^{186}$Re), rhenium-188 ($^{188}$Re), rubidium-81 ($^{81}$Rb), rubidium-82 ($^{82}$Rb), samarium-153 ($^{153}$Sm), selenium-75 ($^{75}$Se), sodium-24 ($^{24}$Na), strontium-82 ($^{82}$Sr), strontium-89 ($^{89}$Sr), sulfur 35 ($^{35}$S), technetium-99m ($^{99}$Tc), thallium-201 ($^{201}$Tl), tritium ($^{3}$H), xenon-133 ($^{133}$Xe), ytterbium-169 ($^{169}$Yb), ytterbium-177 ($^{177}$Yb), and yttrium-90 ($^{90}$Y).

Radionuclides

Radionuclides emit alpha or beta particles (e.g. radioimmunoconjugates). Such radioactive isotopes include, but are not limited to, beta-emitters such as phosphorus-32 ($^{32}$P), scandium-47 ($^{47}$Sc), copper-67 ($^{67}$Cu), gallium-67 ($^{67}$Ga), yttrium-88 ($^{88}$Y), yttrium-90 ($^{90}$Y), iodine-125 ($^{125}$I), iodine-131 ($^{131}$I), samarium-153 ($^{153}$Sm), lutetium-177 ($^{177}$Lu), rhenium-186 ($^{186}$Re), rhenium-188 ($^{188}$Re), and alpha-emitters such as astatine-211 ($^{211}$At), lead-212 ($^{212}$Pb), bismuth-212 ($^{212}$Bi), bismuth-213 ($^{213}$Bi) or actinium-225 ($^{225}$Ac).

Toxins

Toxins include, but are not limited to, methotrexate, aminopterin, 6-mercaptopurine, 6-thioguanine, cytarabine, 5-fluorouracil dacarbazine; alkylating agents such as mechlorethamine, thiotepa chlorambucil, melphalan, carmustine (BSNU), mitomycin C, lomustine (CCNU), 1-methylnitrosourea, cyclophosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, caminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine. Other cytotoxic agents include paclitaxel (TAXOL®), ricin, *Pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents Therapeutic agents include, but are not limited to, carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, vinca alkaloids, mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux®, Avastin®, Pertuzumab, anti-CD20 antibodies, Rituxan, RTM, ocrelizumab, ofatumumab, DXL625, Herceptin®, or any combination thereof. Toxic enzymes from plants and bacteria such as ricin, diphtheria toxin and *Pseudomonas* toxin may be used to generate cell type specific killing reagents (Youle et al., 1980, Gilliland et al., 1980, Krolick et al., 1980). Other cytotoxic agents include cytotoxic ribonucleases (See U.S. Pat. No. 6,653,104, the contents of each reference which are incorporated by reference in their entireties).

In an embodiment, a TCR of the present description having at least one mutation in the alpha chain and/or having at least one mutation in the beta chain has modified glycosylation compared to the unmutated TCR.

In an embodiment, a TCR comprising at least one mutation in the TCR alpha chain and/or TCR beta chain has a binding affinity for, and/or a binding half-life for, a peptide-HLA molecule complex, which is at least double that of a TCR comprising the unmutated TCR alpha chain and/or unmutated TCR beta chain. Affinity-enhancement of tumor specific TCRs, and its exploitation, relies on the existence of a window for optimal TCR affinities. The existence of such a window is based on observations that TCRs specific for e.g. HLA-restricted pathogens have $K_d$ values that are generally about 10-fold lower when compared to TCRs specific for e.g. HLA-restricted tumor-associated self-antigens. It is now known, although tumor antigens have the potential to be immunogenic, because tumors arise from the individual's own cells only mutated proteins or proteins with altered translational processing will be seen as foreign by the immune system. Antigens that are upregulated or overexpressed (so called self-antigens) will not necessarily induce a functional immune response against the tumor: T cells expressing TCRs that are highly reactive to these antigens will have been negatively selected within the thymus in a process known as central tolerance, meaning that only T cells with low-affinity TCRs for self-antigens remain. Therefore, affinity of TCRs or variants of the present description to peptides can be enhanced by methods well known in the art.

The present description further relates to a method of identifying and isolating a TCR according to the present description, said method comprising incubating PBMCs from healthy donors negative for the respective HLA allotype with HLA-peptide monomers, incubating the PBMCs with tetramer-phycoerythrin (PE) and isolating the high avidity T cells by fluorescence activated cell sorting (FACS) Calibur analysis.

The present description further relates to a method of identifying and isolating a TCR according to the present description, said method comprising obtaining a transgenic mouse with the entire human TCRαβ gene loci (1.1 and 0.7 Mb), whose T cells express a diverse human TCR repertoire that compensates for mouse TCR deficiency, immunizing the mouse with a peptide, incubating PBMCs obtained from the transgenic mice with tetramer-phycoerythrin (PE), and isolating the high avidity T cells by fluorescence activated cell sorting (FACS) Calibur analysis.

In one aspect, to obtain T cells expressing TCRs of the present description, nucleic acids encoding TCR-alpha and/or TCR-beta chains of the present description are cloned into expression vectors, such as gamma retrovirus or lentivirus. The recombinant viruses are generated and then tested for functionality, such as antigen specificity and functional avidity. An aliquot of the final product is then used to transduce the target T cell population (generally purified from patient PBMCs), which is expanded before infusion into the patient.

In another aspect, to obtain T cells expressing TCRs of the present description, TCR RNAs are synthesized by techniques known in the art e.g. in vitro transcription systems. The in vitro synthesized TCR RNAs are then introduced into primary CD8-positive T cells obtained from healthy donors by electroporation to re-express tumor specific TCR-alpha and/or TCR-beta chains.

To increase the expression, nucleic acids encoding TCRs of the present description may be operably linked to strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter, elongation factor (EF)-1a and the spleen focus-forming virus (SFFV) promoter. In a preferred embodiment, the promoter is heterologous to the nucleic acid being expressed.

In addition to strong promoters, TCR expression cassettes of the present description may contain additional elements that can enhance transgene expression, including a central polypurine tract (cPPT), which promotes the nuclear translocation of lentiviral constructs (Follenzi et al., 2000), and the woodchuck hepatitis virus post-transcriptional regulatory element (wPRE), which increases the level of transgene expression by increasing RNA stability (Zufferey et al., 1999, the contents of which are incorporated by reference in their entirety).

The alpha and beta chains of a TCR of the present invention may be encoded by nucleic acids located in separate vectors or may be encoded by polynucleotides located in the same vector.

Achieving high level TCR surface expression requires that both the TCR-alpha and TCR-beta chains of the introduced TCR be transcribed at high levels. To do so, the TCR-alpha and TCR-beta chains of the present description may be cloned into bi-cistronic constructs in a single vector, which has been shown to be capable of overcoming this obstacle. The use of a viral internal ribosomal entry site (IRES) between the TCR-alpha and TCR-beta chains results in the coordinated expression of both chains, because the TCR-alpha and TCR-beta chains are generated from a single transcript that is broken into two proteins during translation, ensuring that an equal molar ratio of TCR-alpha and TCR-beta chains are produced (Schmitt et al., 2009, the contents of which are incorporated by reference in their entirety).

Nucleic acids encoding TCRs of the present description may be codon optimized to increase expression from a host cell. Redundancy in the genetic code allows some amino acids to be encoded by more than one codon, but certain codons are less "optimal" than others because of the relative availability of matching tRNAs as well as other factors (Gustafsson et al., 2004). Modifying the TCR-alpha and TCR-beta gene sequences such that each amino acid is encoded by the optimal codon for mammalian gene expression, as well as eliminating mRNA instability motifs or cryptic splice sites, has been shown to significantly enhance TCR-alpha and TCR-beta gene expression (Scholten et al., 2006, the contents of these references are herein incorporated by reference in their entirety).

Furthermore, mispairing between the introduced and endogenous TCR chains may result in the acquisition of specificities that pose a significant risk for autoimmunity. For example, the formation of mixed TCR dimers may reduce the number of CD3 molecules available to form properly paired TCR complexes, and therefore can significantly decrease the functional avidity of the cells expressing the introduced TCR (Kuball et al., 2007, the contents of which are incorporated by reference in their entirety).

To reduce mispairing, the C-terminus domain of the introduced TCR chains of the present description may be modified in order to promote interchain affinity, while decreasing the ability of the introduced chains to pair with the endogenous TCR. These strategies may include replacing the human TCR-alpha and TCR-beta C-terminus domains with their murine counterparts (murinized C-terminus domain); generating a second interchain disulfide bond in the C-terminus domain by introducing a second cysteine residue into both the TCR-alpha and TCR-beta chains of the introduced TCR (cysteine modification); swapping interacting residues in the TCR-alpha and TCR-beta chain C-terminus domains ("knob-in-hole"); and fusing the variable domains of the TCR-alpha and TCR-beta chains directly to CD3ζ (CD3ζ fusion) (Schmitt et al., 2009).

In an embodiment, a host cell is engineered to express a TCR of the present description. In preferred embodiments, the host cell is a human T cell or T cell progenitor. In some embodiments the T cell or T cell progenitor is obtained from a cancer patient. In other embodiments the T cell or T cell progenitor is obtained from a healthy donor. Host cells of the present description can be allogeneic or autologous with respect to a patient to be treated. In one embodiment, the host is a gamma/delta T cell transformed to express an alpha/beta TCR.

A "pharmaceutical composition" is a composition suitable for administration to a human being in a medical setting. Preferably, a pharmaceutical composition is sterile and produced according to GMP guidelines.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH$_2$ group) involving reaction with a suitable acid. Suitable acids for preparing acid salts include both organic acids e.g. acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

Preferably, the medicament of the present invention is an immunotherapeutic such as a vaccine. It may be administered directly into the patient, into the affected organ or systemically intravenous (i.v.), sub-cutaneous (s.c.), intradermal (i.d.), intraperitoneal (i.p.), intramuscular (i.m.) or applied ex vivo to cells derived from the patient or a human cell line which are subsequently administered to the patient or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as Interleukin-2. The peptide may be substantially pure or combined with an immune-stimulating adjuvant (see below) or used in combination with immune-stimulatory cytokines, or be administered with a suitable delivery system, for example liposomes. The peptide may also be conjugated to a suitable carrier such as keyhole limpet hemocyanin (KLH) or mannan (see WO 95/18145 and Longenecker et al., 1993, the contents both of which are incorporated by reference in their entirety). The peptide may also be tagged, may be a fusion protein, or may be a hybrid molecule. The peptides whose sequences are given in the present invention are expected to stimulate CD4 or CD8 T cells. However, stimulation of CD8 T cells is more efficient in the presence of help provided by CD4 T helper cells. Thus, for MHC class I epitopes that stimulate CD8 T cells the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth SEQ ID NO: 1 to SEQ ID NO: 216, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns as long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, CN, USA.

A desirable method of modifying the DNA encoding the polypeptide of the invention employs the polymerase chain reaction as disclosed by Saiki et al. (Saiki et al., 1988, the contents of which are incorporated by reference in their entirety). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed for example in U.S. Pat. Nos. 4,440,859, 4,530,901, 4,582,800, 4,677,063, 4,678,751, 4,704,362, 4,710,463, 4,757,006, 4,766,075, and 4,810,648, the contents each of which are incorporated by reference in their entirety.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating a DNA sequence into the expression vector, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, NJ, USA. An example of an inducible mammalian expression vector is pMSG, also available from Pharmacia. Useful yeast plasmid vectors are pRS403-406 and pRS413-416 and are generally available from Stratagene Cloning Systems, La Jolla, CA 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them. These constructs can also be used for cancer therapy and may induce immune responses both involving MHC I and MHC II.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, MD, USA, and RR1 available from the American Type Culture Collection (ATCC) of Rockville, MD, USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, CA 92037, USA. Preferred mammalian host cells include chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in the literature (Balbas and Lorence, 2004).

Transformation of appropriate cell hosts with a DNA construct of the present invention is accomplished by well-known methods that typically depend on the type of vector used. With regard to transformation of prokaryotic host cells, see for example Cohen et al. or Green and Sambrook (Cohen et al., 1972; Green and Sambrook, 2012). Transformation of yeast cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, MD 20877, USA. Electroporation is also useful for transforming and/or transfecting cells and is well known in the art for transforming yeast cell, bacterial cells, insect cells and vertebrate cells. The contents of each of these references are herein incorporated by reference in their entirety.

Successfully transformed cells, i.e., cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells (APCs), such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006, the contents of which are incorporated by reference in their entirety).

A further aspect of the invention provides a method of producing a peptide or its variant, the method comprising culturing a host cell and isolating the peptide from the host cell or its culture medium.

In another embodiment, the peptide, the nucleic acid or the expression vector of the invention are used in medicine. For example, the peptide or its variant may be prepared for i.v., s.c., i.d., i.p., i.m. injection. Preferred methods of peptide injection include s.c., i.d., i.p., i.m., and i.v. Preferred methods of DNA injection include i.d., i.m., s.c., i.p. and i.v. Doses of e.g. between 50 μg and 1.5 mg, preferably 125 μg to 500 µg, of peptide or DNA may be given and will depend on the respective peptide or DNA. Dosages of this range were successfully used in previous trials (Walter et al., 2012).

The polynucleotide used for active vaccination may be substantially pure or contained in a suitable vector or delivery system. The nucleic acid may be DNA, cDNA, PNA, RNA or a combination thereof. Methods for designing and introducing such a nucleic acid are well known in the art. An overview is provided by Teufel et al. (Teufel et al., 2005, the contents of which are incorporated by reference in their entirety). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response e.g. immune responses mediated by CD8-positive T cells and helper T (TH) cells to an antigen and would thus be considered useful in the medicament of the present invention.

Suitable adjuvants include, but are not limited to, 1018 ISS, aluminum salts, AMPLIVAX®, AS15, BCG, CP-870, 893, CpG7909, CyaA, dSLIM, flagellin or TLR5 ligands derived from flagellin, FLT3 ligand, GM-CSF, IC30, IC31, Imiquimod (ALDARA®), Resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g. MF59) specific for dendritic cells and their preparation have been described previously (Allison and Krummel, 1995, the contents of which are incorporated by reference in their entirety).

Cytokines may also be used. Several cytokines have been directly linked to influencing dendritic cell migration to lymphoid tissues (e.g., TNF), accelerating the maturation of dendritic cells into efficient antigen-presenting cells for T-lymphocytes (e.g., GM-CSF, IL-1 and IL-4) (U.S. Pat. No. 5,849,589, incorporated herein by reference in its entirety) and acting as immunoadjuvants (e.g., IL-2, IL-7, IL-12, IL-15, IL-21, IL-23, IFN-alpha. IFN-beta) (Gabrilovich et al., 1996, the contents of which are incorporated by reference in their entirety). In an aspect, cytokines and immunological adjuvants may be used in vitro, such as for expansion or activation of T cells, or for ex vivo uses.

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1, which is incorporated by reference in its entirety, describes the combined use of CpG oligonucleotides, non-nucleic acid adjuvants and an antigen to induce an antigen specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to, chemically modified CpGs (e.g. CpR, Idera), dsRNA analogues such as Poly(I:C) and derivates thereof (e.g. AmpliGen®, Hiltonol®, poly (ICLC), poly (IC-R), poly(I:C12U), non-CpG bacterial DNA or RNA as well as immunoactive small molecules and antibodies such as cyclophosphamide, sunitinib, immune checkpoint inhibitors including ipilimumab, nivolumab, pembrolizumab, atezolizumab, avelumab, durvalumab, and cemiplimab, Bevacizumab®, Celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGF-beta, anti-TNF-alpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, Resiquimod, GM-CSF, cyclophosphamide, sunitinib, bevacizumab, interferon-alpha, CpG oligonucleotides and derivates, Poly (I:C) and derivates, RNA, sildenafil, and particulate formulations with PLG or virosomes.

In a preferred embodiment of the pharmaceutical composition according to the invention the adjuvant is selected from the group consisting of colony-stimulating factors, such as GM-CSF, sargramostim, cyclophosphamide, imiquimod, Resiquimod, interferon-alpha, or mixtures thereof.

In a preferred embodiment of the pharmaceutical composition according to the invention, the adjuvant is cyclophosphamide, imiquimod or Resiquimod. Even more preferred adjuvants are Montanide IMS 1312, Montanide ISA 206, Montanide ISA 50V, Montanide ISA-51, poly-ICLC (Hiltonol®) and anti-CD40 mAb, or combinations thereof.

This composition is used for parenteral administration, such as subcutaneous, intradermal, intramuscular or oral administration. The composition may be administered via subcutaneous, intramuscular, intravenous, intraperitoneal, intrapleural, intravesicular, intrathecal, topical, oral administration, or a combination of routes. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. Pharmaceutically acceptable carriers include, but are not limited to, excipient, lubricant, emulsifier, stabilizer, solvent, diluent, buffer, vehicle, or a combination thereof. The peptides or T cells recognizing the peptide of the present disclosure in a complex with an MHC molecule can also be administered together with immune stimulating substances, such as cytokines shown in table 5.

TABLE 5

Immune stimulating cytokines
Cytokines

| | |
|---|---|
| EOTAXIN | IL-15 |
| G-CSF | IL-17 |
| GM-CSF | IP-10 |
| INF-γ | MIP-2 |
| IL-1α | KC |
| M-CSF | LIF |
| IL-1β | LIX |
| IL-2 | MCP-1 |
| IL-3 | MIP-1α |
| IL-4 | MIP-1β |
| IL-5 | MIG |
| IL-6 | RANTES |
| IL-7 | TNFα |
| IL-10 | IL-12 (P70) |
| IL-12 (p40) | VEGF |
| IL-13 | IL-9 |
| IL-18 | IL-21 |

Cytokines, e.g., IL-2, IL-7, IL-12, IL-15, IL-18, IL-21, IFN-α, and IFN-β, may also be used in the activation and/or expansion of T cells, such as T cells recognizing the peptide of the present disclosure in a complex with an MHC molecule.

An extensive listing of excipients that can be used in such a composition, can be, for example, taken from A. Kibbe, Handbook of Pharmaceutical Excipients (Kibbe, 2000). Other examples of suitable pharmaceutical carriers are described in Remington's Pharmaceutical Sciences (Gennaro, 1997; Banker and Rhodes, 2002, the contents of which are herein incorporated by reference in their entireties). The composition can be used for a prevention, prophylaxis and/or therapy of adenomatous or cancerous diseases. Exemplary formulations can be for example found in EP2112253.

It is important to realize that the immune response triggered by the vaccine according to the invention attacks the cancer in different cell-stages and different stages of development. Furthermore, different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Banchereau et al., 2001; Walter et al., 2012, the contents of which are incorporated by reference in their entirety).

As used herein, the term "scaffold" refers to a molecule that specifically binds to a (e.g. antigenic) determinant. In one embodiment, a scaffold is able to direct the entity to which it is attached (e.g. a (second) antigen binding moiety) to a target site, for example to a specific type of tumor cell or tumor stroma bearing the antigenic determinant (e.g. the complex of a peptide with MHC, according to the application at hand). In another embodiment a scaffold is able to activate signaling through its target antigen, for example a T cell receptor complex antigen. Scaffolds include, but are not limited to, antibodies and fragments thereof, antigen binding domains of an antibody, comprising an antibody heavy chain variable region and an antibody light chain variable region, binding proteins comprising at least one ankyrin repeat motif and single domain antigen binding (SDAB) molecules, aptamers, (soluble) TCRs and (modified) cells such as allogenic or autologous T cells. To assess whether a molecule is a scaffold binding to a target, binding assays can be performed.

"Specific" binding means that the scaffold binds the peptide-MHC complex of interest better than other naturally occurring peptide-MHC complexes, to an extent that a scaffold armed with an active molecule that is able to kill a cell bearing the specific target is not able to kill another cell without the specific target but presenting other peptide-MHC complex(es). Binding to other peptide-MHC complexes is irrelevant if the peptide of the cross-reactive peptide-MHC is not naturally occurring, i.e., not derived from the human HLA peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labelling which provides that the bound scaffold can be detected by determining the presence or absence of a signal provided by the label. For example, the scaffold can be labelled with a fluorescent dye or any other applicable cellular marker molecule. Such marker molecules are well known in the art. For example, a fluorescence-labelling, for example provided by a fluorescence dye, can provide a visualization of the bound aptamer by fluorescence or laser scanning microscopy or flow cytometry.

Each scaffold can be conjugated with a second active molecule such as for example IL-21, anti-CD3, and anti-CD28.

For further information on polypeptide scaffolds see for example the background section of WO 2014/071978A1 and the references cited therein, the contents of which are incorporated by reference in their entirety.

The peptides of the present invention can be used to generate and develop specific antibodies against MHC-peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a MHC class I or II molecule being complexed with a HLA restricted antigen (preferably a peptide according to the present invention), the method comprising: immunizing genetically engineered non-human mammal comprising cells expressing said human MHC class I or II molecule with a soluble form of a MHC class I or II molecule being complexed with said HLA restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said MHC class I or II molecule being complexed with said HLA restricted antigen.

It is thus a further aspect of the invention to provide an antibody that specifically binds to a MHC class I or II molecule being complexed with an HLA restricted antigen, wherein the antibody preferably is a polyclonal antibody, monoclonal antibody, bispecific antibody, a chimeric antibody, antibody fragments thereof, or a combination thereof.

Bispecific Antibody

In an aspect, a bispecific antibody includes an antibody capable of selectively binding two or more epitopes. Bispecific antibodies may be manufactured in a variety of ways (Holliger & Winter, 1993, the contents of which are incorporated by reference in their entirety), for instance, prepared chemically or from hybrid hybridomas, or may be any of the bispecific antibody fragments mentioned above. scFv dimers or diabodies may be used, rather than whole antibodies. Diabodies and scFv can be constructed without an Fc region, using only variable domains (usually including the variable domain components from both light and heavy chains of the source antibody), potentially reducing the effects of anti-idiotypic reaction. Other forms of bispecific antibodies include the single chain "Janusins" described by Traunecker and colleagues (Traunecker et al., 1991, the contents of which are incorporated by reference in their entirety).

Bispecific antibodies generally include two different binding domains, with each binding domain specifically binding a different epitope either on two different antigens or on the same antigen. If a bispecific antibody is capable of selectively binding two different epitopes (a first epitope and a second epitope), the affinity of the first binding for the first epitope will generally be at least one to two or three or four orders of magnitude lower than the affinity of the first binding domain for the second epitope, and vice versa. The epitopes recognized by the bispecific antibody can be on the same or a different target (e.g., on the same or a different protein). Bispecific antibodies can be made for example by combining binding domains that recognize different epitopes of the same antigen.

Some example bispecific antibodies have two heavy chains (each having three heavy chain CDRs, followed by (N-terminal to C-terminal) a $CH_1$ domain, a hinge, a $CH_2$ domain, and a $CH_3$ domain), and two immunoglobulin light chains that confer antigen-binding specificity through association with each heavy chain. However, additional architectures are envisioned, including bispecific antibodies in which the light chain(s) associate with each heavy chain but do not (or minimally) contribute to antigen-binding specificity, or that can bind one or more of the epitopes bound by the heavy chain antigen-binding regions, or that can associate with each heavy chain and enable binding of one or both of the heavy chains to one or both epitopes.

In particular embodiments, a bispecific antibody can include an antibody arm combined with an arm that binds to a triggering molecule on a leukocyte, such as a T cell receptor molecule (for example, CD3), or Fc receptors for IgG (Fc gamma R), such as Fc gamma RI (CD64), Fc gamma RII (CD32) and Fc gamma RIII (CD 16), so as to focus and localize cellular defense mechanisms to the targeted disease cell. Bispecific antibodies also can be used to localize cytotoxic agents to targeted disease cells.

Bispecific antibodies can be prepared as full-length antibodies or antibody fragments (for example, $F(ab')_2$ bispecific antibodies). See e.g. WO 1996/016673; U.S. Pat. No. 5,837,234; WO 1998/002463; U.S. Pat. No. 5,821,337, the contents of which are incorporated by reference in their entirety.

A bispecific antibody can have an extended half-life. In particular embodiments, half-life extension of a bispecific antibody can be achieved by: increasing the hydrodynamic volume of the antibody by coupling to inert polymers such as polyethylene glycol or other mimetic hydrophilic polymers; fusion or conjugation to large disordered peptides; or fusing or coupling the antibody to a ligand. These alterations and a number of others are described elsewhere (U.S. Pat. Nos. 7,083,784, 7,670,600, U.S. Patent Application Publication No. 2010/0234575, and Zwolak et al., 2017, the contents of which are incorporated by reference in their entirety). Bispecific antibodies with extended half-lives are described in for example U.S. Pat. No. 8,921,528 and U.S. Patent Application Publication No. 2014/0308285, the contents of which are incorporated by reference in their entirety.

Methods for making bispecific antibodies are known in the art. Production of full-length bispecific antibodies is based on the co-expression of two immunoglobulin heavy chain-light chain pairs, where the two chains have different specificities. See e.g., WO 1993/008829 and Traunecker et al., 1991, the contents of which are incorporated by reference in their entirety.

Polyclonal Antibody

Methods for making polyclonal antibodies are known in the art. Polyclonal antibodies are heterogeneous populations of antibody molecules derived from the sera of animals immunized with an antigen. Polyclonal antibodies which selectively bind a peptide according to SEQ ID NO: 1 to SEQ ID NO: 216, or a variant or fragment thereof may be made by methods well-known in the art (see, e.g., Howard & Kaser, 2007, the contents of which are incorporated by reference in their entirety.

Chimeric Antibody

Chimeric antibodies are molecules different portions of which are derived from different animal species, such as those having variable region derived from a murine antibody and a human immunoglobulin constant region, which are primarily used to reduce immunogenicity in application and to increase yields in production for example where murine monoclonal antibodies have higher yields from hybridomas but higher immunogenicity in humans, such that human murine chimeric monoclonal antibodies are used. Chimeric antibodies and methods for their production are known in the art (Cabilly et al., 1984; Morrison et al., 1984; Boulianne et al., 1984; European Patent Application 173494 (1986); WO 86/01533 (1986); European Patent Application 184187 (1986); Sahagan et al., 1986; Liu et al., 1987; Sun et al., 1987; Better et al., 1988; Harlow & Lane, 1998; U.S. Pat. No. 5,624,659, the contents of which are incorporated by reference in their entirety).

Antibody Fragments

In addition to entire immunoglobulins (or their recombinant counterparts), immunoglobulin fragments comprising the epitope binding site (e.g., Fab', F(ab')$_2$, or other fragments) may be synthesized. "Fragments" or minimal immunoglobulins may be designed utilizing recombinant immunoglobulin techniques. For instance, "Fv" immunoglobulins for use in the present invention may be produced by synthesizing a fused variable light chain region and a variable heavy chain region. Combinations of antibodies are also of interest, e.g., diabodies, which comprise two distinct Fv specificities. Antigen-binding fragments of immunoglobulins include, but are not limited to, SMIPs (small molecule immunopharmaceuticals), camelbodies, nanobodies, and IgNAR.

Respective methods for producing such antibodies and single chain MHC class I complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003, which for the purposes of the present invention are incorporated by reference in their entireties).

Preferably, the antibody is binding with a binding affinity of <100 nM, more preferably <50 nM, more preferably <10 nM, more preferably <1 nM, more preferably <0.1 nM, more preferably <0.01 nM, to the complex, which is also regarded as "specific" in the context of the present invention.

The present invention relates to a peptide comprising an amino acid sequence selected from the group consisting of
SEQ ID NO: 1 to SEQ ID NO: 216,
and a variant sequence thereof which maintains capacity to bind to MHC molecule(s) and/or induce T cells cross-reacting with said variant peptide,
or a pharmaceutically acceptable salt thereof.

The peptides disclosed bind to HLA-A*01, HLA-A*02, HLA-A*03, HLA-A*24, HLA-B*07, HLA-B-08, HLA-B*44 allotype MHC molecules. Likewise, the peptide variant's capacity to bind to MHC molecule(s) relates to one of these HLA allotype MHC molecules.

In one embodiment, variant sequences of the claimed peptides in the above meaning are sequences which have substitutions in their so-called "anchoring position".

Note that these anchoring positions in MHC restricted peptides comprise amino acid residues which mediate binding of the peptide to the peptide binding groove in the MHC. They play only a minor role in the binding reaction between the binding polypeptide and the peptide-MHC complex, meaning that substitutions in these positions do not significantly affect immunogenicity or TCR/antibody binding of a peptide modified in such way.

For HLA alleles binding the peptides of the current invention, the anchoring positions of the respective MHC restricted peptide as well as the preferred amino acid residues in these positions are given in table 6.

TABLE 6

Anchoring position and preferred amino acids in these positions for the HLA alleles the peptides of the invention bind to.

| HLA subtype | Anchor position 1 | Accepted amino acid residues | Anchor position 2 | Accepted amino acid residues | Anchor position 3 | Accepted amino acid residues |
|---|---|---|---|---|---|---|
| HLA-A*01:01 | Position 2 | Threonine (T) Serine (S) | Position 3 | Aspartic Acid (D) Glutamic Acid (E) | C-terminal | Tyrosine (Y) |
| HLA-A*02:01 | Position 2 | Leucin (L) Methionine (M) | n/a | n/a | Position 9 | Leucin (L) Valin (V) |
| HLA-A*03:01 | Position 2 | Leucine (L) Valine (V) | n/a | n/a | C-terminal | Lysine (K) |
| HLA-A*24:02 | Position 2 | Tyrosine (Y) | n/a | n/a | C-terminal | Phenylalanine (F) |
| HLA-B*07:02 | Position 2 | Proline (P) | n/a | n/a | C-terminal | Leucine (L) |
| HLA-B*08:01 | Position 3 | Lysine (K) | Position 5 | Lysine (K) Arginine (R) | C-terminal | Leucine (L) |
| HLA-B*44:02 | Position 2 | Glutamic Acid (E) | n/a | n/a | C-terminal | Tryptophane (W) Phenylalanine (F) Tyrosine (Y) |

Furthermore, the invention relates to variants thereof which are at least 88% homologous to SEQ ID NO: 1 to SEQ ID NO: 216, provided they binds to MHC molecule(s) and/or induce T cells cross-reacting with said variant peptide.

In one embodiment, variant sequences of the claimed peptides in the above meaning are sequences which are modified by at least one conservative amino acid substitution. The definition and scope of the term "conservative amino acid substitution" is disclosed in table 2 and 3, and the description related thereto.

In one embodiment, said peptide has the ability to bind to an MHC class I molecule, and, when bound to said MHC, is capable of being recognized by CD4 and/or CD8 T cells.

In one embodiment, the MHC class I molecule is one of the aforementioned HLA allotypes MHC molecule.

The present invention further relates to a peptide comprising a sequence that is selected from the group consisting of SEQ ID NO: 1 to SEQ ID NO: 216 or a variant thereof which is at least 88% homologous (preferably identical) to SEQ ID NO: 1 to SEQ ID NO: 216, wherein said peptide or variant has an overall length of between 8 and 30, and preferred between 8 and 12 amino acids or between 9 and 30, and preferred between 9 and 12 amino acids if the selected peptide has a length of 9 amino acids or between 10 and 30, and preferred between 10 and 12 amino acids if the selected peptide has a length of 10 amino acids.

In one embodiment said peptide or variant thereof comprises 1 to 4 additional amino acids at the C- and/or N-terminus of the respective sequence. See table 4 for further details. In one embodiment, said peptide or variant thereof has a length of up to 30 amino acids. In one embodiment, said peptide or variant thereof has a length of up to 16 amino acids. In one embodiment, said peptide or variant thereof has a length of up to 12 amino acids.

In one embodiment, said peptide or variant thereof has an overall length from 8 to 30 amino acids. In one embodiment, said peptide or variant thereof has an overall length from 8 to 16 amino acids. In one embodiment, said peptide or variant thereof has an overall length from 8 to 12 amino acids.

In one embodiment, said peptide or variant thereof has an overall length from 9 to 30 amino acids. In one embodiment, said peptide or variant thereof has an overall length from 9 to 16 amino acids. In one embodiment, said peptide or variant thereof has an overall length from 9 to 12 amino acids.

In one embodiment, said peptide or variant thereof has an overall length from 10 to 30 amino acids. In one embodiment, said peptide or variant thereof has an overall length from 10 to 16 amino acids. In one embodiment, said peptide or variant thereof has an overall length from 10 to 12 amino acids.

In one embodiment, said peptide or variant thereof has a length according to the respective SEQ ID NO: 1 to SEQ ID NO: 216. In one embodiment, the peptide consists or consists essentially of the amino acid sequence according to SEQ ID NO: 1 to SEQ ID NO: 216.

The present invention further relates to the peptides according to the invention, wherein the peptide includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as for example an antibody that is specific for dendritic cells.

The present invention further relates to an antibody, or a functional fragment thereof, that specifically recognizes or binds to the peptide or variant thereof according to the present invention, or to the peptide or variant thereof according to the present invention when bound to an MHC molecule.

In one embodiment, the MHC molecule is an MHC molecule of the allotype HLA-A*01:01, HLA-A*02:01, HLA-A*03:01, HLA-A*24:02, HLA-B*07:02, HLA-B*08:01, HLA-B*44:02, plus optionally other HLA allotypes.

In further embodiments, such antibody is soluble or membrane bound. In further embodiments, such antibody is a monoclonal antibody or fragment thereof. In further embodiments, such antibody carries a further effector function such as an immune stimulating domain or toxin.

The present invention further relates to a T cell receptor, or a functional fragment thereof, that is reactive with, or binds to, an MHC ligand, wherein said ligand is the peptide or variant thereof according to the present invention, or the peptide or variant thereof according to the present invention when bound to an MHC molecule.

In one embodiment, the MHC molecule is at least one selected from the group consisting of HLA-A*01:01, HLA-A*02:01, HLA-A*03:01, HLA-A*24:02, HLA-B*07:02, HLA-B*08:01 and HLA-B*44:02, plus optionally other HLA allotypes.

In further embodiments, said T cell receptor is provided as a soluble molecule. In further embodiments, said T cell receptor carries a further effector function such as an immune stimulating domain or toxin.

The present invention further relates to a nucleic acid, encoding for a peptide or variant thereof according to the invention, an antibody or fragment thereof according to the invention, or a T cell receptor or fragment thereof according to the invention.

The present invention further relates to the nucleic acid according to the invention that is DNA, cDNA, PNA, RNA or combinations thereof.

In one embodiment, said nucleic acid is linked to a heterologous promoter sequence. In one embodiment, said nucleic acid is provided as an expression vector expressing and/or comprising said nucleic acid.

The present invention further relates to a recombinant host cell comprising a peptide or variant thereof according to the invention, an antibody or fragment thereof according to the invention, a T cell receptor or fragment thereof according to the invention, or a nucleic acid or expression vector according to the invention.

The present invention further relates to an in vitro method for producing activated T lymphocytes, the method comprising contacting in vitro T cells with antigen loaded human class I or II MHC molecules expressed on the surface of a suitable antigen-presenting cell or an artificial construct mimicking an antigen-presenting cell for a period of time sufficient to activate said T cells in an antigen specific manner, wherein said antigen is a peptide or variant thereof according to the respective description.

In one embodiment, the antigen-presenting cell comprises an expression vector capable of expressing said peptide containing SEQ ID NO: 1 to SEQ ID NO: 216 or said variant amino acid sequence.

The present invention further relates to an in vitro method of producing a peptide according to the present invention, said method comprising culturing the host cell according to the present invention, and isolating the peptide from said host cell or its culture medium.

The present invention further relates to an activated T lymphocyte, produced by the method according to the present invention, wherein said T lymphocyte selectively recognizes a cell which presents a peptide or variant thereof according to the present invention. Said presentation can be an aberrant presentation or aberrant expression.

The present invention further relates to pharmaceutical composition comprising at least one active ingredient selected from the group consisting of
  the peptide or variant thereof according to the present invention,
  the antibody or fragment thereof according to the present invention,
  the T cell receptor or fragment thereof according to the present invention,
  the nucleic acid or the expression vector according to the present invention,
  the host cell according to the present invention,
  or the activated T lymphocyte according to the present invention,
and a pharmaceutically acceptable carrier.

In one embodiment, such pharmaceutical composition is personalized pharmaceutical composition for an individual patient. In one embodiment, the pharmaceutical composition is a vaccine. The method could also be adapted to produce T cell clones for down-stream applications, such as TCR isolations, or soluble antibodies, and other treatment options.

A "personalized pharmaceutical" shall mean specifically tailored therapies for one individual patient that will only be used for therapy in such individual patient, including actively personalized cancer vaccines and adoptive cellular therapies using autologous patient tissue.

The present invention further relates to a method for producing the peptide or variant thereof according to the present invention, the antibody or fragment thereof according to the present invention, or the T cell receptor or fragment thereof according to the present invention, and isolating the peptide or variant thereof, the antibody or fragment thereof or the T cell receptor or fragment thereof from said host cell and/or its culture medium.

The present invention further relates to a peptide or variant thereof according to the present invention, the antibody or fragment thereof according to the present invention, the T cell receptor or fragment thereof according to the present invention, the nucleic acid or the expression vector according to the present invention, the host cell according to the present invention, or the activated T lymphocyte according to the present invention, for use in medicine, or for use in the manufacture of a medicine.

The present invention further relates to a method of killing target cells in a patient, which target cells aberrantly express a polypeptide comprising any amino acid sequence according to the present invention. Said method comprises administering to the patient an effective number of activated T lymphocytes as according to the present invention.

Likewise, the present invention relates to an activated T lymphocyte according to the present invention for use in the killing of target cells in a patient, which target cells present a polypeptide comprising any amino acid sequence according to the present invention, or for use in the manufacture of a medicament for the killing of such target cells.

The present invention further relates to method of treating a patient
being diagnosed for,
suffering from or
being at risk of developing
cancer, the method comprising administering to the patient an effective amount of the peptide or variant thereof according to the present invention, the antibody or fragment thereof according to the present invention, the T cell receptor or fragment thereof according to the present invention, the nucleic acid or the expression vector according to the present invention, the host cell according to the present invention, or the activated T lymphocyte according to the present invention.

The present invention further relates to method of eliciting an immune response in a patient
being diagnosed for,
suffering from or
being at risk of developing
cancer, the method comprising administering to the patient an effective amount of the peptide or variant thereof according to the present invention, the antibody or fragment thereof according to the present invention, the T cell receptor or fragment thereof according to the present invention, the nucleic acid or the expression vector according to the present invention, the host cell according to the present invention, or the activated T lymphocyte according to the present invention.

Likewise, the present invention further relates to the peptide or variant thereof according to the present invention, the antibody or fragment thereof according to the present invention, the T cell receptor or fragment thereof according to the present invention, the nucleic acid or the expression vector according to the present invention, the host cell according to the present invention, or the activated T lymphocyte according to the present invention, for use the treatment of a patient
being diagnosed for,
suffering from or
being at risk of developing
cancer, or for use in the manufacture of a medicament for the treatment of such patient.

The present invention further relates to a use according to the invention, wherein the medicament is a vaccine.

The present invention further relates to the method or the peptide, antibody, T cell receptor, nucleic acid, host cell or activated T lymphocyte for use according to the invention, wherein said cancer is selected from the group consisting of acute myeloid leukemia, breast cancer, cholangiocellular carcinoma, chronic lymphocytic leukemia, colorectal cancer, gallbladder cancer, glioblastoma, gastric cancer, gastroesophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer.

The present invention further relates to a kit comprising:
(a) a container comprising a pharmaceutical composition containing the pharmaceutical composition according to the present invention in solution or in lyophilized form;
(b) optionally, a second container containing a diluent or reconstituting solution for the lyophilized formulation;
(c) optionally, at least one more peptide selected from the group consisting of SEQ ID NO: 1 to SEQ ID NO: 216.

In further embodiments, the kit comprises one or more of a buffer, a diluent, a filter, a needle, or a syringe.

In a further aspect there is provided a method of diagnosing cancer in a subject. The method includes using a binding molecule as provided herein. Generally, such a binding molecule is a proteinaceous binding molecule that specifically binds to a peptide as provided herein, or to the respective peptide when in complex with an MHC molecule, see above. The method may include administering the binding molecule to a subject or contacting the binding molecule with a sample that has been obtained from a subject. Typically the method involves contacting cells, including cells as part of tissue, from or in the subject with a binding molecule as disclosed herein. In this regard in some embodiment the method includes providing a sample from the subject. The method furthermore includes detecting binding of the binding molecule to cells of or in the subject.

The present invention further relates to particular marker proteins and biomarkers based on the peptides according to the present invention, herein called "targets" that can be used in the diagnosis and/or prognosis of at least one of acute myeloid leukemia, breast cancer, cholangiocellular carcinoma, chronic lymphocytic leukemia, colorectal cancer, gallbladder cancer, glioblastoma, gastric cancer, gastroesophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer.

The term "antibody" or "antibodies" is used herein in a broad sense and includes both polyclonal and monoclonal antibodies. In addition to intact or "full" immunoglobulin molecules, also included in the term "antibodies" are fragments (e.g. CDRs, Fv, Fab and Fc fragments) or polymers of those immunoglobulin molecules and humanized versions of immunoglobulin molecules, as long as they exhibit any of the desired properties (e.g., specific binding of acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer marker polypeptide) according to the invention.

Whenever possible, the antibodies of the invention may be purchased from commercial sources. The antibodies of the invention may also be generated using well-known methods. The skilled artisan will understand that either full length of acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer marker polypeptides or fragments thereof may be used to generate the antibodies of the invention. A polypeptide to be used for generating an antibody of the invention may be partially or fully purified from a natural source or may be produced using recombinant DNA techniques.

For example, a cDNA encoding a peptide according to the present invention, such as a peptide according to SEQ ID NO: 1 to SEQ ID NO: 216 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind to the acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc. (Greenfield, 2014, the contents of which are incorporated by reference in their entirety)). For example, the antibodies may be tested in ELISA assays or, Western blots, immunohistochemical staining of formalin-fixed cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated by reference in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348 and U.S. Pat. No. 4,342,566, the contents of which are incorporated by reference in their entirety. Papain digestion of antibodies typically produces two identical antigen binding fragments, called Fab fragments, each with a single antigen binding site, and a residual Fc fragment. Pepsin treatment yields a F(ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567, the contents of which are incorporated by reference in their entirety), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

In an aspect, the antibody of the present disclosure can also be obtained through phage display, or ribosome display, or yeast display, or bacteria display, or Baculovirus display, or mammal cell display, or mRNA display. These methods are all conventional techniques in the art, the specific operations thereof can be seen in corresponding textbooks or operation manuals (Mondon et al., 2008; the content of which is hereby incorporated by reference in its entirety). Using phage display as an example, separate antibody genes may be inserted into the DNA of phages, so that the variable regions on the antibody molecules that can bind the antigens may be coupled to the capsid protein of the phage. After the phage infecting *E. coli*, single stranded DNA may be replicated in *E. coli*, and the phage may be reassembled and secreted into the culture medium, while the *E. coli* may not be lysed. The phage may be co-incubated with target antigens; and after the bound phages are isolated, amplification and purification may be then conducted so that great amounts of clones can be screened. The phage display technique can be found in the literature (Liu et al., 2004; the contents of which are hereby incorporated by reference in its entirety).

In another aspect, the present disclosure may include methods for producing a monoclonal antibody using a phage display method. Specifically, mRNA may be prepared from an animal, e.g., rabbits, rats, mice, guinea pigs, hamsters, goats, horses, chickens, sheep, and camelids (e.g., llamas), immunized by the method for immunizing an animal, whereupon cDNA may be prepared using the mRNA as a template, so that a single-chain antibody (scFv) gene encoding only an antibody variable region may be prepared. The gene may be cloned to a phagemid vector. *E. coli*, into which the phagemid vector is transduced, is infected with phage, so as to express the scFV antibody on the phage capsid. Screening of the scFv expressed in this way against an antigen protein or against a peptide-MHC complex may prepare a monoclonal scFV antibody specific to the antigen protein or the peptide-MHC complex. Herein, preparation of mRNA, preparation of cDNA, subcloning to phagemid or transduction to *E. coli*, phage infection, and screening of a monoclonal scFV antibody specific to an antigen protein or a peptide-MHC complex each may be performed by the known method. For example, subcloning of a scFV gene to a phagemid vector containing two elements consisting of a gene fragment encoding a leader sequence (signal sequence) and a phage capsid protein III and a replication origin of M13 and using of M13 phage as a phage can express a scFV antibody on the M13 phage. Further, a phage obtained by screening may be infected to a specific bacterium and cultured, so that a monoclonal antibody specific to an antigen protein may also be collected in large quantities from the culture. According to the method for producing a monoclonal antibody of the present disclosure, not only an scFV antibody but also an antibody fragment having no constant region, such as a Fab antibody fragment, may be prepared.

In another aspect, the present disclosure may include phage display libraries, in which the heavy and light chain variable regions of an antibody may be synthesized such that they include nearly all possible specificities.

In another aspect, the present disclosure may include generation of phage display libraries containing phage other than M13. Other bacteriophages, such as lambda phage, may also be useful in the method of the present disclosure. Lambda phage display libraries have been generated, which display peptides encoded by heterologous DNA on their surface (Sternberg et al., 1995; the content of which is hereby incorporated by reference in its entirety). Moreover, the method of the present disclosure may be extended to include viruses other than bacteriophage, such as eukaryotic viruses. Eukaryotic viruses may be generated that encode genes suitable for delivery to a mammal and that encode and display an antibody capable of targeting a specific cell type or tissue into which the gene is to be delivered. For example, retroviral vectors have been generated, which display functional antibody fragments (Russell et al., 1993; the content of which is hereby incorporated by reference in its entirety).

In another aspect, the present disclosure provides methods for producing a recombinant antibody specifically binding to MHC class I or II being complexed with a HLA restricted antigen (preferably a peptide consisting or consisting essentially of an amino acid sequence according to SEQ ID NO: 1 to SEQ ID NO: 216), the method may include immunizing a genetically engineered non-human mammal comprising cells expressing said MHC class I or II with a soluble form of a MHC class I or II molecule being complexed with said HLA restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said MHC class I or II being complexed with said HLA restricted antigen.

Antibodies of the invention are preferably administered to a subject in a pharmaceutically acceptable carrier. Typically, an appropriate amount of a pharmaceutically acceptable salt is used in the formulation to render the formulation isotonic. Examples of the pharmaceutically acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on for example the subject that will receive the antibody, the route of administration, the particular type of antibody used and other drugs being administered. A typical daily dosage of the antibody used alone might range from about 1 µg/kg to up to 100 mg/kg of body weight or more per day, depending on the factors mentioned above. Following administration of an antibody, preferably for treating acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of cancer.

It is a further aspect of the invention to provide a method for producing a soluble T cell receptor recognizing a specific peptide-MHC complex. Such soluble T cell receptors can be generated from specific T cell clones, and their affinity can be increased by mutagenesis targeting the complementarity-determining regions. For the purpose of T cell receptor selection, phage display can be used (US 2010/0113300, Liddy et al., 2012, the contents of which are incorporated by reference in their entirety). For the purpose of stabilization of T cell receptors during phage display and in case of practical use as drug, alpha and beta chains can be linked e.g. by non-native disulfide bonds, other covalent bonds (single chain T cell receptor), or by dimerization domains (Boulter et al., 2003; Card et al., 2004; Willcox et al., 1999, the contents of which are incorporated by reference in their entirety). The T cell receptor can be linked to toxins, drugs, cytokines (see for example US 2013/0115191, the contents of which are incorporated by reference in their entirety), and domains recruiting effector cells such as an anti-CD3 domain, etc., in order to execute particular functions on target cells. Moreover, it could be expressed in T cells used for adoptive transfer. Further information can be found in WO 2004/033685A1 and WO 2004/074322A1. A combination of soluble TCRs is described in WO 2012/056407A1. Further methods for the production are disclosed in WO 2013/057586A1, the contents of which are incorporated by reference in their entirety.

In addition, the peptides and/or the TCRs or antibodies or other binding molecules of the present invention can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more targets of a protein selected from the group consisting of the above-mentioned proteins, and the binding affinity ($K_d$) is <100 nM, more preferably <50 nM, more preferably <10 nM, more preferably <1 nM, more preferably <0.1 nM, more preferably <0.01 nM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

Another aspect of the present invention includes an in vitro method for producing activated T cells, the method comprising contacting in vitro T cells with peptide loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and *Drosophila* cells. TAP is the transporter associated with antigen processing.

The human peptide loading deficient cell line T2 is available from the American Type Culture Collection, 12301 Parklawn Drive, Rockville, Maryland 20852, USA under Catalogue No CRL 1992; the *Drosophila* cell line Schneider line 2 is available from the ATCC under Catalogue No CRL 19863; the mouse RMA-S cell line is described in Ljunggren et al. (Ljunggren and Karre, 1985, the contents of which are incorporated by reference in their entirety).

Preferably, before transfection the host cell expresses substantially no MHC class I molecules. It is also preferred that the stimulator cell expresses a molecule important for providing a co-stimulatory signal for T cells such as any of B7.1, B7.2, ICAM-1 and LFA3. The nucleic acid sequences of numerous MHC class I molecules and of the co-stimulator molecules are publicly available from the GenBank and EMBL databases.

In case of an MHC class I epitope being used as an antigen; the T cells are CD8-positive T cells.

If an antigen-presenting cell is transfected to express such an epitope, preferably the cell comprises an expression vector capable of expressing a peptide containing SEQ ID NO: 1 to SEQ ID NO: 216, or a variant amino acid sequence thereof.

A number of other methods may be used for generating T cells in vitro. For example, autologous tumor-infiltrating lymphocytes can be used in the generation of CTL. Plebanski et al. (Plebanski et al., 1995) made use of autologous peripheral blood lymphocytes (PLBs) in the preparation of T cells. Furthermore, the production of autologous T cells by pulsing dendritic cells with peptide or polypeptide, or via infection with recombinant virus is possible. Also, B cells can be used in the production of autologous T cells. In addition, macrophages pulsed with peptide or polypeptide, or infected with recombinant virus, may be used in the preparation of autologous T cells. S. Walter et al. (Walter et al., 2003, the contents of which are incorporated by reference in their entirety) describe the in vitro priming of T cells by using artificial antigen presenting cells (aAPCs), which is also a suitable way for generating T cells against the peptide of choice. In the present invention, aAPCs were generated by the coupling of preformed MHC-peptide complexes to the surface of polystyrene particles (microbeads) by biotin: streptavidin biochemistry. This system permits the exact control of the MHC density on aAPCs, which allows to selectively elicit high- or low-avidity antigen specific T cell responses with high efficiency from blood samples. Apart from MHC-peptide complexes, aAPCs should carry other proteins with co-stimulatory activity like anti-CD28 antibodies coupled to their surface. Furthermore, such aAPC-based systems often require the addition of appropriate soluble factors, e. g. cytokines, like interleukin-12.

Allogeneic cells may also be used in the preparation of T cells and a method is described in detail in WO 97/26328, incorporated herein by reference in its entirety. For example, in addition to *Drosophila* cells and T2 cells, other cells may be used to present antigens such as CHO cells, baculovirus-infected insect cells, bacteria, yeast, and vaccinia-infected target cells. In addition, plant viruses may be used see for example Porta et al. (Porta et al., 1994, the content of which is incorporated by reference in its entirety) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO: 216.

Preferably, the T cell recognizes the cell by interacting through its TCR with the HLA-peptide complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e., they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for and detected.

In vivo, the target cells for the CD8-positive T cells according to the present invention can be cells of the tumor (which sometimes express MHC class II) and/or stromal cells surrounding the tumor (which sometimes also express MHC class II) (Dengjel et al., 2006).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is overexpressed compared to levels of expression in normal tissues or that the gene is silent in the tissue from which the tumor is derived but in the tumor it is expressed. By "overexpressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Several reviews can be found (Gattinoni et al., 2006; Morgan et al., 2006, the contents of which are incorporated by reference in their entirety).

Another aspect of the present invention includes the use of the peptides complexed with MHC to generate a T cell receptor whose nucleic acid is cloned and is introduced into a host cell, preferably a T cell. This engineered T cell can then be transferred to a patient for therapy of cancer.

Any molecule of the invention, i.e., the peptide, nucleic acid, antibody, expression vector, cell, activated T cell, T cell receptor or the nucleic acid encoding it, is useful for the treatment of disorders, characterized by cells escaping an immune response. Therefore, any molecule of the present invention may be used as medicament or in the manufacture of a medicament. The molecule may be used by itself or combined with other molecule(s) of the invention or (a) known molecule(s).

Kits of the present invention preferably comprise a lyophilized formulation of the present invention in a suitable container and instructions for its reconstitution and/or use. Suitable containers include for example bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have a distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably, the administration is s.c., and most preferably i.d. administration by infusion pump.

Since the peptides of the invention were isolated from acute myeloid leukemia, breast cancer, cholangiocellular carcinoma, chronic lymphocytic leukemia, colorectal cancer, gallbladder cancer, glioblastoma, gastric cancer, gastroesophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer, the medicament of the invention is preferably used to treat acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides for a personalized peptide-based vaccine are selected, the vaccine is produced. The vaccine preferably is a liquid formulation consisting of the individual peptides dissolved in between 20-40% DMSO, preferably about 30-35% DMSO, such as about 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml/peptide. The mixed solution is then diluted 1:3 with water for injection to achieve a concentration of 0.826 mg/ml/peptide in 33% DMSO. The diluted solution is filtered through a 0.22 µm sterile filter. The final bulk solution is obtained.

The final bulk solution is filled into vials and stored at −20° C. until use. One vial contains 700 µL solution, containing 0.578 mg of each peptide. Of this, 500 µL (approx. 400 µg per peptide) will be applied for intradermal injection.

In addition to being useful for treating cancer, the peptides of the present invention are also useful as diagnostics. Since the peptides were generated from acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer cells and since it was determined that these peptides are not or at lower levels present in normal tissues, these peptides can be used to diagnose the presence of a cancer.

The presence of claimed peptides on tissue biopsies in blood samples can assist a pathologist in diagnosis of cancer. Detection of certain peptides by means of antibodies, mass spectrometry or other methods known in the art can tell the pathologist that the tissue sample is malignant or inflamed or generally diseased, or can be used as a biomarker for acute myeloid leukemia, breast cancer, cholangiocellular carcinoma, chronic lymphocytic leukemia, colorectal cancer, gallbladder cancer, glioblastoma, gastric cancer, gastroesophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected or malignant cells escape immuno-surveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate response markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The present invention will now be described in the following examples which describe preferred embodiments thereof, and with reference to the accompanying figures, nevertheless, without being limited thereto. For the purposes of the present invention, all references as cited herein are incorporated by reference in their entireties.

Further, note that experimental data and figures may only be disclosed herein for a selected set of peptides as claimed. Although for all peptides disclosed and claimed herein, complete data sets have been generated and can be made available upon request, applicant has decided to not incorporate herein all these complete date sets, because this would go beyond a manageable scope of this application text.

BRIEF DESCRIPTION OF THE DRAWINGS

If the peptide has been detected on a sample but could not be quantified for technical reasons, the sample is included in this representation of detection frequency, but no dot is shown in the upper part of the figure. Tissues (from left to right): Normal samples: adipose (adipose tissue); adrenal gl (adrenal gland); bile duct; bladder; bloodcells; bloodvess (blood vessels); bone marrow; brain; breast; esoph (esophagus); eye; gall bl (gallbladder); nead&neck; heart; intest. la (large intestine); intest. sm (small intestine); kidney; liver; lung; lymph nodes; nerve cent (central nerve); nerve periph (peripheral nerve); ovary; pancreas; parathyr (parathyroid gland); perit (peritoneum); pituit (pituitary); placenta; pleura; prostate; skel. mus (skeletal muscle); skin; spinal cord; spleen; stomach; testis; thymus; thyroid; trachea; ureter; uterus. Tumor samples: AML (acute myeloid leukemia); BRCA (breast cancer); CCC (cholangiocellular carcinoma); CLL (chronic lymphocytic leukemia); CRC (colorectal cancer); GBC (gallbladder cancer); GBM (glioblastoma); GC (gastric cancer); GEJC (gastro-esophageal junction cancer); HCC (hepatocellular carcinoma); HNSCC (head and neck squamous cell carcinoma); MEL (melanoma); NHL (non-Hodgkin lymphoma); NSCLCadeno (non-small cell lung cancer adenocarcinoma); NSCLCother (NSCLC samples that could not unambiguously be assigned to NSCLCadeno or NSCLCsquam); NSCLCsquam (squamous cell non-small cell lung cancer); OC (ovarian cancer); OSCAR (esophageal cancer); PACA (pancreatic cancer); PRCA (prostate cancer); RCC (renal cell carcinoma); SCLC (small cell lung cancer); UBC (urinary bladder carcinoma); UEC (uterine endometrial cancer). FIGS. 1A-1 and 1A-2) Peptide: AILAPPAILK (SEQ ID NO: 1), FIGS. 1B-1 and 1B-2) Peptide: GTVFVLLSK (SEQ ID NO: 2), FIGS. 1C-1 and 1C-2) Peptide: VYIASSFKI (SEQ ID NO: 3), FIGS. 1D-1 and 1D-2) Peptide: IQAPALLKV (SEQ ID NO: 4), FIGS. 1E-1 and 1E-2) Peptide: METADRPEW (SEQ ID NO: 5).

FIGS. 2A-1 through 2E-2 show exemplary expression profile of source genes of the present invention that are overexpressed in different cancer samples. Tumor (black dots) and normal (grey dots) samples are grouped according to organ of origin. Box-and-whisker plots represent median value, 25th and 75th percentile (box) plus whiskers that extend to the lowest data point still within 1.5 interquartile range (IQR) of the lower quartile and the highest data point still within 1.5 IQR of the upper quartile. Tissues (from left to right): Normal samples: adipose (adipose tissue); adrenal gl (adrenal gland); bile duct; bladder; bloodcells; bloodvess (blood vessels); bone marrow; brain; breast; esoph (esophagus); eye; gall bl (gallbladder); nead&neck; heart; intest. la (large intestine); intest. sm (small intestine); kidney; liver; lung; lymph nodes; nerve periph (peripheral nerve); ovary; pancreas; parathyr (parathyroid gland); perit (peritoneum); pituit (pituitary); placenta; pleura; prostate; skel. mus (skeletal muscle); skin; spinal cord; spleen; stomach; testis; thymus; thyroid; trachea; ureter; uterus. Tumor samples: AML (acute myeloid leukemia); BRCA (breast cancer); CCC (cholangiocellular carcinoma); CLL (chronic lymphocytic leukemia); CRC (colorectal cancer); GBC (gallbladder cancer); GBM (glioblastoma); GC (gastric cancer); GEJC (gastro-esophageal junction cancer); HCC (hepatocellular carcinoma); HNSCC (head and neck squamous cell carcinoma); MEL (melanoma); NHL (non-Hodgkin lymphoma); NSCLCadeno (non-small cell lung cancer adenocarcinoma); NSCLCother (NSCLC samples that could not unambiguously be assigned to NSCLCadeno or NSCLCsquam); NSCLCsquam (squamous cell non-small cell lung cancer); OC (ovarian cancer); OSCAR (esophageal cancer); PACA (pancreatic cancer); PRCA (prostate cancer); RCC (renal cell carcinoma); SCLC (small cell lung cancer); UBC (urinary bladder carcinoma); UEC (uterine endometrial cancer). FIGS. 2A-1 and 2A-2) Peptide: SHSLPAFTL (SEQ ID NO: 6), FIGS. 2B-1 and 2B-2) Peptide: IYIPTNSIYKF (SEQ ID NO: 7), FIGS. 2C-1 and 2C-2) Peptide: VIYNQTLMK (SEQ ID NO: 8), FIGS. 2D-1 and 2D-2) Peptide: LLGVVSHSV (SEQ ID NO: 9), FIGS. 2E-1 and 2E-2) Peptide: ILMILQPQL (SEQ ID NO: 10).

EXAMPLES

Example 1

Figures 1, 1A, 2:
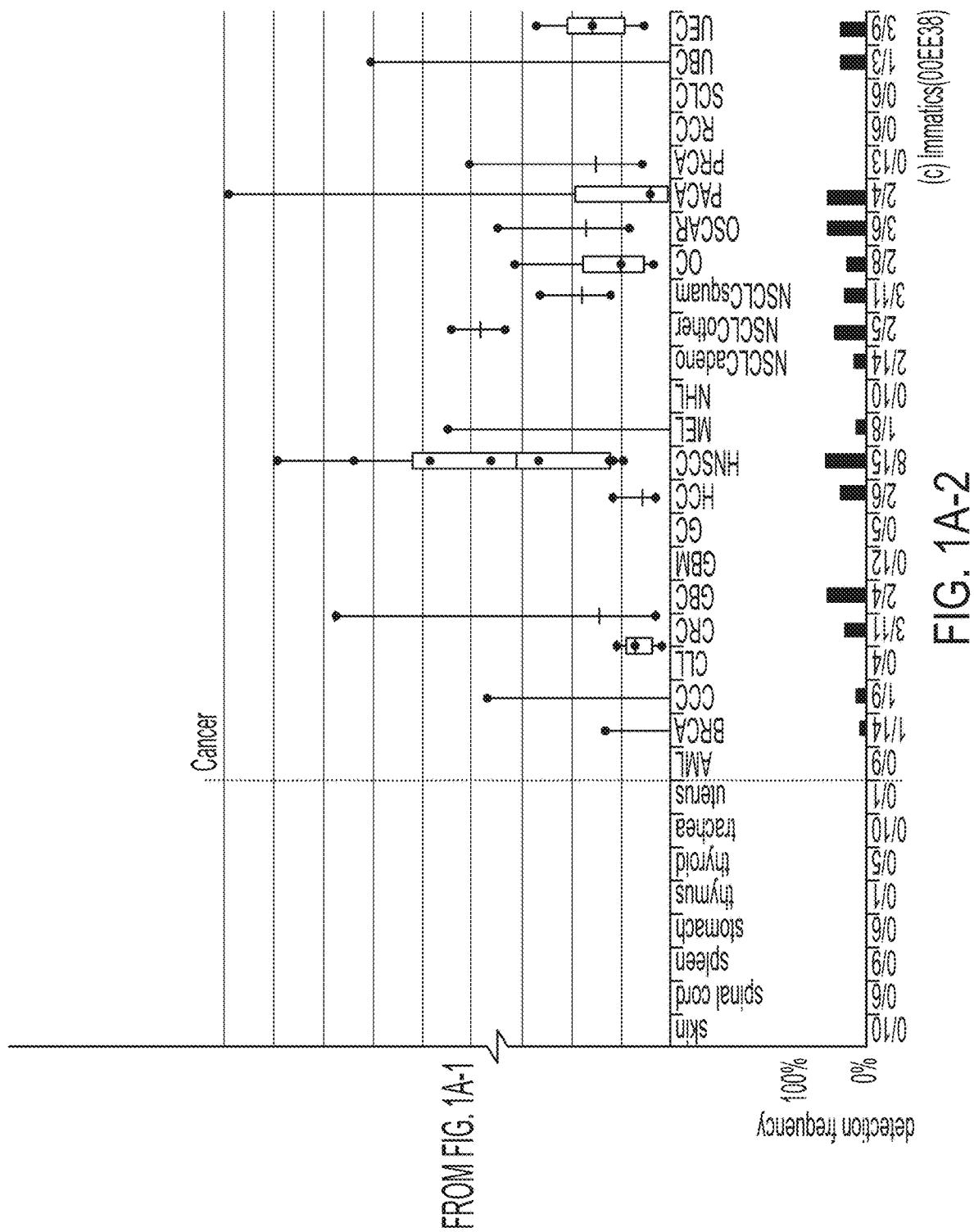
FIGS. 1A-1 through 1E-2 show the over-presentation of various peptides in different cancer tissues compared to normal tissues. Upper part: Median MS signal intensities from technical replicate measurements are plotted as dots for single normal (grey dots, left part of figure) and tumor samples (black dots, right part of figure) of the respective HLA allotype on which the peptide was detected. Boxes display median, 25th and 75th percentile of normalized signal intensities, while whiskers extend to the lowest data point still within 1.5 interquartile range (IQR) of the lower quartile, and the highest data point still within 1.5 IQR of the upper quartile. Lower part: The relative peptide detection frequency in every organ is shown as spine plot. Numbers below the panel indicate number of samples on which the peptide was detected out of the total number of samples analyzed for each organ (N>750 for HLA-A*02 positive normal samples, N>210 for HLA-A*03 positive normal samples, N>180 HLA-A*24 normal samples, and N>210 HLA-B*44 normal samples) or tumor indication (N>675 for HLA-A*02 positive cancer samples, N>180 for HLA-A*03 positive cancer samples, N>330 HLA-A*24 positive cancer samples and N>210 HLA-B*44 positive cancer samples).
Figures 1, 1B:
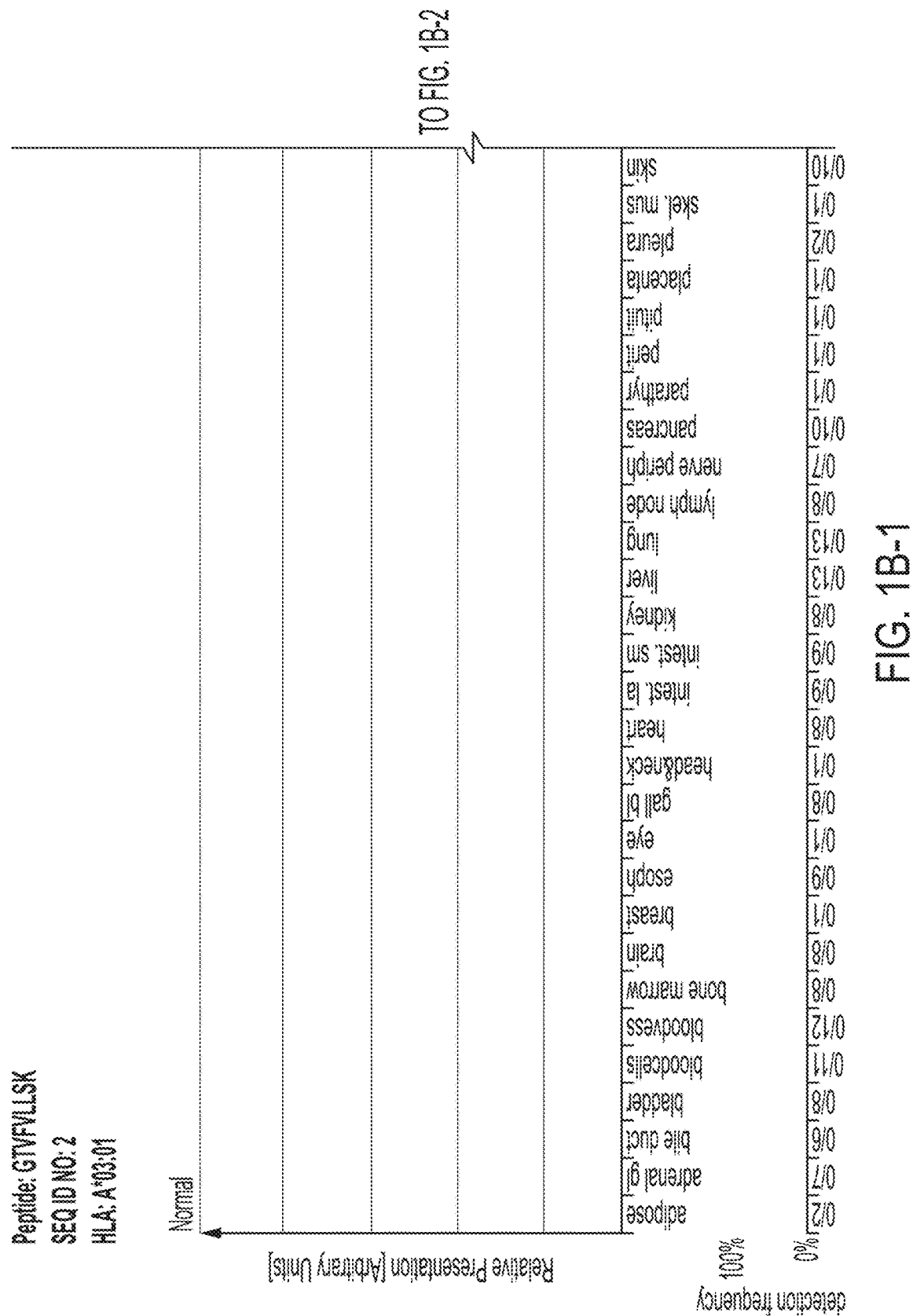
Figures 1, 1B, 2:
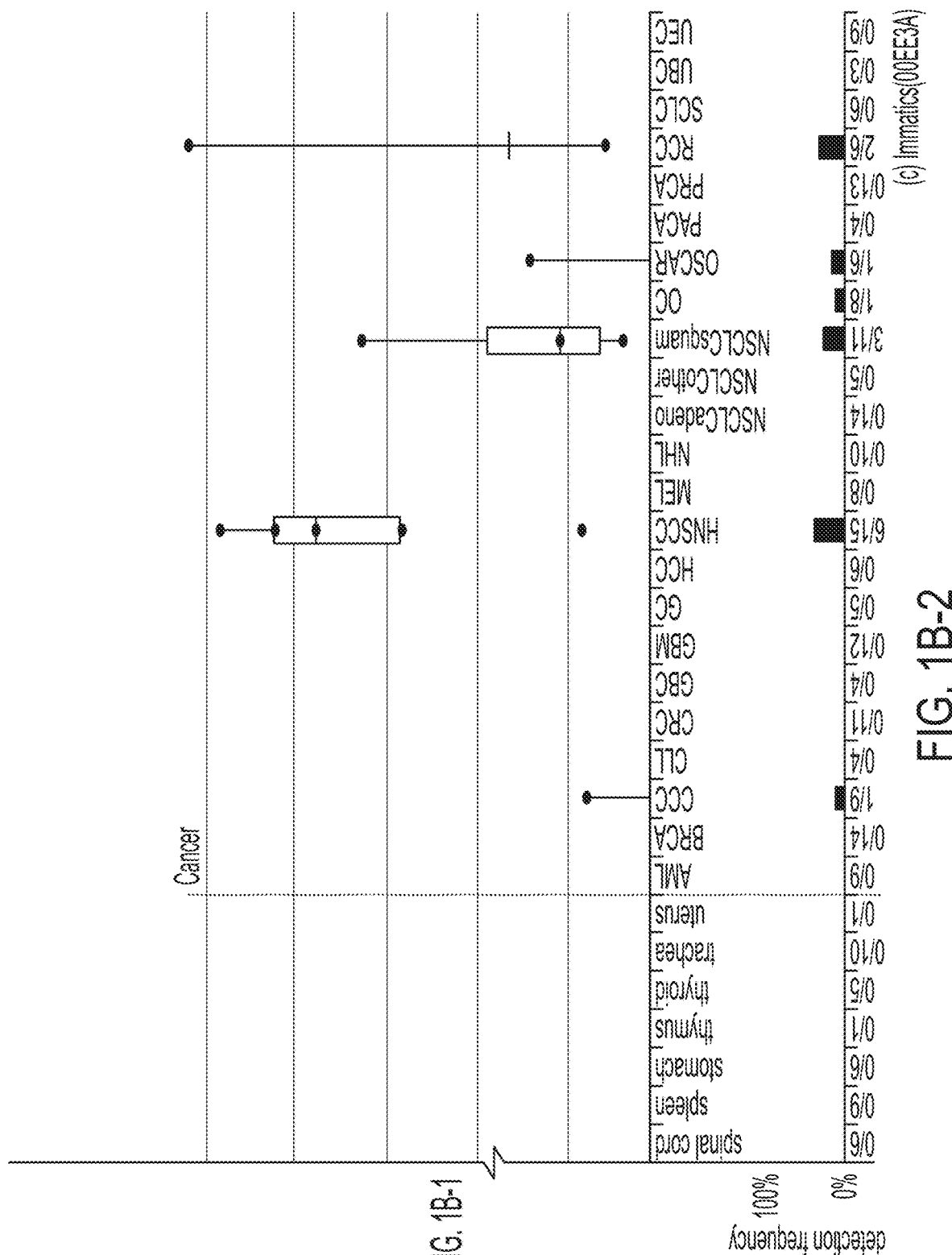
Figures 1, 1C:
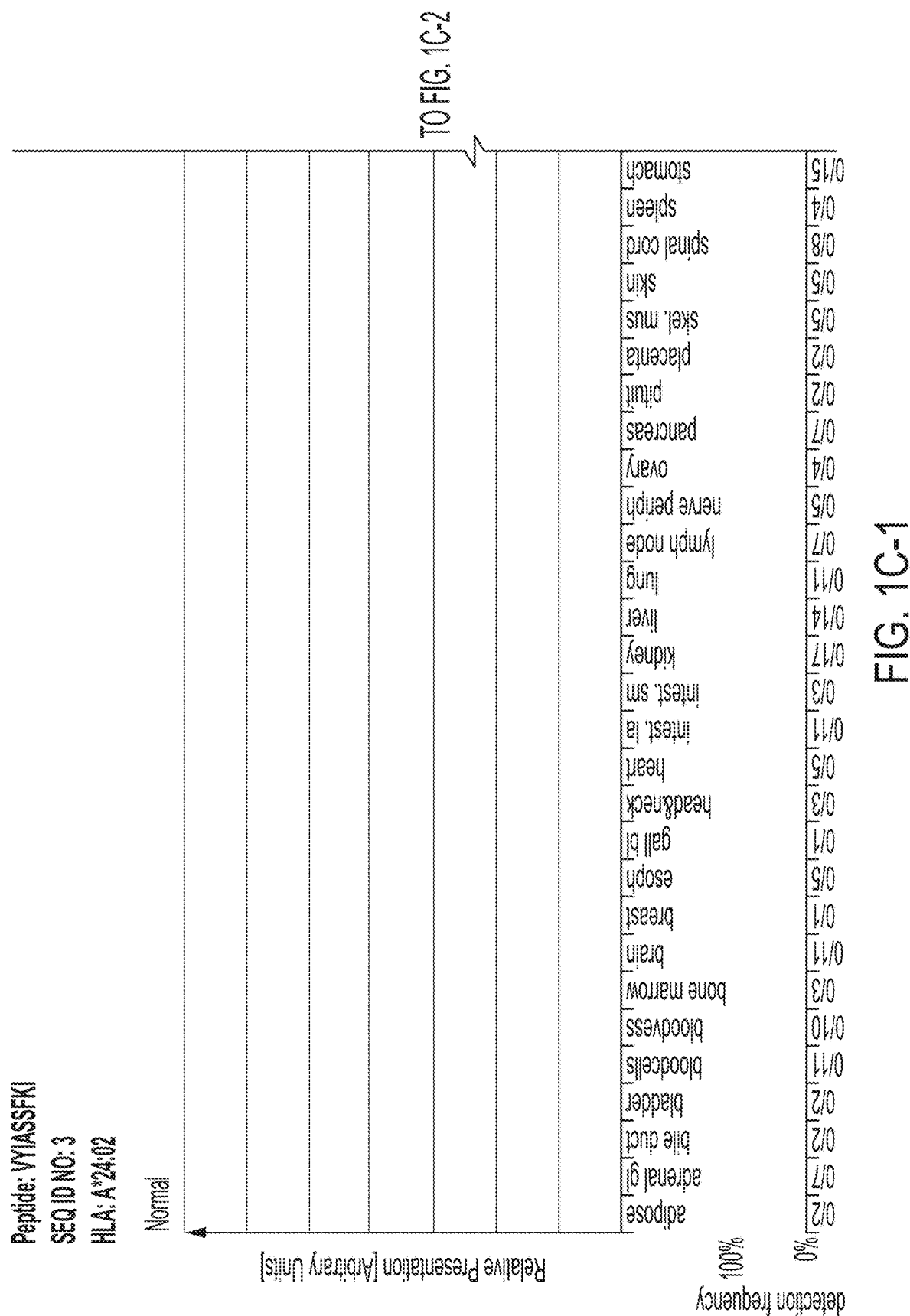
Figures 1, 1C, 2:
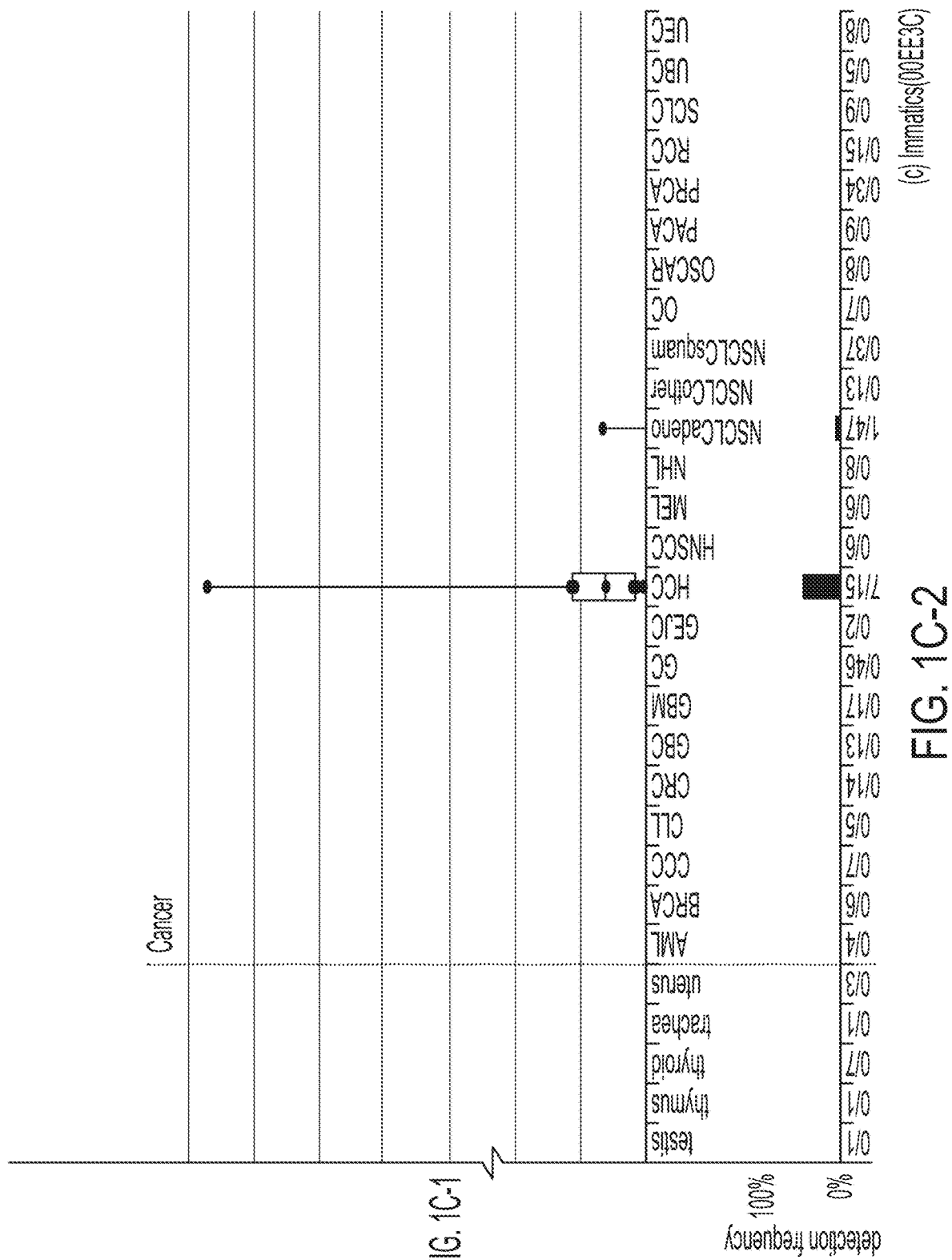
Figures 1, 1D:
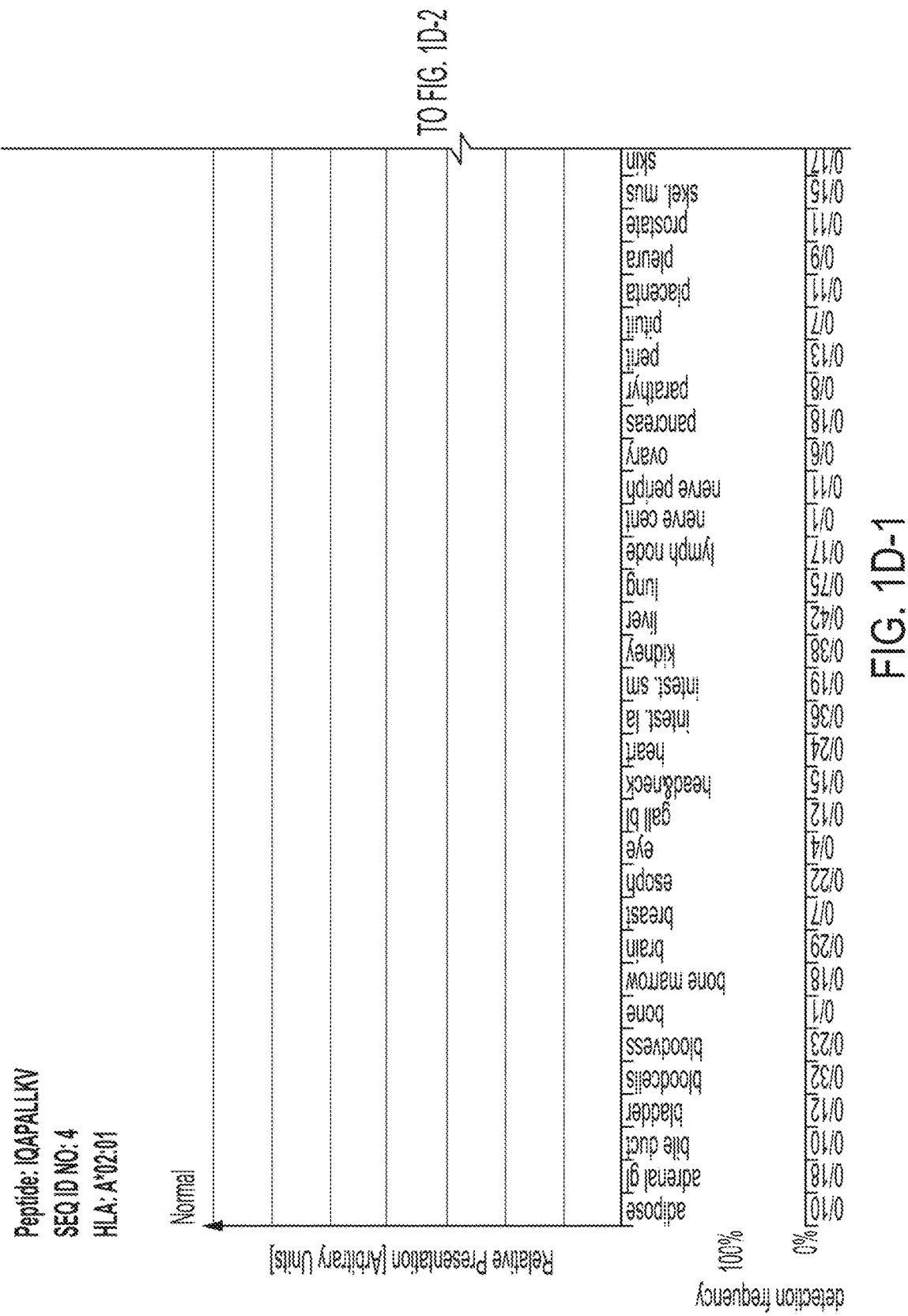
Figures 1, 1D, 2:
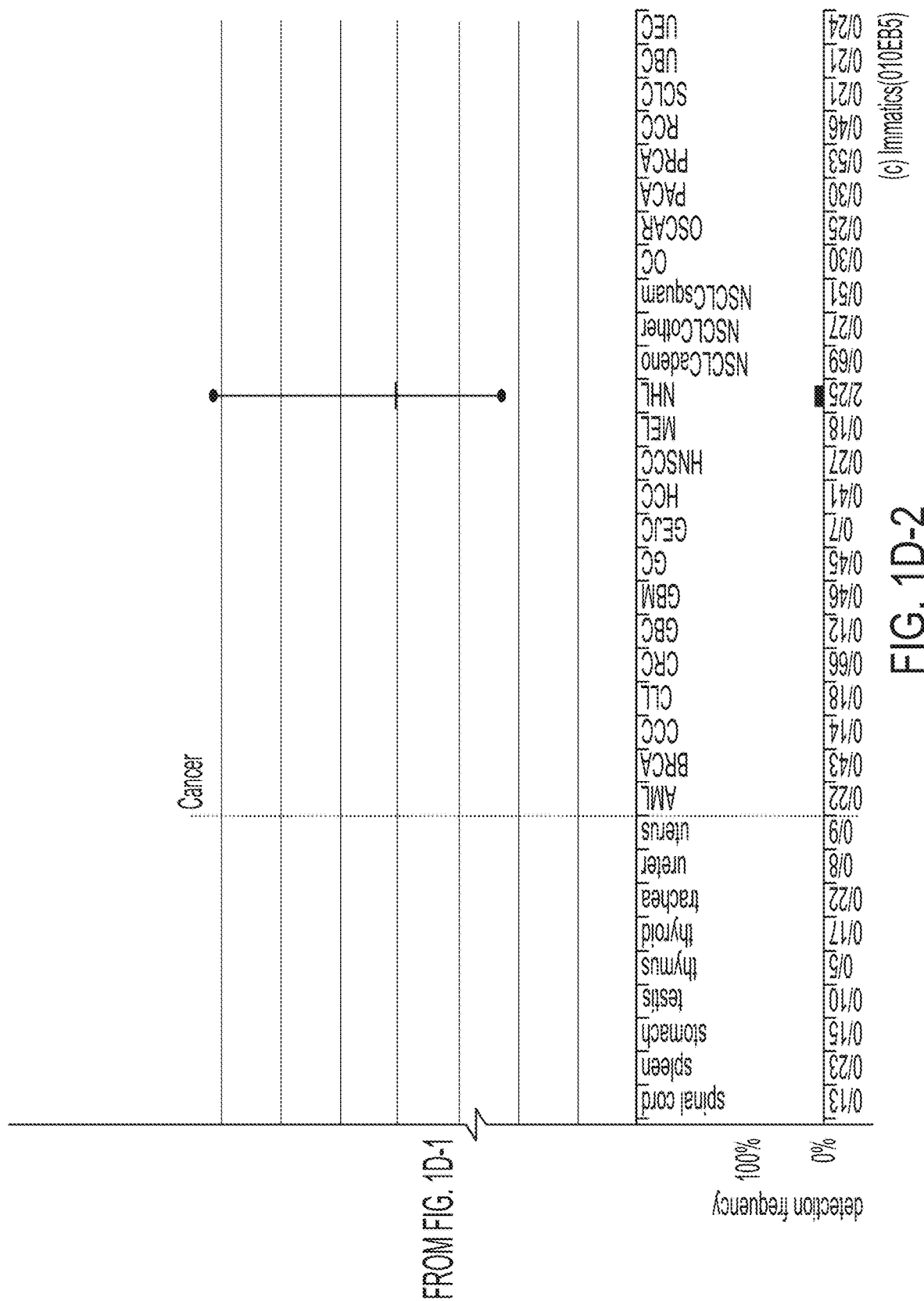

Identification and Quantitation of Tumor Associated Peptides Presented on the Cell Surface Tissue Samples Patients' tissues were obtained from:

BioIVT (Detroit, MI, USA & Royston, Herts, UK); BioOptions Inc. (Brea, CA, USA); BioServe (Beltsville, MD, USA); Capital BioScience Inc. (Rockville, MD, USA); Conversant Bio (Huntsville, AL, USA); Cureline Inc. (Brisbane, CA, USA); DxBiosamples (San Diego, CA, USA); Geneticist Inc. (Glendale, CA, USA); Indivumed GmbH (Hamburg, Germany); Kyoto Prefectural University of Medicine (KPUM) (Kyoto, Japan); Osaka City University (OCU) (Osaka, Japan); ProteoGenex Inc. (Culver City, CA, USA); Tissue Solutions Ltd (Glasgow, UK); Universität Bonn (Bonn, Germany); Asklepios Clinic St. Georg (Hamburg, Germany); Val d'Hebron University Hospital (Barcelona, Spain); Center for cancer immune therapy (CCIT), Herlev Hospital (Herlev, Denmark); Leiden University Medical Center (LUMC) (Leiden, Netherlands); Istituto Nazionale Tumori "Pascale", Molecular Biology and Viral Oncology Unit (Naples, Italy); Stanford Cancer Center (Palo Alto, CA, USA); University Hospital Geneva (Geneva, Switzerland); University Hospital Heidelberg (Heidelberg, Germany); University Hospital Munich (Munich, Germany); University Hospital Tuebingen (Tuebingen, Germany).

Written informed consents of all patients had been given before surgery or autopsy. Tissues were shock-frozen immediately after excision and stored until isolation of TUMAPs at −70° C. or below.

Isolation of HLA Peptides from Tissue Samples

HLA peptide pools from shock-frozen tissue samples were obtained by immune precipitation from solid tissues according to a slightly modified protocol (Falk et al., 1991; Seeger et al., 1999) using the HLA-A*02 specific antibody BB7.2, the HLA-A, -B, -C specific antibody w6/32, the HLA-DR specific antibody L243 and the HLA-DP specific antibody B7/21, CNBr-activated sepharose, acid treatment, and ultrafiltration.

Table 7 shows the peptides and the HLA allotypes—from the group consisting of HLA-A*01:01, HLA-A*02:01, HLA-A*03:01, HLA-A*24:02, HLA-B*07:02, HLA-B*08:01 and HLA-B*44:02-they bind to. However, due to similarities in binding pattern such as the relevant anchoring positions some peptides bind to more than one allele, such an overlap is most likely, but not limited to, HLA-A*01 binding peptides also binding to HLA-B*15, HLA-A*03 binding peptides also binding to HLA-A*11, HLA-B*07 binding peptides also binding to HLA-B*35 and HLA-B*51.

TABLE 7

HLA alleles the peptides according to the invention bind to.

| SEQ ID NO | Sequence | Binders |
|---|---|---|
| 1 | AILAPPAILK | HLA-A*03:01 |
| 2 | GTVFVLLSK | HLA-A*03:01 |
| 3 | VYIASSFKI | HLA-A*24:02 |
| 4 | IQAPALLKV | HLA-A*02:01 |
| 5 | METADRPEW | HLA-B*44:02 |
| 6 | SHSLPAFTL | HLA-A*24:02 |
| 7 | IYIPTNSIYKF | HLA-A*24:02 |
| 8 | VIYNQTLMK | HLA-A*03:01 |
| 9 | LLGVVSHSV | HLA-A*02:01 |
| 10 | ILMILQPQL | HLA-A*02:01 |
| 11 | TEIGTVIKLF | HLA-B*44:02 |

TABLE 7-continued

HLA alleles the peptides according to the invention bind to.

| SEQ ID NO | Sequence | Binders |
|---|---|---|
| 12 | RLQEGLAAL | HLA-A*02:01 |
| 13 | LYDTVTHTF | HLA-A*24:02 |
| 14 | ILAPPQRISF | HLA-A*24:02 |
| 15 | SPVETRSLL | HLA-B*07:02 |
| 16 | NFHTLAQQLLF | HLA-A*24:02 |
| 17 | MVNWSLTNK | HLA-A*03:01 |
| 18 | SLSKLVATV | HLA-A*02:01 |
| 19 | RILEVVRQPK | HLA-A*03:01 |
| 20 | ILAPPAILK | HLA-A*03:01 |
| 21 | MLSAQFILK | HLA-A*03:01 |
| 22 | RVIEVVMNSK | HLA-A*03:01 |
| 23 | AETKQFWSA | HLA-B*44:02 |
| 24 | LIYIPTNSIYK | HLA-A*03:01 |
| 25 | GVCSTLTIK | HLA-A*03:01 |
| 26 | ETNTIEFIY | HLA-A*01:01 |
| 27 | SQAKQITIW | HLA-B*44:02 |
| 28 | ATLQAVTLYKK | HLA-A*03:01 |
| 29 | GTFIAPVMK | HLA-A*03:01 |
| 30 | SLKSSILFL | HLA-A*02:01 |
| 31 | VFLLLPYPRF | HLA-A*24:02 |
| 32 | TAMTTLMAF | HLA-B*08:01 |
| 33 | AYIPFPPLI | HLA-A*24:02 |
| 34 | LLFKGLMWK | HLA-A*03:01 |
| 35 | SLATAISAK | HLA-A*03:01 |
| 36 | KEIEAQEAA | HLA-B*44:02 |
| 37 | RLYSGSSFLY | HLA-A*03:01 |
| 38 | AVVSHFILY | HLA-A*03:01 |
| 39 | RELGVGIAL | HLA-B*44:02 |
| 40 | LYQTTIELF | HLA-A*24:02 |
| 41 | APQPRSLAA | HLA-B*07:02 |
| 42 | LLSRGILIL | HLA-A*02:01 |
| 43 | VFIPSVINL | HLA-A*24:02 |
| 44 | SLFPYFLNK | HLA-A*03:01 |
| 45 | SLFPISLTV | HLA-A*02:01 |
| 46 | GESIYLLVRKW | HLA-B*44:02 |
| 47 | LYIFTTRPF | HLA-A*24:02 |
| 48 | TEMSVSALY | HLA-B*44:02 |
| 49 | IYFHLNNWTI | HLA-A*24:02 |
| 50 | KTIDLVIVR | HLA-A*03:01 |
| 51 | SVFSLVHLFDK | HLA-A*03:01 |
| 52 | SPLPHLGPL | HLA-B*07:02 |
| 53 | TTLENLPQK | HLA-A*03:01 |
| 54 | ASSPVILLL | HLA-A*01:01 |
| 55 | SPVSASWIL | HLA-B*07:02 |
| 56 | DVDIHKDLY | HLA-A*01:01 |
| 57 | IIIDRILLL | HLA-A*02:01 |
| 58 | REQLDGATL | HLA-B*44:02 |
| 59 | AVDLGVLEL | HLA-B*07:02 |
| 60 | VSPDEVLALW | HLA-A*01:01 |
| 61 | GLIAFAIFK | HLA-A*03:01 |
| 62 | SFSLLLPYL | HLA-A*24:02 |
| 63 | MPANFETIGF | HLA-B*07:02 |
| 64 | LPTRSLPAF | HLA-B*07:02 |
| 65 | NSDLFYLLL | HLA-A*01:01 |
| 66 | RPLILIRI | HLA-B*07:02 |
| 67 | GRFWLPFNF | HLA-A*24:02 |
| 68 | TVDKGELLY | HLA-A*01:01 |
| 69 | KYPTIICGF | HLA-A*24:02 |
| 70 | LIAGLIFLK | HLA-A*03:01 |
| 71 | LIDSLLLLL | HLA-A*01:01 |
| 72 | GSCSFALSR | HLA-A*03:01 |
| 73 | NQKGLISL | HLA-B*08:01 |
| 74 | TLNVLITL | HLA-A*02:01 |
| 75 | TTAAVYILK | HLA-A*03:01 |
| 76 | VQSGVPSRF | HLA-A*24:02 |
| 77 | YPDVPIGQL | HLA-B*07:02 |
| 78 | TPSHSTPSF | HLA-B*07:02 |
| 79 | SLFRLSISF | HLA-A*24:02 |
| 80 | IFDLSDPRF | HLA-A*24:02 |
| 81 | KLIAGLIFLK | HLA-A*03:01 |
| 82 | VLQSLQHEL | HLA-A*02:01 |
| 83 | EAAPNIMHY | HLA-A*01:01 |
| 84 | KEFAFLEHSL | HLA-B*44:02 |
| 85 | LPHPVNSGL | HLA-B*07:02 |
| 86 | VANDRLSFL | HLA-B*08:01 |

TABLE 7-continued

HLA alleles the peptides according to the invention bind to.

| SEQ ID NO | Sequence | Binders |
|---|---|---|
| 87 | LHLNPGLSF | HLA-A*24:02 |
| 88 | KVGAVVHLK | HLA-A*03:01 |
| 89 | SPSSPLLLLA | HLA-B*07:02 |
| 90 | LALLGAPPPK | HLA-A*03:01 |
| 91 | RIVTYIVAK | HLA-A*03:01 |
| 92 | LNFSDVFLY | HLA-A*01:01 |
| 93 | SPIGLSLIL | HLA-B*07:02 |
| 94 | AVFLGNPSNQK | HLA-A*03:01 |
| 95 | YAFRNQTL | HLA-B*08:01 |
| 96 | HPRESLNMLVAF | HLA-B*07:02 |
| 97 | ALIVLHLSL | HLA-A*02:01 |
| 98 | FSEIFQDFL | HLA-A*01:01 |
| 99 | RADEEQASF | HLA-A*01:01 |
| 100 | SPAPSLARFLSL | HLA-B*07:02 |
| 101 | ATNSFLLIK | HLA-A*03:01 |
| 102 | FLLLEKGGEL | HLA-A*02:01 |
| 103 | RPWLSSPTGL | HLA-B*07:02 |
| 104 | GSLQTLPPK | HLA-A*03:01 |
| 105 | LVFESVVAA | HLA-A*02:01 |
| 106 | GLLDAFLRL | HLA-A*02:01 |
| 107 | SVISVLTTPK | HLA-A*03:01 |
| 108 | SLQESLPNA | HLA-A*02:01 |
| 109 | MPKLFLTAC | HLA-B*07:02 |
| 110 | APSLARFLSL | HLA-B*07:02 |
| 111 | RPIWDVRSA | HLA-B*07:02 |
| 112 | ETYGTFVLR | HLA-A*03:01 |
| 113 | ALGPMAFRV | HLA-A*02:01 |
| 114 | VPHHLLSSV | HLA-B*07:02 |
| 115 | LWEEKPVCL | HLA-A*24:02 |
| 116 | IYLTKSNLVNM | HLA-A*24:02 |
| 117 | GEAAAARPV | HLA-B*44:02 |
| 118 | RLLRLIPIL | HLA-A*02:01 |
| 119 | VLHGLLFTL | HLA-A*02:01 |
| 120 | APGPRSQGL | HLA-B*07:02 |
| 121 | ILVTAWKGV | HLA-A*02:01 |
| 122 | FTQKINSTW | HLA-A*01:01 |
| 123 | TYLESSVRI | HLA-A*24:02 |
| 124 | SPSSNSREL | HLA-B*07:02 |
| 125 | ALAQGANLK | HLA-A*03:01 |
| 126 | NPELLVILL | HLA-B*07:02 |
| 127 | TVATQVATSK | HLA-A*03:01 |
| 128 | MTFVPLLAR | HLA-A*03:01 |
| 129 | IPISIFKMA | HLA-B*07:02 |
| 130 | ITPDSIPSV | HLA-A*02:01 |
| 131 | TILAKQNVL | HLA-B*08:01 |
| 132 | LYLETRSEF | HLA-A*24:02 |
| 133 | KFPPSASEF | HLA-A*24:02 |
| 134 | MPCTTILRI | HLA-B*07:02 |
| 135 | SADTAELLL | HLA-A*01:01 |
| 136 | YSSEIWDLY | HLA-A*01:01 |
| 137 | MPIQVLKGL | HLA-B*07:02 |
| 138 | RTLPLEGSPK | HLA-A*03:01 |
| 139 | EEGRIITKW | HLA-B*44:02 |
| 140 | QPAPQPLL | HLA-B*07:02 |
| 141 | REVAGASAL | HLA-B*44:02 |
| 142 | YMLEMDNSMKI | HLA-A*02:01 |
| 143 | AVLGALLRH | HLA-A*03:01 |
| 144 | IIVPSFYK | HLA-A*03:01 |
| 145 | HLFSVLSAI | HLA-A*02:01 |
| 146 | KVLVDFLLK | HLA-A*03:01 |
| 147 | VEAPHLPSF | HLA-B*44:02 |
| 148 | SVYMATTLK | HLA-A*03:01 |
| 149 | SMNSKALRWK | HLA-A*03:01 |
| 150 | IVFLLQQGEK | HLA-A*03:01 |
| 151 | AVFVNWEQTKK | HLA-A*03:01 |
| 152 | KIMEILNLK | HLA-A*03:01 |
| 153 | ALNLSRLTV | HLA-A*02:01 |
| 154 | TVTSAIVNR | HLA-A*03:01 |
| 155 | MPWVLMSPF | HLA-B*07:02 |
| 156 | SLRVPSPAL | HLA-B*07:02 |
| 157 | APLRAGWAA | HLA-B*07:02 |
| 158 | FQLSGPVTF | HLA-A*24:02 |
| 159 | ASAIPAGAK | HLA-A*03:01 |
| 160 | EYLGSENVF | HLA-A*24:02 |
| 161 | ILAASFQAR | HLA-A*03:01 |

TABLE 7-continued

HLA alleles the peptides according to the invention bind to.

| SEQ ID NO | Sequence | Binders |
|---|---|---|
| 162 | LPVHGPLPLLL | HLA-B*07:02 |
| 163 | LWALAIPSL | HLA-A*24:02 |
| 164 | SHSSPTVSF | HLA-A*24:02 |
| 165 | FYNPRPPLI | HLA-A*24:02 |
| 166 | VIFLHQPPK | HLA-A*03:01 |
| 167 | FALGPIIKQL | HLA-A*02:01 |
| 168 | AEGPDHHSL | HLA-B*44:02 |
| 169 | RPQGVGPAA | HLA-B*07:02 |
| 170 | LLDSWNILI | HLA-A*02:01 |
| 171 | NVSFEVSLLY | HLA-A*01:01 |
| 172 | LLYKTLIIL | HLA-A*02:01 |
| 173 | IFTGRNAYF | HLA-A*24:02 |
| 174 | LSGPVTFLR | HLA-A*03:01 |
| 175 | MPFLKVPPL | HLA-B*07:02 |
| 176 | AFLLSLISL | HLA-A*24:02 |
| 177 | SYLKDHLSL | HLA-A*24:02 |
| 178 | SLFGGLFTR | HLA-A*03:01 |
| 179 | MIFSGVFLR | HLA-A*03:01 |
| 180 | QYLTYYPSF | HLA-A*24:02 |
| 181 | FDLNIGSAY | HLA-B*44:02 |
| 182 | RPSLPCRSF | HLA-B*07:02 |
| 183 | VFVISGSHLF | HLA-A*24:02 |
| 184 | VVHGGMSIF | HLA-B*07:02 |
| 185 | MPAFLSRASAL | HLA-B*07:02 |
| 186 | SQIKSPVVF | HLA-A*24:02 |
| 187 | RLCPAAPTGK | HLA-A*03:01 |
| 188 | KLPFFTNFL | HLA-A*02:01 |
| 189 | IWRALGSLF | HLA-A*24:02 |
| 190 | STQSSLLYLK | HLA-A*03:01 |
| 191 | APLLPGPAA | HLA-B*07:02 |
| 192 | IPLHFSTAF | HLA-B*07:02 |
| 193 | ILQLITVNR | HLA-A*03:01 |
| 194 | VLYPSHSSF | HLA-A*24:02 |
| 195 | AWNESSAWLL | HLA-A*24:02 |
| 196 | NSENLLVY | HLA-A*01:01 |
| 197 | HHTQLVFVF | HLA-A*24:02 |
| 198 | MTYQQPFSNR | HLA-A*03:01 |
| 199 | RAPLPLLLL | HLA-B*07:02 |
| 200 | GLLGTLRVL | HLA-A*02:01 |
| 201 | VWILQKVNLAF | HLA-A*24:02 |
| 202 | KLLLLSSVK | HLA-A*03:01 |
| 203 | AILVPQPPK | HLA-A*03:01 |
| 204 | VVRASSGLK | HLA-A*03:01 |
| 205 | SLIPIVPFKS | HLA-A*03:01 |
| 206 | VEGVHFVQLL | HLA-B*44:02 |
| 207 | LPALLRSL | HLA-B*07:02 |
| 208 | YVGPTRLEL | HLA-B*07:02 |
| 209 | AILLPQLPK | HLA-A*03:01 |
| 210 | ASRIQVILL | HLA-B*07:02 |
| 211 | VVTIVMHIYK | HLA-A*03:01 |
| 212 | WETRLHNLW | HLA-B*44:02 |
| 213 | TLLSFKTVLFK | HLA-A*03:01 |
| 214 | RPSPVRVAAL | HLA-B*07:02 |
| 215 | TPLTRTTL | HLA-B*07:02 |
| 216 | ILRTVLPSL | HLA-B*08:01 |

Mass Spectrometry Analyses

The HLA peptide pools as obtained were separated according to their hydrophobicity by reversed-phase chromatography (nanoAcquity UPLC system, Waters) and the eluting peptides were analyzed in LTQ velos and fusion hybrid mass spectrometers (ThermoElectron) equipped with an ESI source. Peptide pools were loaded directly onto the analytical fused-silica micro-capillary column (75 µm i.d.× 250 mm) packed with 1.7 µm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometers were operated in the data-dependent mode using a TOP5 strategy. In brief, a scan cycle was initiated with a full scan of high mass accuracy in the orbitrap (R=30000), which was followed by MS/MS scans also in the orbitrap (R=7500) on the 5 most abundant precursor ions with dynamic exclusion of previously selected ions. Tandem mass spectra were interpreted by SEQUEST at a fixed false discovery rate (q≤0.05) and additional manual control. In cases where the identified peptide sequence was uncertain it was additionally validated by comparison of the generated natural peptide fragmentation pattern with the fragmentation pattern of a synthetic sequence-identical reference peptide.

Figures 1, 1E:
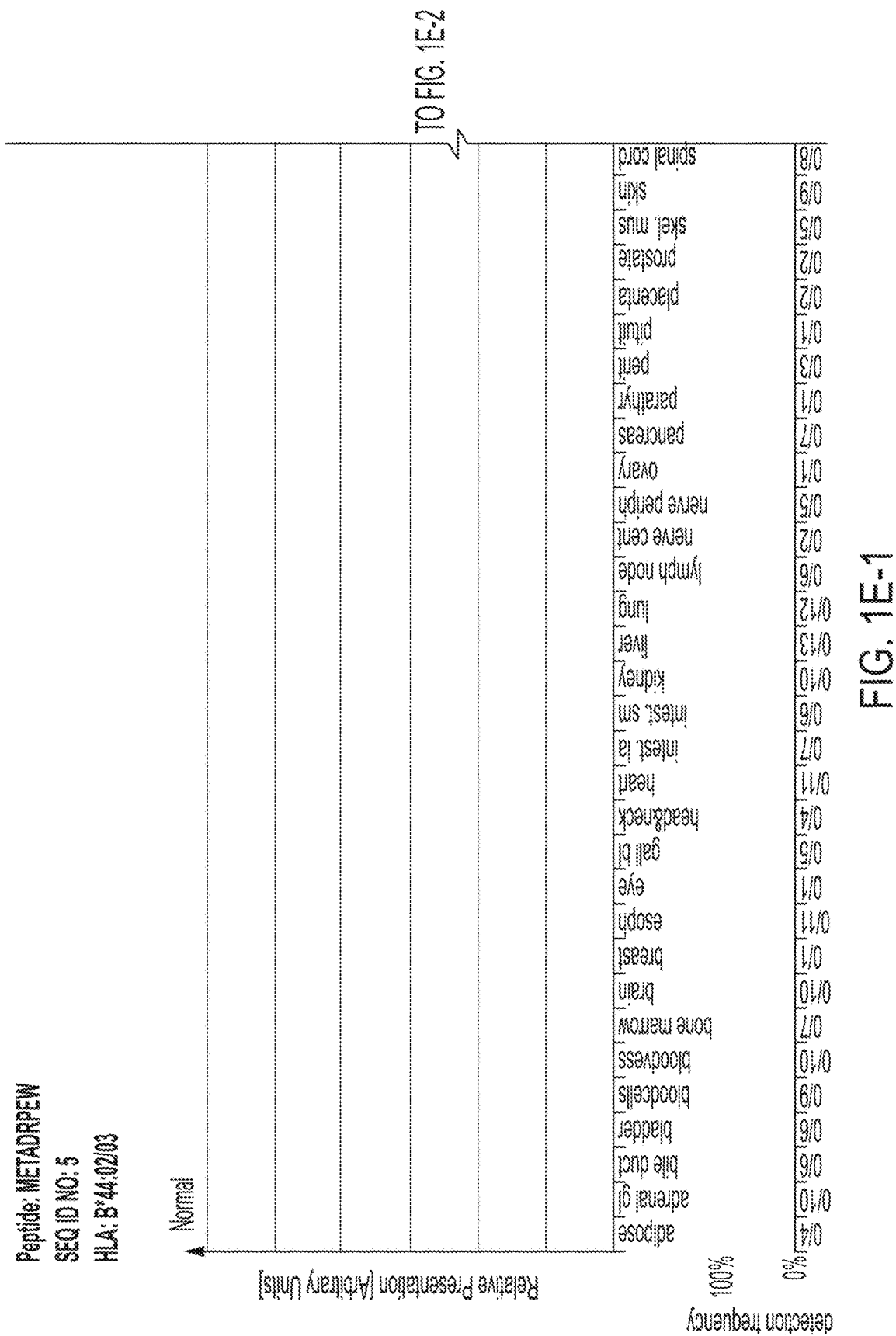
Figures 1, 1E, 2:
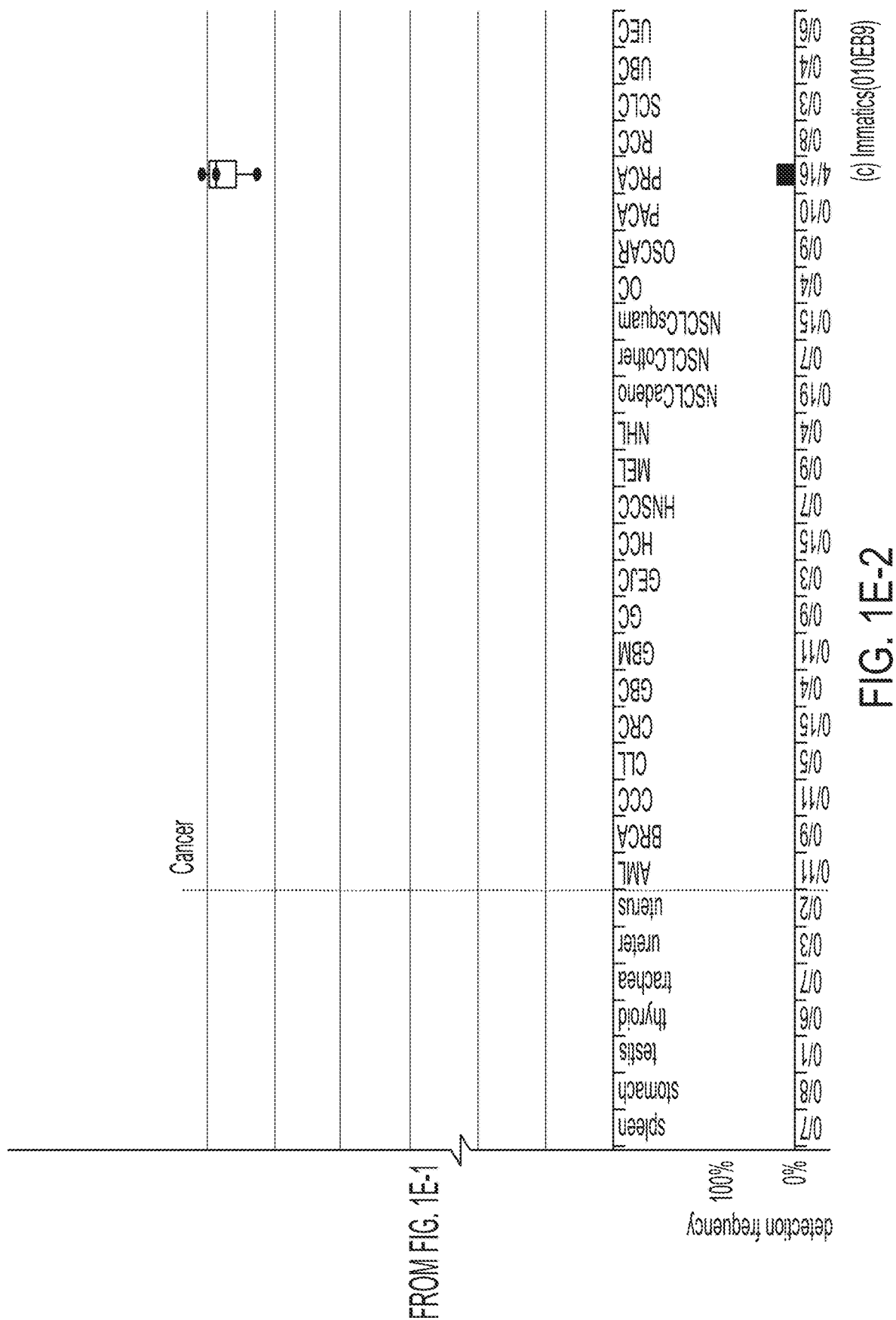

Label-free relative LC-MS quantitation was performed by ion counting i.e., by extraction and analysis of LC-MS features (Mueller et al., 2007). The method assumes that the peptide's LC-MS signal area correlates with its abundance in the sample. Extracted features were further processed by charge state deconvolution and retention time alignment (Mueller et al., 2008; Sturm et al., 2008). Finally, all LC-MS features were cross-referenced with the sequence identification results to combine quantitative data of different samples and tissues to peptide presentation profiles. The quantitative data were normalized in a two-tier fashion according to central tendency to account for variation within technical and biological replicates. Thus, each identified peptide can be associated with quantitative data allowing relative quantification between samples and tissues. In addition, all quantitative data acquired for peptide candidates was inspected manually to assure data consistency and to verify the accuracy of the automated analysis. For each peptide a presentation profile was calculated showing the mean sample presentation as well as replicate variations. The profiles juxtapose AML (acute myeloid leukemia); BRCA (breast cancer); CCC (cholangiocellular carcinoma); CLL (chronic lymphocytic leukemia); CRC (colorectal cancer); GBC (gallbladder cancer); GBM (glioblastoma); GC (gastric cancer); GEJC (gastro-esophageal junction cancer); HCC (hepatocellular carcinoma); HNSCC (head and neck squamous cell carcinoma); MEL (melanoma); NHL (non-Hodgkin lymphoma); NSCLCadeno (non-small cell lung cancer adenocarcinoma); NSCLCother (NSCLC samples that could not unambiguously be assigned to NSCLCadeno or NSCLCsquam); NSCLCsquam (squamous cell non-small cell lung cancer); OC (ovarian cancer); OSCAR (esophageal cancer); PACA (pancreatic cancer); PRCA (prostate cancer); RCC (renal cell carcinoma); SCLC (small cell lung cancer); UBC (urinary bladder carcinoma); UEC (uterine endometrial cancer) samples to a baseline of normal tissue samples. Presentation profiles of exemplary over-presented peptides are shown in FIGS. 1A-1-1E-2. The plots show only those identifications of peptides as dots which were made on tissue samples positive for the respective HLA allotype which were processed using HLA specific antibodies.

Peptide presentation on the various indications for all peptides (SEQ ID NO: 1 to SEQ ID NO: 216) are shown in table 8. This table lists all indication on which the respective peptide was identified at least once, independent of the HLA typing of the sample or the antibody used to process said sample.

TABLE 8

Presentation on various cancer entities for peptides according to the invention, and thus the particular relevance of the peptides as mentioned for the diagnosis and/or treatment of the cancers as indicated. Cancer type: AML (acute myeloid leukemia); BRCA (breast cancer); CCC (cholangiocellular carcinoma); CLL (chronic lymphocytic leukemia); CRC (colorectal cancer); GBC (gallbladder cancer); GBM (glioblastoma); GC (gastric cancer); GEJC (gastro-esophageal junction cancer); HCC (hepatocellular carcinoma); HNSCC (head and neck squamous cell carcinoma); MEL (melanoma); NHL (non-Hodgkin lymphoma); NSCLC (non-small cell lung cancer); OC (ovarian cancer); OSCAR (esophageal cancer); PACA (pancreatic cancer); PRCA (prostate cancer); RCC (renal cell carcinoma); SCLC (small cell lung cancer); UBC (urinary bladder carcinoma); UEC (uterine endometrial cancer).

| SEQ ID NO | Sequence | Peptide presentation on cancer types |
|---|---|---|
| 1 | AILAPPAILK | BRCA, CCC, CRC, GBC, HCC, HNSCC, MEL, NSCLC, OC, OSCAR, PACA, PRCA, UBC, UEC |
| 2 | GTVFVLLSK | HNSCC, NSCLC, OSCAR, RCC |
| 3 | VYIASSFKI | HCC, NSCLC |
| 4 | IQAPALLKV | CLL, CRC, NHL |
| 5 | METADRPEW | BRCA, PRCA |
| 6 | SHSLPAFTL | PRCA |
| 7 | IYIPTNSIYKF | HCC, PRCA |
| 8 | VIYNQTLMK | CCC, HCC |
| 9 | LLGVVSHSV | CLL, NHL |
| 10 | ILMILQPQL | HNSCC, NSCLC, NSCLC, RCC, UEC |
| 11 | TEIGTVIKLF | PRCA |
| 12 | RLQEGLAAL | RCC |
| 13 | LYDTVTHTF | GC, RCC |
| 14 | ILAPPQRISF | CRC, GBC, HNSCC, NSCLC, OSCAR, PACA, SCLC |
| 15 | SPVETRSLL | CCC, HNSCC, NSCLC, PACA |
| 16 | NFHTLAQQLLF | HNSCC, NSCLC |
| 17 | MVNWSLTNK | HNSCC, OSCAR, UEC |
| 18 | SLSKLVATV | CCC, CRC, GC, OSCAR, PACA |

TABLE 8-continued

Presentation on various cancer entities for peptides according to the invention, and thus the particular relevance of the peptides as mentioned for the diagnosis and/or treatment of the cancers as indicated. Cancer type: AML (acute myeloid leukemia); BRCA (breast cancer); CCC (cholangiocellular carcinoma); CLL (chronic lymphocytic leukemia); CRC (colorectal cancer); GBC (gallbladder cancer); GBM (glioblastoma); GC (gastric cancer); GEJC (gastro-esophageal junction cancer); HCC (hepatocellular carcinoma); HNSCC (head and neck squamous cell carcinoma); MEL (melanoma); NHL (non-Hodgkin lymphoma); NSCLC (non-small cell lung cancer); OC (ovarian cancer); OSCAR (esophageal cancer); PACA (pancreatic cancer); PRCA (prostate cancer); RCC (renal cell carcinoma); SCLC (small cell lung cancer); UBC (urinary bladder carcinoma); UEC (uterine endometrial cancer).

| SEQ ID NO | Sequence | Peptide presentation on cancer types |
|---|---|---|
| 19 | RILEVVRQPK | HCC, HNSCC, MEL, NSCLC, UBC |
| 20 | ILAPPAILK | BRCA, CCC, CRC, GBC, HCC, HNSCC, MEL, NSCLC, OC, OSCAR, UBC, UEC |
| 21 | MLSAQFILK | NHL |
| 22 | RVIEVVMNSK | GBM, HCC, HNSCC, MEL |
| 23 | AETKQFWSA | GC, OSCAR, PRCA, UTC |
| 24 | LIYIPTNSIYK | HCC, PRCA |
| 25 | GVCSTLTIK | CRC, GC, NSCLC, RCC, UBC |
| 26 | ETNTIEFIY | BRCA, CRC, NSCLC, MEL, RCC, UBC |
| 27 | SQAKQITIW | AML, CCC, HCC, PACA |
| 28 | ATLQAVTLYKK | MEL |
| 29 | GTFIAPVMK | CRC, HNSCC, NSCLC, OSCAR |
| 30 | SLKSSILFL | CCC, GC, HNSCC, NSCLC, PACA |
| 31 | VFLLLPYPRF | OC, RCC |
| 32 | TAMTTLMAF | HNSCC, MEL, OSCAR, PACA, UEC |
| 33 | AYIPFPPLI | HCC, PRCA |
| 34 | LLFKGLMWK | HCC, MEL, UBC |
| 35 | SLATAISAK | CLL, NHL |
| 36 | KEIEAQEAA | CRC, OC, RCC, UEC |
| 37 | RLYSGSSFLY | MEL |
| 38 | AVVSHFILY | AML, GBC, MEL |
| 39 | RELGVGIAL | HNSCC, OSCAR, UBC |
| 40 | LYQTTIELF | PRCA |
| 41 | APQPRSLAA | BRCA, CCC, GC, HCC, HNSCC, MEL, NHL, NSCLC |
| 42 | LLSRGILIL | CCC, CRC, GC, NSCLC, PRCA |
| 43 | VFIPSVINL | PRCA |
| 44 | SLFPYFLNK | MEL |
| 45 | SLFPISLTV | HNSCC, NSCLC, SCLC |
| 46 | GESIYLLVRKW | CLL, NHL |
| 47 | LYIFTTRPF | MEL, NSCLC |
| 48 | TEMSVSALY | BRCA |
| 49 | IYFHLNNVVTI | HNSCC, NSCLC |

TABLE 8-continued

Presentation on various cancer entities for peptides according to the invention, and thus the particular relevance of the peptides as mentioned for the diagnosis and/or treatment of the cancers as indicated. Cancer type: AML (acute myeloid leukemia); BRCA (breast cancer); CCC (cholangiocellular carcinoma); CLL (chronic lymphocytic leukemia); CRC (colorectal cancer); GBC (gallbladder cancer); GBM (glioblastoma); GC (gastric cancer); GEJC (gastro-esophageal junction cancer); HCC (hepatocellular carcinoma); HNSCC (head and neck squamous cell carcinoma); MEL (melanoma); NHL (non-Hodgkin lymphoma); NSCLC (non-small cell lung cancer); OC (ovarian cancer); OSCAR (esophageal cancer); PACA (pancreatic cancer); PRCA (prostate cancer); RCC (renal cell carcinoma); SCLC (small cell lung cancer); UBC (urinary bladder carcinoma); UEC (uterine endometrial cancer).

| SEQ ID NO | Sequence | Peptide presentation on cancer types |
|---|---|---|
| 50 | KTIDLVIVR | HNSCC, NSCLC, UBC |
| 51 | SVFSLVHLFDK | NHL, RCC |
| 52 | SPLPHLGPL | BRCA, CRC, GC, HCC, RCC |
| 53 | TTLENLPQK | BRCA, GBC, NSCLC, OC, OSCAR, PACA, UEC |
| 54 | ASSPVILLL | HCC, HNSCC, MEL, NSCLC, OC, UBC, UEC |
| 55 | SPVSASWIL | MEL, UEC |
| 56 | DVDIHKDLY | PRCA |
| 57 | IIIDRILLL | NSCLC |
| 58 | REQLDGATL | BRCA, CCC, CRC, GBC, GC, HNSCC, MEL, NSCLC, OC, OSCAR, PACA |
| 59 | AVDLGVLEL | NHL, MEL, OC, RCC |
| 60 | VSPDEVLALW | HNSCC, MEL, OC, UBC |
| 61 | GLIAFAIFK | CRC, GC |
| 62 | SFSLLLPYL | AML, CRC, HCC, MEL, NSCLC |
| 63 | MPANFETIGF | OC |
| 64 | LPTRSLPAF | RCC |
| 65 | NSDLFYLLL | NSCLC, OSCAR, PACA, UBC |
| 66 | RPLILIRI | AML, CRC, GBC, HNSCC, RCC |
| 67 | GRFWLPFNF | MEL, PRCA, SCLC, UEC |
| 68 | TVDKGELLY | BRCA, GBC, GC, HCC, HNSCC, NSCLC, OC, OSCAR, PACA, RCC, UBC |
| 69 | KYPTIICGF | CRC, GBC |
| 70 | LIAGLIFLK | CLL, NHL, OC, RCC, UBC, UEC |
| 71 | LIDSLLLLL | MEL, NHL, OC |
| 72 | GSCSFALSR | CCC, GC, UBC |
| 73 | NQKGLISL | CLL, GBC, MEL, NHL, NSCLC, RCC |
| 74 | TLNVLITL | CRC, GC, MEL, NSCLC, OC, RCC |
| 75 | TTAAVYILK | NHL, OC |
| 76 | VQSGVPSRF | GBC, GC, NSCLC |
| 77 | YPDVPIGQL | CRC |
| 78 | TPSHSTPSF | GC, PACA |
| 79 | SLFRLSISF | BRCA, NSCLC, PACA, RCC, UBC |
| 80 | IFDLSDPRF | GBC, GC, HNSCC, MEL, UBC, UEC |
| 81 | KLIAGLIFLK | AML, NHL, OC, RCC, UBC, UEC |

TABLE 8-continued

Presentation on various cancer entities for peptides according to the invention, and thus the particular relevance of the peptides as mentioned for the diagnosis and/or treatment of the cancers as indicated. Cancer type: AML (acute myeloid leukemia); BRCA (breast cancer); CCC (cholangiocellular carcinoma); CLL (chronic lymphocytic leukemia); CRC (colorectal cancer); GBC (gallbladder cancer); GBM (glioblastoma); GC (gastric cancer); GEJC (gastro-esophageal junction cancer); HCC (hepatocellular carcinoma); HNSCC (head and neck squamous cell carcinoma); MEL (melanoma); NHL (non-Hodgkin lymphoma); NSCLC (non-small cell lung cancer); OC (ovarian cancer); OSCAR (esophageal cancer); PACA (pancreatic cancer); PRCA (prostate cancer); RCC (renal cell carcinoma); SCLC (small cell lung cancer); UBC (urinary bladder carcinoma); UEC (uterine endometrial cancer).

| SEQ ID NO | Sequence | Peptide presentation on cancer types |
|---|---|---|
| 82 | VLQSLQHEL | RCC |
| 83 | EAAPNIMHY | PRCA |
| 84 | KEFAFLEHSL | CRC, GC, HNSCC, NSCLC, OC, OSCAR, UBC, UEC |
| 85 | LPHPVNSGL | CCC, NSCLC, NSCLC, NSCLC, UBC |
| 86 | VANDRLSFL | NSCLC, PRCA |
| 87 | LHLNPGLSF | BRCA, GC, MEL, NHL, PACA |
| 88 | KVGAVVHLK | BRCA, HCC, NSCLC, OC, OSCAR, RCC, UBC, UEC |
| 89 | SPSSPLLLLA | BRCA, GC, OC, SCLC, UBC |
| 90 | LALLGAPPPK | AML, CCC, CRC, GBC, GC, HCC, HNSCC, NSCLC, OC, OSCAR, PACA, PRCA, RCC, SCLC, UEC |
| 91 | RIVTYIVAK | AML, BRCA, CCC, HCC, MEL, NHL, NSCLC, OC, OSCAR, PACA, PRCA, UBC, UEC |
| 92 | LNFSDVFLY | GC, HNSCC, MEL, NHL, NSCLC, PRCA |
| 93 | SPIGLSLIL | CCC, HNSCC, NSCLC, OSCAR, SCLC, UBC |
| 94 | AVFLGNPSNQK | CCC, GC, NHL, NSCLC, OSCAR |
| 95 | YAFRNQTL | PRCA, SCLC |
| 96 | HPRESLNMLVAF | CCC, GBC, MEL, NSCLC, PACA, UBC |
| 97 | ALIVLHLSL | AML, CRC, MEL, NHL, OSCAR |
| 98 | FSEIFQDFL | AML, BRCA, GC, HNSCC, NHL, RCC, UEC |
| 99 | RADEEQASF | CRC, NSCLC, OSCAR, PACA, UBC, UEC |
| 100 | SPAPSLARFLSL | BRCA, HNSCC, NSCLC, MEL |
| 101 | ATNSFLLIK | GC, NSCLC, SCLC, PACA, PRCA |
| 102 | FLLLEKGGEL | BRCA, CRC, HCC, HNSCC, NSCLC, PACA |
| 103 | RPWLSSPTGL | GBC, GC, HNSCC, NHL, NSCLC, OC, PACA, RCC |
| 104 | GSLQTLPPK | GBC, OSCAR, UBC |
| 105 | LVFESVVAA | GBC, HNSCC, NHL, NSCLC, RCC, UBC |
| 106 | GLLDAFLRL | HCC |
| 107 | SVISVLTTPK | GBC, NSCLC, OSCAR, UBC, UEC |
| 108 | SLQESLPNA | AML |
| 109 | MPKLFLTAC | AML, CCC, CLL, CRC, GC, HCC, NSCLC, RCC |
| 110 | APSLARFLSL | BRCA, HNSCC, MEL, NSCLC, OC, OSCAR, RCC, SCLC |
| 111 | RPIWDVRSA | HNSCC, NSCLC, SCLC |
| 112 | ETYGTFVLR | BRCA, CCC, CRC, GBC, HCC, HNSCC, NSCLC, OC, OSCAR, SCLC, RCC, UBC |

TABLE 8-continued

Presentation on various cancer entities for peptides according to the invention, and thus the particular relevance of the peptides as mentioned for the diagnosis and/or treatment of the cancers as indicated. Cancer type: AML (acute myeloid leukemia); BRCA (breast cancer); CCC (cholangiocellular carcinoma); CLL (chronic lymphocytic leukemia); CRC (colorectal cancer); GBC (gallbladder cancer); GBM (glioblastoma); GC (gastric cancer); GEJC (gastro-esophageal junction cancer); HCC (hepatocellular carcinoma); HNSCC (head and neck squamous cell carcinoma); MEL (melanoma); NHL (non-Hodgkin lymphoma); NSCLC (non-small cell lung cancer); OC (ovarian cancer); OSCAR (esophageal cancer); PACA (pancreatic cancer); PRCA (prostate cancer); RCC (renal cell carcinoma); SCLC (small cell lung cancer); UBC (urinary bladder carcinoma); UEC (uterine endometrial cancer).

| SEQ ID NO | Sequence | Peptide presentation on cancer types |
|---|---|---|
| 113 | ALGPMAFRV | BRCA, CRC, NSCLC, OC, OSCAR, PACA, RCC |
| 114 | VPHHLLSSV | GBC, GC, PACA, RCC |
| 115 | LWEEKPVCL | CCC, CRC, GBC, HCC, NSCLC, PACA, PRCA, UBC, UEC |
| 116 | IYLTKSNLVNM | HNSCC, NHL, NSCLC, OSCAR |
| 117 | GEAAAARPV | HCC, MEL, NSCLC |
| 118 | RLLRLIPIL | GBC, HNSCC, MEL, NSCLC, OC, PACA, RCC |
| 119 | VLHGLLFTL | AML, NHL, NSCLC, RCC |
| 120 | APGPRSQGL | BRCA, CRC, GC, PRCA, UBC |
| 121 | ILVTAWKGV | GBC, GC, HCC, NHL, NSCLC, OSCAR, RCC |
| 122 | FTQKINSTW | BRCA, CCC, CLL, CRC, GBC, GC, HNSCC, MEL, NSCLC, PRCA, RCC, SCLC, UBC |
| 123 | TYLESSVRI | HCC |
| 124 | SPSSNSREL | AML, CRC, GBC, GC, HNSCC, MEL, OC, UBC |
| 125 | ALAQGANLK | GB, MEL, RCC |
| 126 | NPELLVILL | HNSCC, NSCLC, OSCAR, RCC |
| 127 | TVATQVATSK | BRCA, HNSCC, NSCLC, OC, OSCAR, UBC |
| 128 | MTFVPLLAR | CRC, GBC, GC, HCC, NHL, MEL, NSCLC, OC, OSCAR, PACA, UBC, UEC |
| 129 | IPISIFKMA | CCC, HCC, NHL, PACA, RCC, SCLC, UBC |
| 130 | ITPDSIPSV | AML, GBC, NHL, OC, SCLC |
| 131 | TILAKQNVL | AML, HCC, OC, RCC |
| 132 | LYLETRSEF | BRCA, GBC, GC, HCC, MEL, NSCLC, OC, OSCAR, PACA, PRCA, RCC |
| 133 | KFPPSASEF | CRC, GC, NSCLC, PRCA, UBC |
| 134 | MPCTTILRI | AML, CLL, CRC, GC, HCC, HNSCC, MEL, NHL, NSCLC, OSCAR, RCC, PACA, PRCA, UBC, UEC |
| 135 | SADTAELLL | CCC, HCC |
| 136 | YSSEIWDLY | BRCA, GBC, HCC, MEL, UEC |
| 137 | MPIQVLKGL | BRCA, GC, NHL, RCC, PRCA |
| 138 | RTLPLEGSPK | BRCA, CCC, GBM, NSCLC, PACA, PRCA, UEC |
| 139 | EEGRIITKW | BRCA, CRC, CCC, GBC, HCC, HNSCC, MEL, NSCLC, OSCAR, PACA, RCC, UBC |
| 140 | QPAPQPLL | BRCA, CRC, HNSCC, NHL, OSCAR, RCC, SCLC, UBC |
| 141 | REVAGASAL | NSCLC, PACA |
| 142 | YMLEMDNSMKI | CCC, CRC, NSCLC, PACA |

TABLE 8-continued

Presentation on various cancer entities for peptides according to the invention, and thus the particular relevance of the peptides as mentioned for the diagnosis and/or treatment of the cancers as indicated. Cancer type: AML (acute myeloid leukemia); BRCA (breast cancer); CCC (cholangiocellular carcinoma); CLL (chronic lymphocytic leukemia); CRC (colorectal cancer); GBC (gallbladder cancer); GBM (glioblastoma); GC (gastric cancer); GEJC (gastro-esophageal junction cancer); HCC (hepatocellular carcinoma); HNSCC (head and neck squamous cell carcinoma); MEL (melanoma); NHL (non-Hodgkin lymphoma); NSCLC (non-small cell lung cancer); OC (ovarian cancer); OSCAR (esophageal cancer); PACA (pancreatic cancer); PRCA (prostate cancer); RCC (renal cell carcinoma); SCLC (small cell lung cancer); UBC (urinary bladder carcinoma); UEC (uterine endometrial cancer).

| SEQ ID NO | Sequence | Peptide presentation on cancer types |
|---|---|---|
| 143 | AVLGALLRH | BRCA, GC, GBC, HCC, NSCLC, OSCARPACA, PRCA, RCC, SCLC |
| 144 | IIVPSFYK | CCC, CRC, GBC, GBM, GC, HCC, MEL, NSCLC, RCC |
| 145 | HLFSVLSAI | BRCA, CCC, CLL, CRC, GBC, GC, HCC, HNSCC, MEL, NHL, NSCLC, OC, OSCAR, PACA, RCC, SCLC |
| 146 | KVLVDFLLK | AML, BRCA, CCC, CRC, HNSCC, MEL, NHL, RCC, SCLC, UBC |
| 147 | VEAPHLPSF | BRCA, CCC, CRC, GBC, GBM, GC, HCC, HNSCC, MEL, NHL, NSCLC, OC, OSCAR, PACA, RCC, SCLC, UBC, UEC |
| 148 | SVYMATTLK | NSCLC, OC, PACA, UBC, UEC |
| 149 | SMNSKALRWK | CCC, MEL, NHL |
| 150 | IVFLQQGEK | AML, BRCA, CCC, CRC, GC, MEL, NHL, NSCLC, OSCAR, PACA, SCLC, UBC, UEC |
| 151 | AVFVNWEQTKK | HNSCC, MEL, NHL, NSCLC, OSCAR |
| 152 | KIMEILNLK | AML, GC, MEL, NHL, NSCLC, OC, OSCAR, RCC, UBC, UEC |
| 153 | ALNLSRLTV | HCC, NSCLC, OSCAR, MEL, PRCA, HNSCC, NHL, RCC, CRC, GC, OC, CLL |
| 154 | TVTSAIVNR | CRC, GBC, GC, PACA, PRCA, SCLC, UBC |
| 155 | MPWVLMSPF | AML, CRC, NHL, NSCLC, OC, SCLC |
| 156 | SLRVPSPAL | BRCA, CRC, HNSCC, NHL, NSCLC, PRCA, RCC, UEC |
| 157 | APLRAGWAA | CCC, GC, GBC, HCC, NHL, PACA, RCC |
| 158 | FQLSGPVTF | BRCA, CRC, GBC, GC, NSCLC, OC, UEC |
| 159 | ASAIPAGAK | CRC, HNSCC, OC, RCC |
| 160 | EYLGSENVF | GC, PRCA |
| 161 | ILAASFQAR | CRC, GBM, HCC, HNSCC, RCC, UBC |
| 162 | LPVHGPLPLLL | BRCA, CCC, CRC, GBC, GC, HCC, HNSCC, NSCLC, OC, SCLC, UEC |
| 163 | LWALAIPSL | BRCA, GBC, NHL, NSCLC, OC, UEC |
| 164 | SHSSPTVSF | GC, PRCA, RCC |
| 165 | FYNPRPPLI | GBC |
| 166 | VIFLHQPPK | MEL |
| 167 | FALGPIIKQL | GBC, MEL, NSCLC, OSCAR, PRCA, UEC |
| 168 | AEGPDHHSL | AML, CRC, GBC, GC, HCC, HNSCC, OC, RCC |
| 169 | RPQGVGPAA | BRCA, GC, GBC, HNSCC, MEL, NSCLC, RCC, UBC |
| 170 | LLDSWNILI | NHL, MEL, OC, PRCA |
| 171 | NVSFEVSLLY | GC, HNSCC, NSCLC, OC, PACA, PRCA, RCC |
| 172 | LLYKTLIIL | AML, CRC, HCC, NHL, NSCLC, PACA, PRCA |

TABLE 8-continued

Presentation on various cancer entities for peptides according to the invention, and thus the particular relevance of the peptides as mentioned for the diagnosis and/or treatment of the cancers as indicated. Cancer type: AML (acute myeloid leukemia); BRCA (breast cancer); CCC (cholangiocellular carcinoma); CLL (chronic lymphocytic leukemia); CRC (colorectal cancer); GBC (gallbladder cancer); GBM (glioblastoma); GC (gastric cancer); GEJC (gastro-esophageal junction cancer); HCC (hepatocellular carcinoma); HNSCC (head and neck squamous cell carcinoma); MEL (melanoma); NHL (non-Hodgkin lymphoma); NSCLC (non-small cell lung cancer); OC (ovarian cancer); OSCAR (esophageal cancer); PACA (pancreatic cancer); PRCA (prostate cancer); RCC (renal cell carcinoma); SCLC (small cell lung cancer); UBC (urinary bladder carcinoma); UEC (uterine endometrial cancer).

| SEQ ID NO | Sequence | Peptide presentation on cancer types |
|---|---|---|
| 173 | IFTGRNAYF | GBM, GC, HCC, NSCLC, OC, UBC, UEC |
| 174 | LSGPVTFLR | BRCA, CCC, OSCAR |
| 175 | MPFLKVPPL | CLL, NHL, NSCLC, SCLC |
| 176 | AFLLSLISL | BRCA, GC, MEL, NHL, NSCLC, OSCAR, UBC |
| 177 | SYLKDHLSL | CLL, GC, NSCLC, UBC |
| 178 | SLFGGLFTR | CCC, GBC, GC, HNSCC, NSCLC, UBC |
| 179 | MIFSGVFLR | AML, BRCA, CCC, GBC, GC, HCC, HNSCC, MEL, NSCLC, OC, OSCAR, RCC, PACA, UBC, UEC |
| 180 | QYLTYYPSF | CLL, CRC, NHL, NSCLC, OSCAR, PRCA, UBC, UEC |
| 181 | FDLNIGSAY | GBC, GC, HCC, HNSCC, NHL |
| 182 | RPSLPCRSF | BRCA, HNSCC, NHL, NSCLC, OSCAR, RCC, PACA, UEC |
| 183 | VFVISGSHLF | NHL, NSCLC, UBC, UEC |
| 184 | VVHGGMSIF | AML, BRCA, CCC, GC, NSCLC |
| 185 | MPAFLSRASAL | BRCA, CRC, GBC, GC, HNSCC, MEL, NSCLC, OSCAR, UBC |
| 186 | SQIKSPVVF | BRCA, CRC, GBM, GC, HCC, NSCLC, OC, RCC, SCLC |
| 187 | RLCPAAPTGK | BRCA, HCC, HNSCC, NSCLC, OSCAR |
| 188 | KLPFFTNFL | BRCA, CCC, CLL, CRC, GBC, GC, HNSCC, MEL, NHL, NSCLC, PACA, RCC, UBC, UEC |
| 189 | IWRALGSLF | GC, MEL, NSCLC, UBC |
| 190 | STQSSLLYLK | CCC, NHL, NSCLC, OC, RCC |
| 191 | APLLPGPAA | CCC, GC, MEL, NSCLC, PACA, RCC, |
| 192 | IPLHFSTAF | AML, BRCA, GBC, GC, HCC, HNSCC, NHL, NSCLC, OC, OSCAR, RCC, SCLC, UBC, UEC |
| 193 | ILQLITVNR | BRCA, CCC, CRC, GBC, GC, HCC, HNSCC, NSCLC, OC, OSCAR, PACA, RCC, SCLC, UBC, UEC |
| 194 | VLYPSHSSF | GBC, HCC |
| 195 | AWNESSAWLL | CRC, HCC |
| 196 | NSENLLVY | CCC, CRC, MEL, NHL, NSCLC |
| 197 | HHTQLVFVF | NHL, NSCLC, OC, UBC |
| 198 | MTYQQPFSNR | GBC, HCC, HNSCC, NHL, MEL, NSCLC, OC, OSCAR, UBC, UEC |
| 199 | RAPLPLLLL | GC, HNSCC, NSCLC, UBC |
| 200 | GLLGTLRVL | GBC, HCC, NSCLC, UBC |
| 201 | VWILQKVNLAF | CCC, CRC, GBC, HCC, HNSCC, PRCA, UBC |
| 202 | KLLLLSSVK | GC, GBC, HCC, NSCLC, PACA |

TABLE 8-continued

Presentation on various cancer entities for peptides according to the invention, and thus the particular relevance of the peptides as mentioned for the diagnosis and/or treatment of the cancers as indicated. Cancer type: AML (acute myeloid leukemia); BRCA (breast cancer); CCC (cholangiocellular carcinoma); CLL (chronic lymphocytic leukemia); CRC (colorectal cancer); GBC (gallbladder cancer); GBM (glioblastoma); GC (gastric cancer); GEJC (gastro-esophageal junction cancer); HCC (hepatocellular carcinoma); HNSCC (head and neck squamous cell carcinoma); MEL (melanoma); NHL (non-Hodgkin lymphoma); NSCLC (non-small cell lung cancer); OC (ovarian cancer); OSCAR (esophageal cancer); PACA (pancreatic cancer); PRCA (prostate cancer); RCC (renal cell carcinoma); SCLC (small cell lung cancer); UBC (urinary bladder carcinoma); UEC (uterine endometrial cancer).

| SEQ ID NO | Sequence | Peptide presentation on cancer types |
| --- | --- | --- |
| 203 | AILVPQPPK | BRCA, CCC, CRC, GC, HCC, HNSCC, NHL, NSCLC, OC, OSCAR, SCLC |
| 204 | VVRASSGLK | AML, CLL, CRC, GBM, HCC, NSCLC, PACA, PRCA, RCC |
| 205 | SLIPIVPFKS | CLL, NHL |
| 206 | VEGVHFVQLL | CLL, HCC, NHL, OSCAR |
| 207 | LPALLRSL | BRCA, CLL, CRC, NSCLC |
| 208 | YVGPTRLEL | BRCA, CLL, GBM, MEL, NSCLC |
| 209 | AILLPQLPK | BRCA, CCC, HCC, GC, NSCLC, OSCAR, PACA, PRCA, RCC, SCLC, UTC |
| 210 | ASRIQVILL | BRCA, NSCLC, PRCA, SCLC, UTC |
| 211 | VVTIVMHIYK | AML, CCC, BRCA, MEL |
| 212 | WETRLHNLW | AML, BRCA, CLL, CRC, GC, HCC, HNSCC, MEL, NHL, NSCLC, OSCAR, PACA, PRCA, RCC, SCLC |
| 213 | TLLSFKTVLFK | AML, CRC, MEL, NHL, NSCLC, UEC |
| 214 | RPSPVRVAAL | AML, BRCA, CRC, GBC, GC, MEL, NHL, NSCLC, OSCAR, PACA, RCC, UBC, UEC |
| 215 | TPLTRTTL | CCC, CRC, GBM, MEL, NSCLC, OC, PACA, UBC |
| 216 | ILRTVLPSL | AML, HCC, HNSCC, NHL, NSCLC, OC, OSCAR, RCC, UEC |

Example 2

Expression Profiling of Genes Encoding the Peptides of the Invention

Over-presentation or specific presentation of a peptide on tumor cells compared to normal cells is sufficient for its usefulness in immunotherapy, and some peptides are tumor-specific despite their source protein occurring also in normal tissues. Still, mRNA expression profiling adds an additional level of safety in selection of peptide targets for immuno-therapies. Especially for therapeutic options with high safety risks, such as affinity-matured TCRs, the ideal target peptide will be derived from a protein that is unique to the tumor and not found on normal tissues.

RNA Sources and Preparation

Surgically removed tissue specimens were provided as indicated above (see Example 1) after written informed consent had been obtained from each patient. Tumor tissue specimens were snap-frozen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues for RNASeq experiments was obtained from: Asterand (Detroit, MI, USA & Royston, Herts, UK); Bio-Options Inc. (Brea, CA, USA); Geneticist Inc. (Glendale, CA, USA); ProteoGenex Inc. (Culver City, CA, USA); Tissue Solutions Ltd (Glasgow, UK).

Total RNA from tumor tissues for RNASeq experiments was obtained from: Asterand (Detroit, MI, USA & Royston, Herts, UK); BioCat GmbH (Heidelberg, Germany); BioServe (Beltsville, MD, USA); Geneticist Inc. (Glendale, CA, USA); Istituto Nazionale Tumori "Pascale" (Naples, Italy); ProteoGenex Inc. (Culver City, CA, USA); University Hospital Heidelberg (Heidelberg, Germany).

Quality and quantity of all RNA samples were assessed on an Agilent 2100 Bioanalyzer (Agilent, Waldbronn, Germany) using the RNA 6000 Pico LabChip Kit (Agilent).

RNAseq Experiments

Figures 1, 2A:
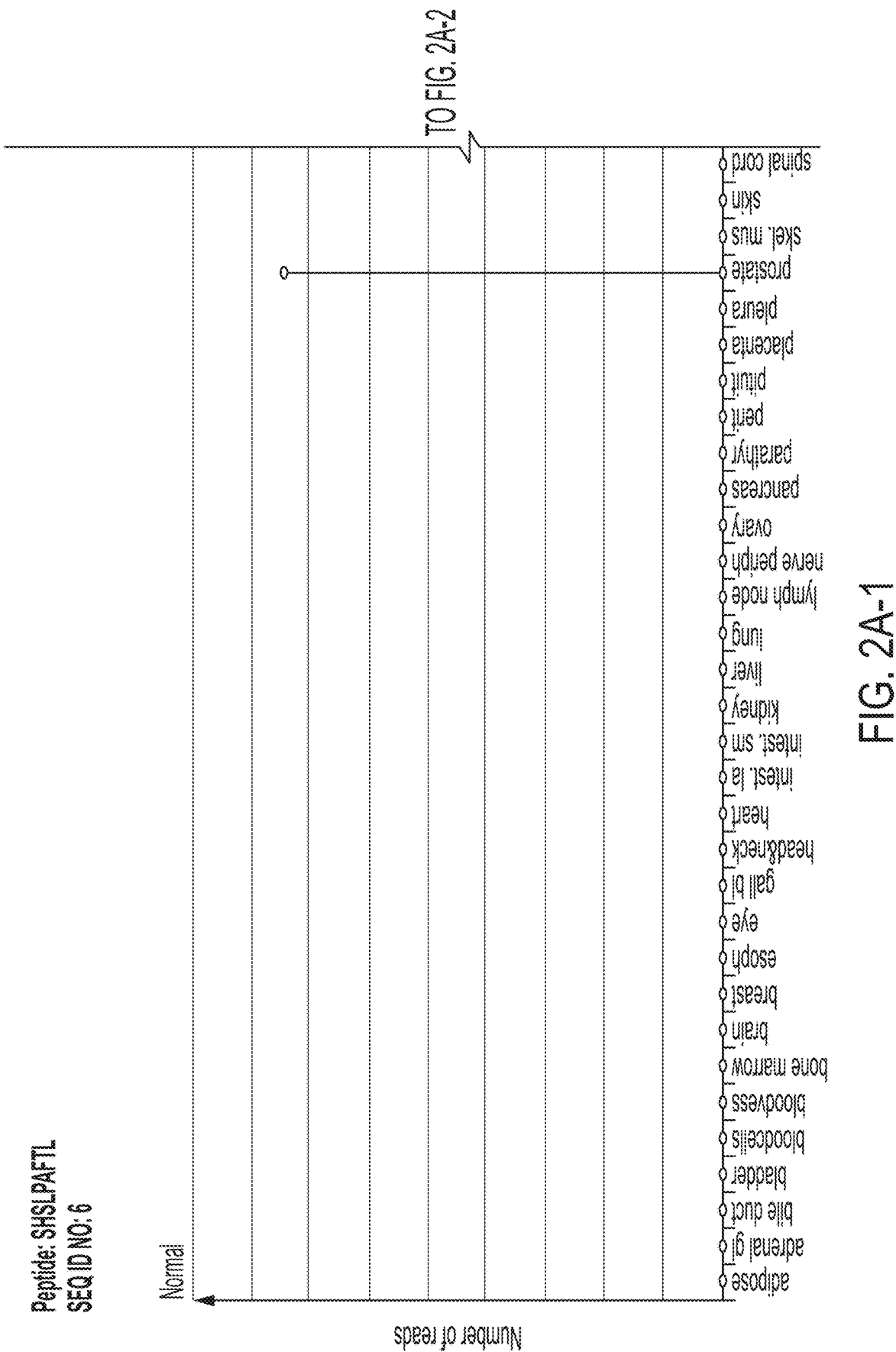
Figures 2, 2A:
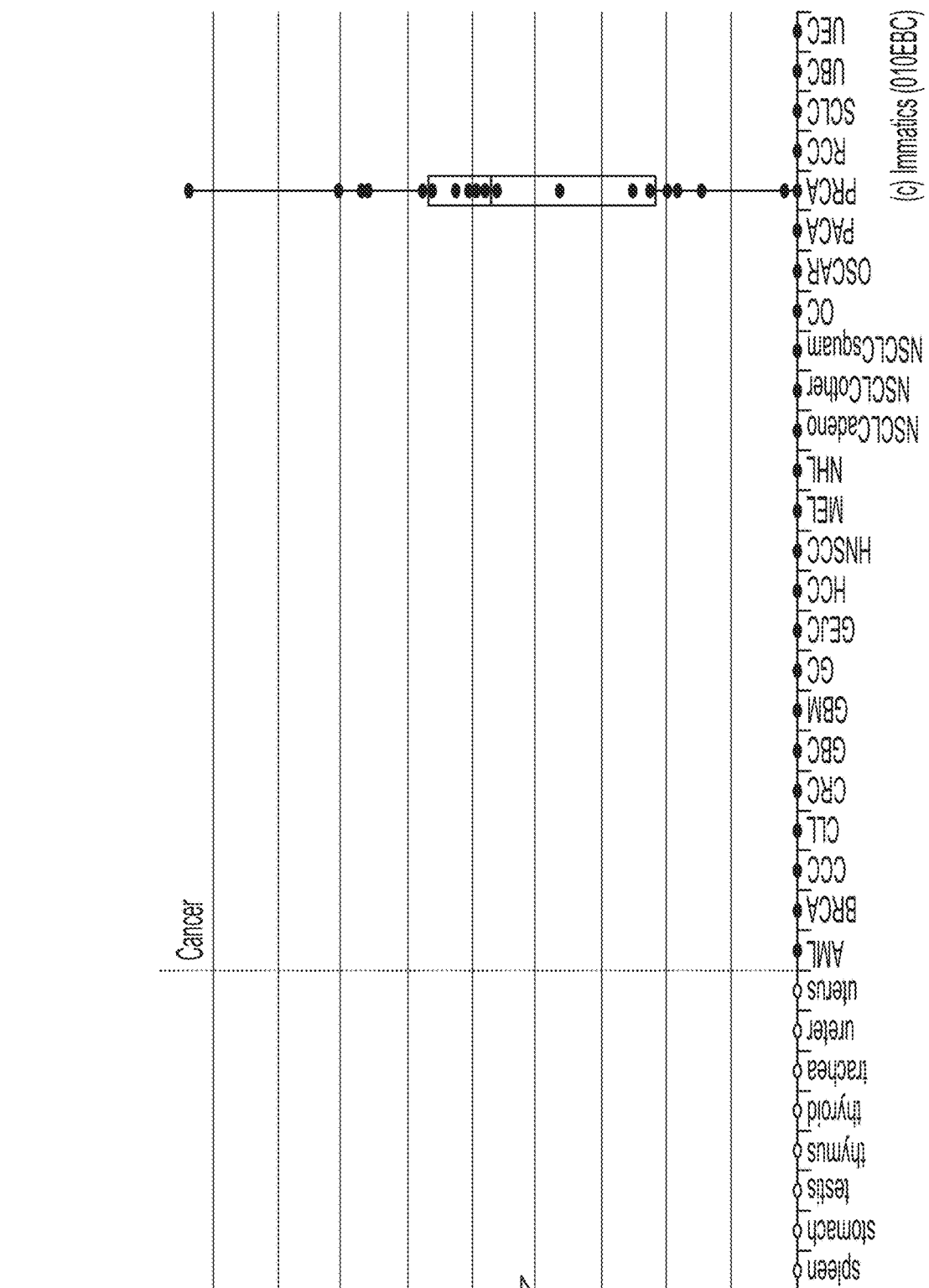
Figures 1, 2B:
Figures 2, 2B:
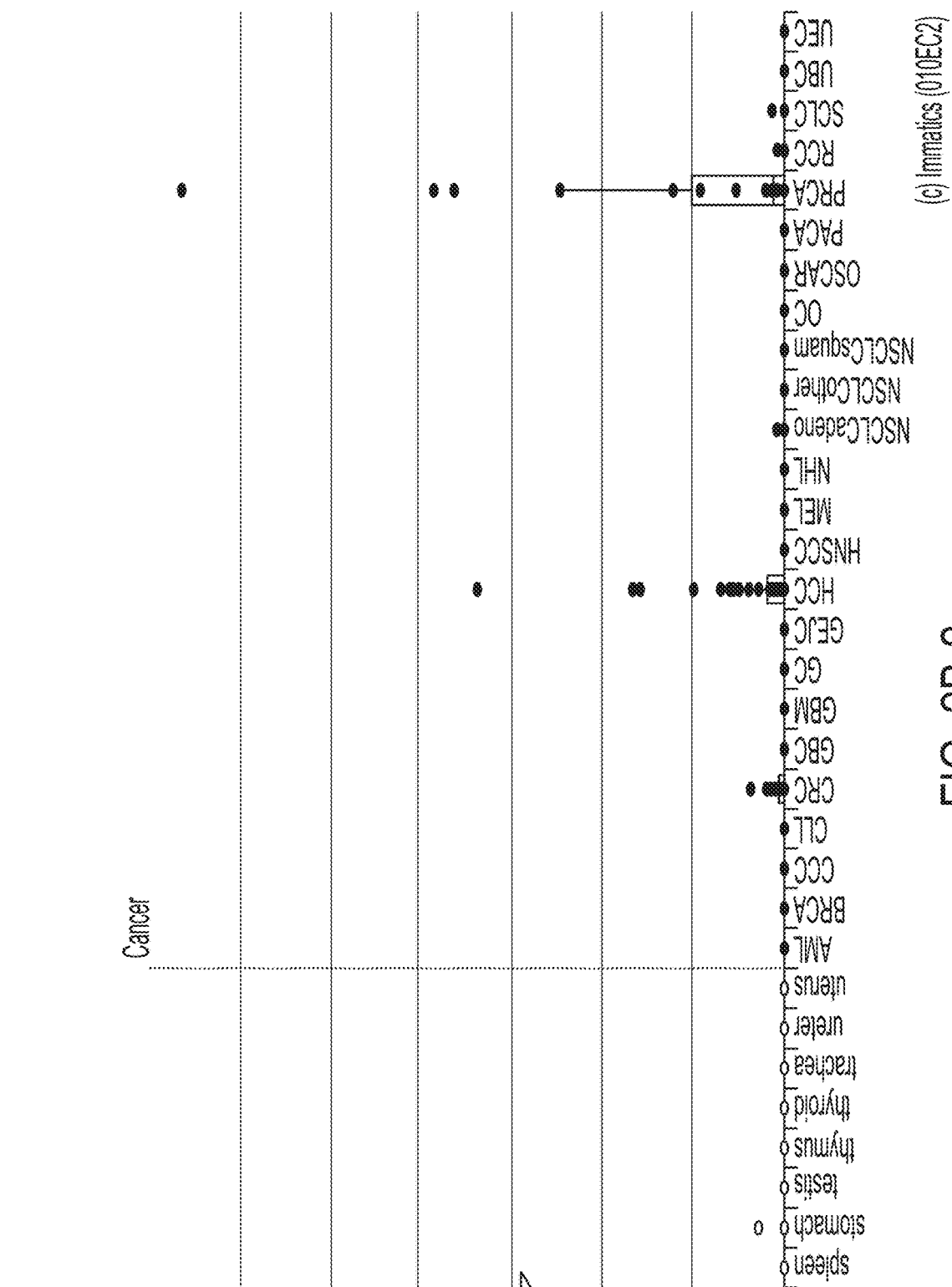
Figures 2, 2C:
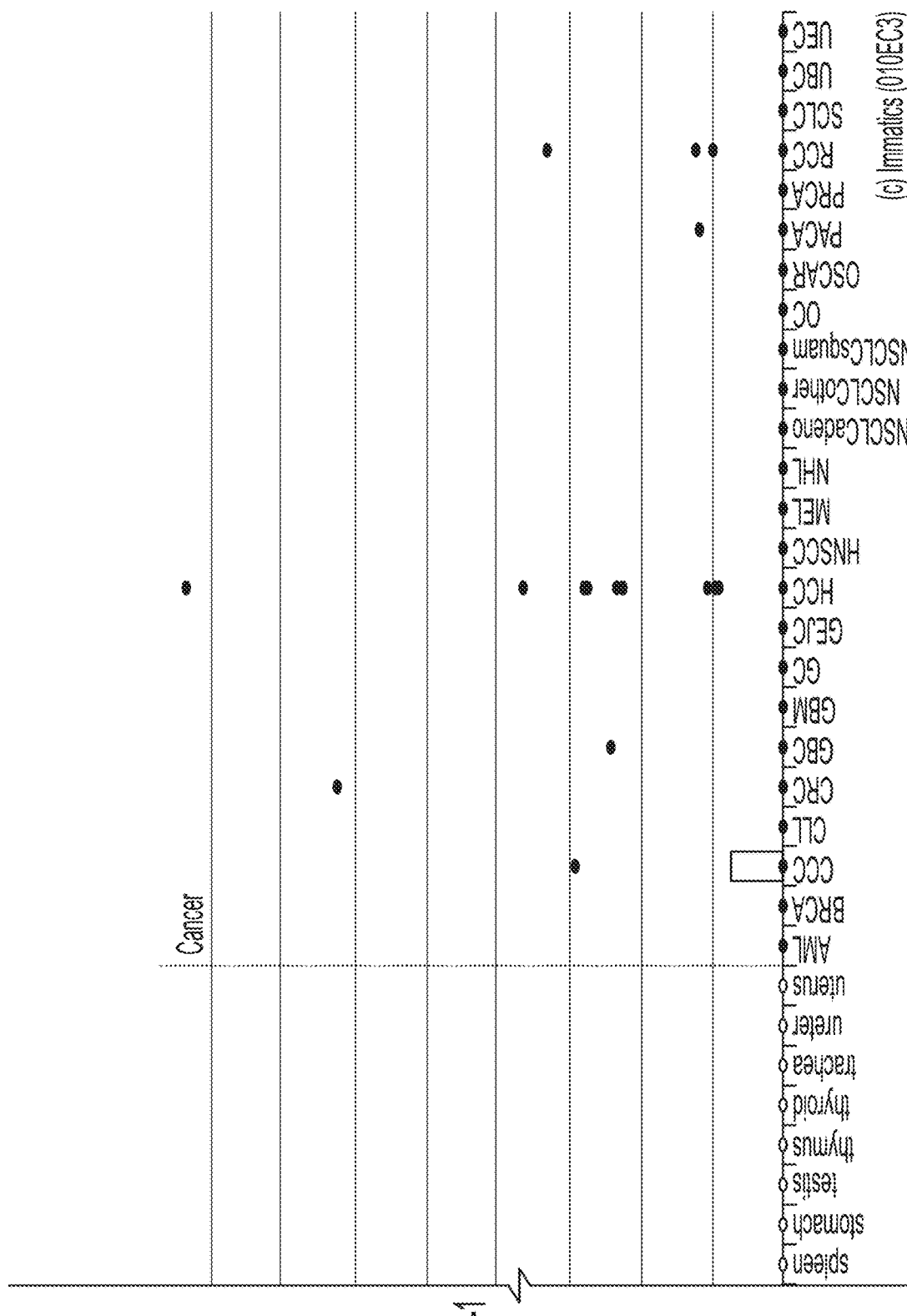
Figures 2, 2D:
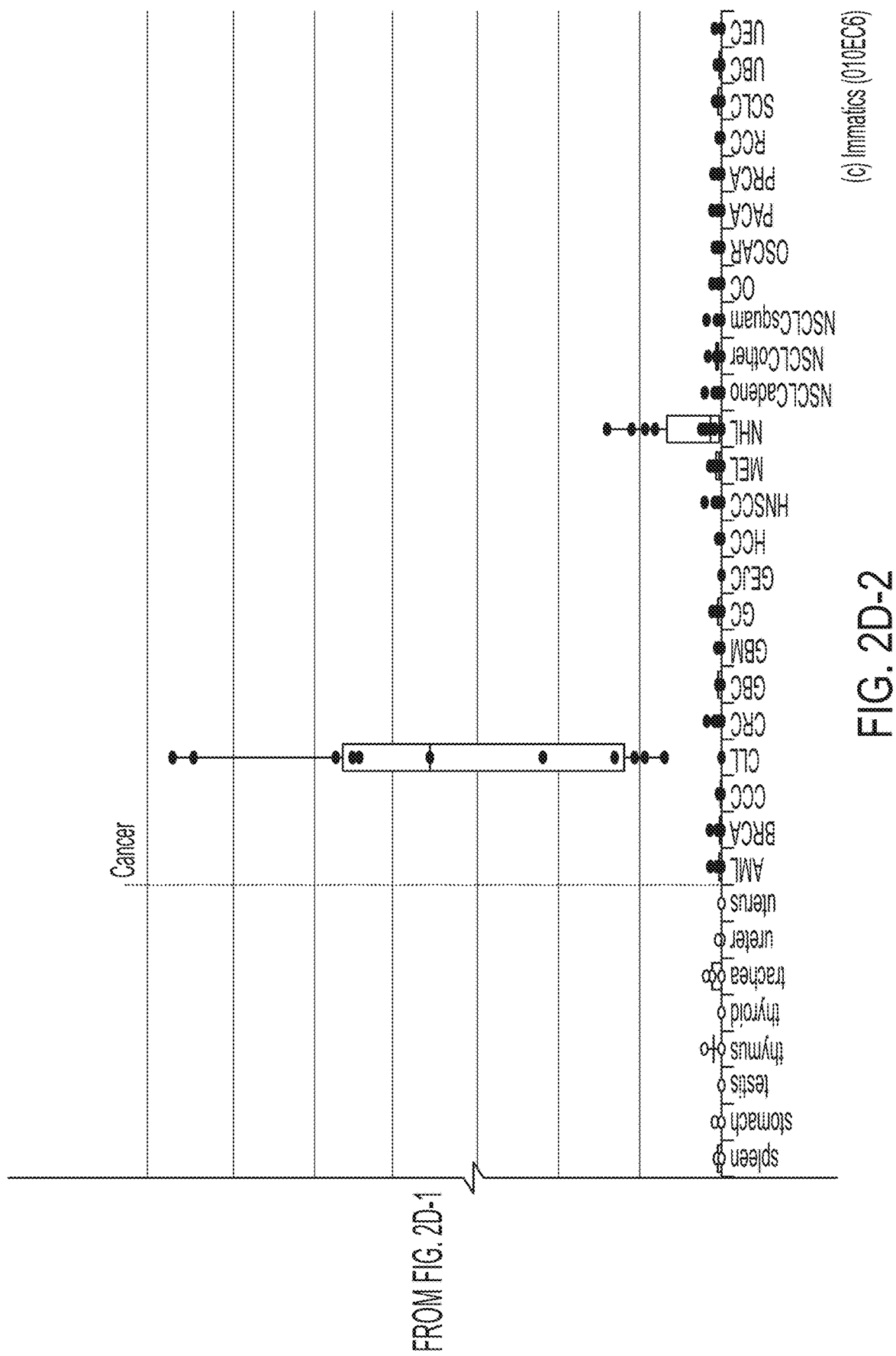
Figures 1, 2E:
Figures 2, 2E:
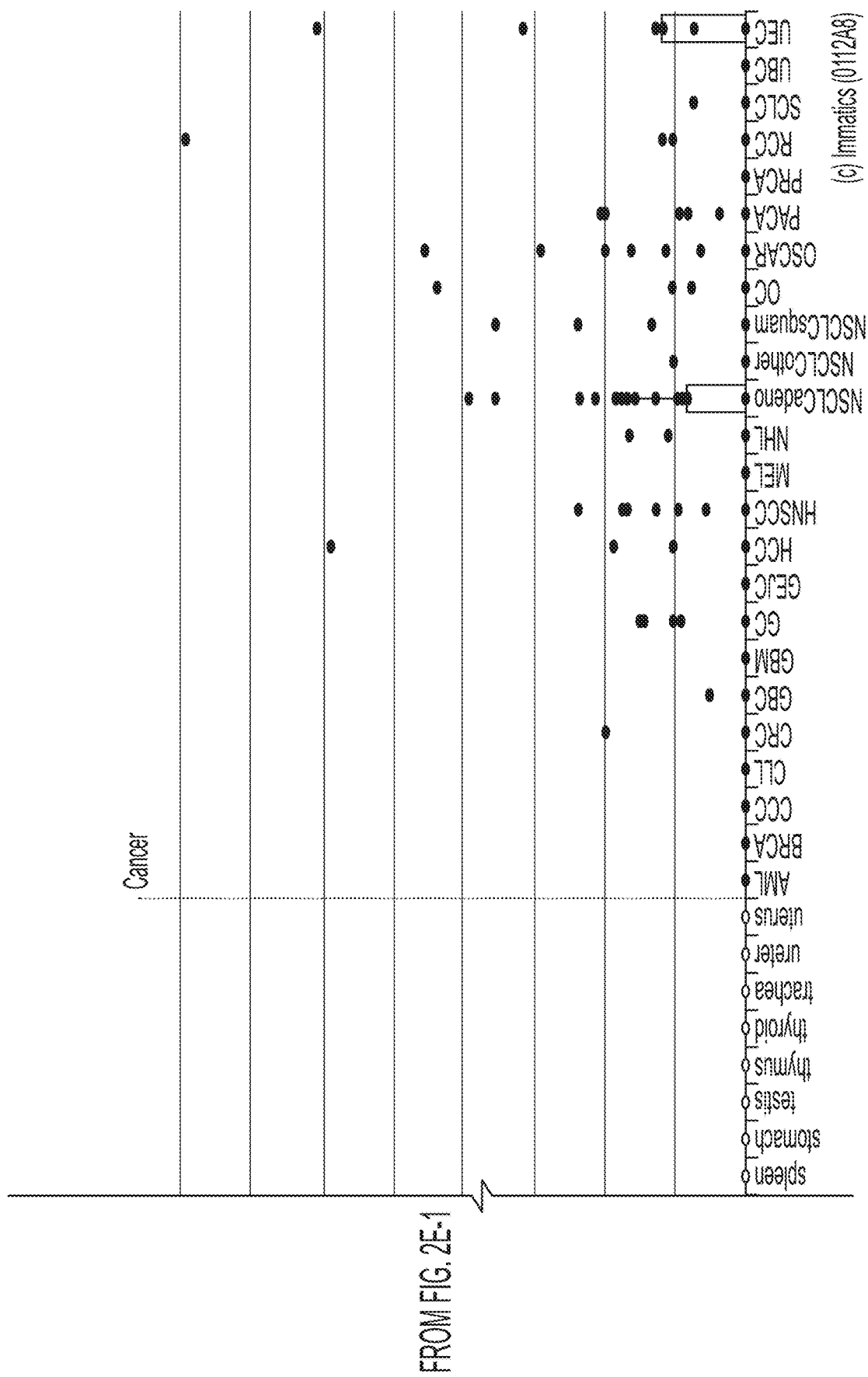
Figure 3:
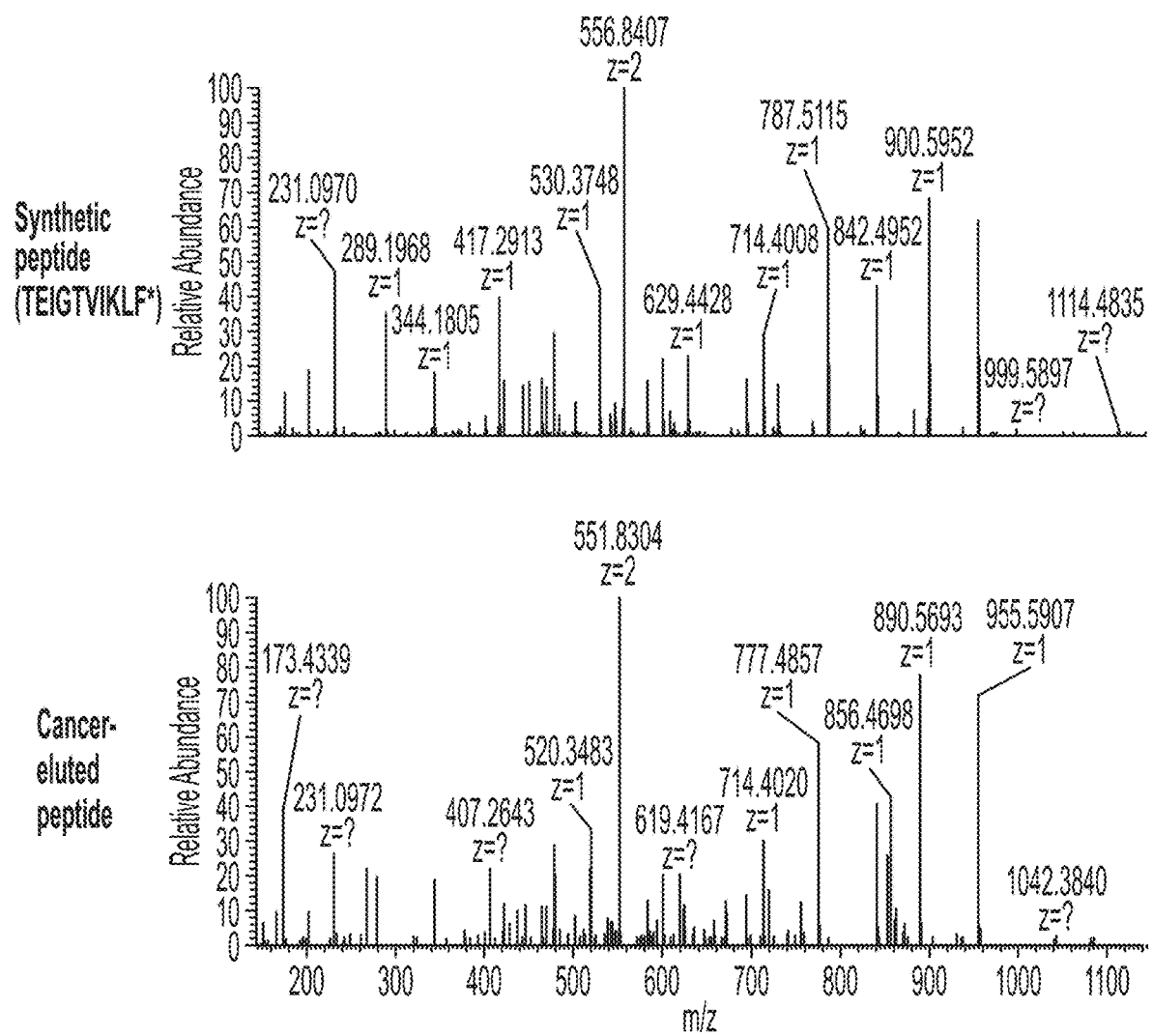
FIG. 3 shows the results of the IdentControl experiments for one exemplary peptide TEIGTVIKLF (SEQ ID NO: 11). The peptide was confirmed by IdentControl comparing the fragmentations of stable isotope labeled (SIL) standards in data-dependent acquisition (DDA) mode. Identity was confirmed using in-house determined spectral correlation threshold.
Figure 4:
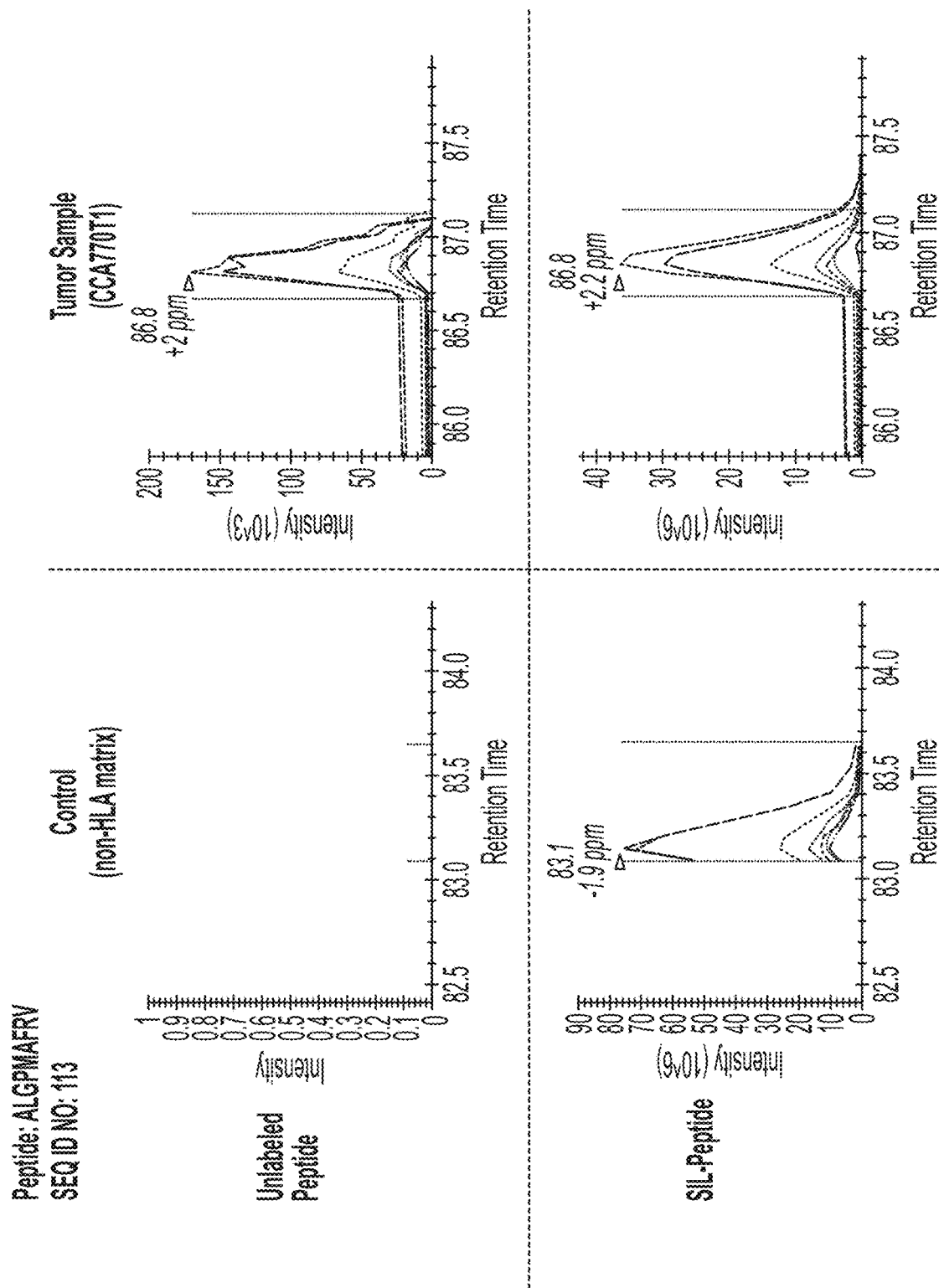
FIG. 4 shows one exemplary results for a CoElution experiment for the peptide ALGPMAFRV (SEQ ID NO: 113). The peptide was confirmed by CoElution using stable isotope labeled (SIL) internal standard and targeted MS (sPRM or IS-PRM). Non overlapping MS2 isolation windows for the SIL-peptide and the natural peptide are used. Control experiments using non-HLA peptidome sample (e.g. tryptic digest or 5% FA) as matrix are performed to confirm isotopic purity of the SIL internal standard. Peptide identity is confirmed based on objective, predefined criteria in expert manual review.

Gene expression analysis of tumor and normal tissue RNA samples was performed by next generation sequencing (RNAseq) by CeGaT (Tübingen, Germany). Briefly, sequencing libraries are prepared using the Illumina HiSeq v4 reagent kit according to the provider's protocol (Illumina Inc., San Diego, CA, USA), which includes RNA fragmentation, cDNA conversion and addition of sequencing adaptors. Libraries derived from multiple samples are mixed equimolar and sequenced on the Illumina HiSeq 2500 sequencer according to the manufacturer's instructions, generating 50 bp single end reads. RNA reads supporting the peptide are counted and shown as exemplary expression profiles of peptides of the present invention that are highly overexpressed or exclusively expressed in AML (acute myeloid leukemia); BRCA (breast cancer); CCC (cholangiocellular carcinoma); CLL (chronic lymphocytic leukemia); CRC (colorectal cancer); GBC (gallbladder cancer); GBM (glioblastoma); GC (gastric cancer); GEJC (gastroesophageal junction cancer); HCC (hepatocellular carcinoma); HNSCC (head and neck squamous cell carcinoma); MEL (melanoma); NHL (non-Hodgkin lymphoma); NSCLC (non-small cell lung cancer); OC (ovarian cancer); OSCAR (esophageal cancer); PACA (pancreatic cancer); PRCA (prostate cancer); RCC (renal cell carcinoma); SCLC (small cell lung cancer); UBC (urinary bladder carcinoma); UEC (uterine endometrial cancer) in FIGS. 2A-1-2E-2. Furthermore, expression scores from the RNAseq experiments are listed in table 9.

TABLE 9

Expression scores. The table lists peptides that are very highly overexpressed in tumors compared to a panel of normal tissues (+++) or highly overexpressed in tumors compared to a panel of normal tissues (++) or overexpressed in tumors compared to a panel of normal tissues (+) according to the RNAseq experiments. The baseline for this score was calculated from measurements of the following relevant normal tissues: adipose tissue; adrenal gland; bile duct; bladder; blood cells; blood vessels; bone marrow; brain; breast; esophagus; eye; gallbladder; head&neck; heart; large intestine; small intestine; kidney; liver; lung; lymph nodes; peripheral nerve; ovary; pancreas; parathyroid gland; peritoneum; pituitary; placenta; pleura; prostate; skeletal muscle; skin; spinal cord; spleen; stomach; testis; thymus; thyroid; trachea; ureter; uterus. In case expression data for several samples of the same tissue type were available, the arithmetic mean of all respective samples was used for the calculation.

| SEQ ID NO | SEQUENCE | OVEREPRESSED (+) | HIGHLY OVEREXPRESSED (++) | VERY HIGHLY OVEREXPRESSED (+++) |
|---|---|---|---|---|
| 1 | AILAPPAILK | GC, OC, SCLC | CCC, MEL, NSCLC, OSCAR, PACA | GBC, UBC |
| 2 | GTVFVLLSK | | BRCA, UBC | HNSCC, NSCLC, OSCAR, RCC |
| 3 | VYIASSFKI | | HCC, PRCA | |
| 4 | IQAPALLKV | CLL, NHL | | |
| 5 | METADRPEW | | BRCA | PRCA |
| 6 | SHSLPAFTL | | | PRCA |
| 7 | IYIPTNSIYKF | | HCC, PRCA | |
| 8 | VIYNQTLMK | | GBC, HCC, RCC | CCC |
| 9 | LLGVVSHSV | | CLL | |
| 10 | ILMILQPQL | SCLC | GBC, GC, HCC, HNSCC, OC, OSCAR, PACA, RCC | NSCLC, UEC |
| 11 | TEIGTVIKLF | | BRCA | PRCA |
| 12 | RLQEGLAAL | SCLC | RCC | |
| 13 | LYDTVTHTF | GC, NHL, OC | CRC, GBC, PRCA | RCC |
| 14 | ILAPPQRISF | GC, NHL, OC | CRC, GBC, HNSCC, NSCLC, OSCAR, PACA, SCLC | MEL |
| 16 | NFHTLAQQLLF | | NSCLC, OSCAR | HNSCC |
| 17 | MVNWSLTNK | NHL, OC | GC, NSCLC, PACA, SCLC, UEC | HNSCC, NSCLC, OSCAR, UBC |
| 18 | SLSKLVATV | SCLC | CCC, GC, OSCAR, PACA | CRC |
| 19 | RILEVVRQPK | | CCC, HNSCC, NSCLC, OSCARSCLC, UBC | HCC, MEL |
| 20 | ILAPPAILK | BRCA, GC | CCC, MEL, NSCLC, OC, OSCAR, PACA, SCLC | UBC |
| 21 | MLSAQFILK | | NHL | CLL |

TABLE 9-continued

Expression scores. The table lists peptides that are very highly overexpressed in tumors compared to a panel of normal tissues (+++) or highly overexpressed in tumors compared to a panel of normal tissues (++) or overexpressed in tumors compared to a panel of normal tissues (+) according to the RNAseq experiments. The baseline for this score was calculated from measurements of the following relevant normal tissues: adipose tissue; adrenal gland; bile duct; bladder; blood cells; blood vessels; bone marrow; brain; breast; esophagus; eye; gallbladder; head&neck; heart; large intestine; small intestine; kidney; liver; lung; lymph nodes; peripheral nerve; ovary; pancreas; parathyroid gland; peritoneum; pituitary; placenta; pleura; prostate; skeletal muscle; skin; spinal cord; spleen; stomach; testis; thymus; thyroid; trachea; ureter; uterus. In case expression data for several samples of the same tissue type were available, the arithmetic mean of all respective samples was used for the calculation.

| SEQ ID NO | SEQUENCE | OVEREPRESSED (+) | HIGHLY OVEREXPRESSED (++) | VERY HIGHLY OVEREXPRESSED (+++) |
|---|---|---|---|---|
| 22 | RVIEVVMNSK | | GBM, HCC, HNSCC, MEL, NSCLC, OC, OSCAR, SCLC, UBC | GBC |
| 23 | AETKQFWSA | | | PRCA |
| 24 | LIYIPTNSIYK | | HCC, PRCA | |
| 28 | ATLQAVTLYKK | | MEL | |
| 29 | GTFIAPVMK | CCC | CRC, HNSCC, NSCLC, OSCAR, UBC | |
| 31 | VFLLLPYPRF | | RCC | |
| 32 | TAMTTLMAF | GBC, GC, NSCLC, OC, UEC | CCC, HNSCC, OSCAR, PACA, UBC | |
| 33 | AYIPFPPLI | GC, HCCNSCLC, PACA, UBC | PRCA, SCLC, UEC | |
| 34 | LLFKGLMWK | HCC | MEL | |
| 35 | SLATAISAK | CLL | NHL | |
| 36 | KEIEAQEAA | HCC, OC, UEC | CCC | |
| 37 | RLYSGSSFLY | | HNSCC | |
| 38 | AVVSHFILY | MEL | AML | |
| 39 | RELGVGIAL | UBC | HNSCC, OSCAR | |
| 40 | LYQTTIELF | | PRCA | |
| 41 | APQPRSLAA | GBC, HNSCC, NHL, OSCAR | MEL | |
| 42 | LLSRGILIL | | NHL, OC, UEC | |
| 43 | VFIPSVINL | | PRCA | |
| 44 | SLFPYFLNK | | MEL | |
| 45 | SLFPISLTV | | HNSCC, NSCLC, SCLC | |
| 47 | LYIFTTRPF | | MEL, NSCLC, SCLC | |
| 48 | TEMSVSALY | | BRCA | |
| 49 | IYFHLNNWTI | BRCA, OC, SCLC, UBC | GC, HNSCC, NSCLC, OSCAR, PACA, RCC, UEC | |
| 50 | KTIDLVIVR | | UBC | |
| 51 | SVFSLVHLFDK | | MEL, NHL, RCC | |
| 53 | TTLENLPQK | CCC, GBC, HNSCC, NSCLC, OSCAR, PACA | BRCA, MEL, NSCLC | |
| 55 | SPVSASWIL | UEC | MEL | |

TABLE 9-continued

Expression scores. The table lists peptides that are very highly overexpressed in tumors compared to a panel of normal tissues (+++) or highly overexpressed in tumors compared to a panel of normal tissues (++) or overexpressed in tumors compared to a panel of normal tissues (+) according to the RNAseq experiments. The baseline for this score was calculated from measurements of the following relevant normal tissues: adipose tissue; adrenal gland; bile duct; bladder; blood cells; blood vessels; bone marrow; brain; breast; esophagus; eye; gallbladder; head&neck; heart; large intestine; small intestine; kidney; liver; lung; lymph nodes; peripheral nerve; ovary; pancreas; parathyroid gland; peritoneum; pituitary; placenta; pleura; prostate; skeletal muscle; skin; spinal cord; spleen; stomach; testis; thymus; thyroid; trachea; ureter; uterus. In case expression data for several samples of the same tissue type were available, the arithmetic mean of all respective samples was used for the calculation.

| SEQ ID NO | SEQUENCE | OVEREPRESSED (+) | HIGHLY OVEREXPRESSED (++) | VERY HIGHLY OVEREXPRESSED (+++) |
|---|---|---|---|---|
| 56 | DVDIHKDLY | | PRCA | |
| 57 | IIIDRILLL | GC | NSCLC | |
| 58 | REQLDGATL | BRCA, GBC, MEL, NSCLC, UBC, UEC | GBC, GC, OSCAR, PACA | |
| 61 | GLIAFAIFK | UEC | CRC, GC | |
| 63 | MPANFETIGF | | OC | |
| 64 | LPTRSLPAF | | RCC | |
| 67 | GRFWLPFNF | HCC | BRCA, SCLC | |
| 68 | TVDKGELLY | CCC | NSCLC | |
| 69 | KYPTIICGF | GBC | CRC | |
| 70 | LIAGLIFLK | CCC, RCC | OC, UEC | |
| 72 | GSCSFALSR | BRCA, GC, PACA | UBC | |
| 75 | TTAAVYILK | NHL | CLL | |
| 76 | VQSGVPSRF | | GBC | |
| 77 | YPDVPIGQL | | CRC | |
| 78 | TPSHSTPSF | | PACA | |
| 79 | SLFRLSISF | | PRCA | |
| 80 | IFDLSDPRF | CRC, GBM, GC, HNSCC, MEL, NHL, NSCLC, OC, OSCAR | SCLC | |
| 81 | KLIAGLIFLK | CLL, RCC, UEC | OC | |
| 82 | VLQSLQHEL | | RCC | |
| 83 | EAAPNIMHY | | PRCA | |
| 84 | KEFAFLEHSL | CRC, GBC, HNSCC, NSCLC, UBC | OSCAR | |
| 85 | LPHPVNSGL | HNSCC | NSCLC | |
| 86 | VANDRLSFL | GBC, SCLC | PRCA | |
| 88 | KVGAVVHLK | CCC, GBC, MEL, UBC | | |
| 89 | SPSSPLLLA | PACA | | |
| 90 | LALLGAPPPK | NSCLC | | |
| 91 | RIVTYIVAK | OC, SCLC | | |
| 92 | LNFSDVFLY | CLL | | |
| 93 | SPIGLSLIL | MEL | | |

TABLE 9-continued

Expression scores. The table lists peptides that are very highly overexpressed in tumors compared to a panel of normal tissues (+++) or highly overexpressed in tumors compared to a panel of normal tissues (++) or overexpressed in tumors compared to a panel of normal tissues (+) according to the RNAseq experiments. The baseline for this score was calculated from measurements of the following relevant normal tissues: adipose tissue; adrenal gland; bile duct; bladder; blood cells; blood vessels; bone marrow; brain; breast; esophagus; eye; gallbladder; head&neck; heart; large intestine; small intestine; kidney; liver; lung; lymph nodes; peripheral nerve; ovary; pancreas; parathyroid gland; peritoneum; pituitary; placenta; pleura; prostate; skeletal muscle; skin; spinal cord; spleen; stomach; testis; thymus; thyroid; trachea; ureter; uterus. In case expression data for several samples of the same tissue type were available, the arithmetic mean of all respective samples was used for the calculation.

| SEQ ID NO | SEQUENCE | OVEREPRESSED (+) | HIGHLY OVEREXPRESSED (++) | VERY HIGHLY OVEREXPRESSED (+++) |
|---|---|---|---|---|
| 94 | AVFLGNPSNQK | NSCLC | | |
| 95 | YAFRNQTL | PRCA | | |
| 99 | RADEEQASF | BRCA, GBC, GC | | |
| 100 | SPAPSLARFLSL | BRCA, MEL | | |
| 101 | ATNSFLLIK | GBM | | |
| 102 | FLLLEKGGEL | CLL | | |
| 103 | RPWLSSPTGL | CCC, CLL, GBC, HNSCC, UBC | | |
| 104 | GSLQTLPPK | NSCLC | | |
| 106 | GLLDAFLRL | HCC | | |
| 108 | SLQESLPNA | AML | | |
| 109 | MPKLFLTAC | CLL | | |
| 110 | APSLARFLSL | MEL | | |
| 111 | RPIWDVRSA | HNSCC | | |
| 112 | ETYGTFVLR | PRCA | | |

Example 3

Validation of Peptides by IdentControl and CoElution

In order to validate the peptides according to the invention, all peptides were synthesized using standard and well-established solid phase peptide synthesis using the Fmoc-strategy. If necessary, stable isotope labeled (SIL-) amino acids were used to introduce a discriminating mass shift and allow for the use of these labeled peptides as internal standards (e.g. if a peptide was selected for identity confirmation in CoElution experiments). Identity and purity of each individual peptide were determined by mass spectrometry and analytical RP-HPLC. The peptides were obtained as white to off-white lyophilizes (trifluoro acetate salt) in purities of >50%. All TUMAPs are preferably administered as trifluoro-acetate salts or acetate salts, other salt-forms are also possible. The initial validation of peptides was achieved by IdentControl via spectral comparison. For this, synthetic peptides were used for validation of peptide identifications by acquisition of high-resolution reference MS2 spectra using matched fragmentation modes and collision energies as for acquisition of the natural spectra. Automated spectral comparison was performed using the sensitive metric of spectral correlation with a cutoff score determined to result in 90% sensitivity at <1% FDR based on a benchmark dataset comprising >10,000 manually validated spectra.

Ambiguous identifications were further subjected to validation in CoElution experiments.

TABLE 10

IdentControl Results. The spectral correlation indicates the similarity of the MS/MS spectra from the endogenous detected peptide compared to the synthetic peptide, the higher the value the more alike the spectra are. The peptide is validated when a threshold of 0.872 is met, or spectra are considered identical by manual review.

| SEQ ID NO | Sequence | Spectral Correlation |
|---|---|---|
| 1 | AILAPPAILK | 0.987 |
| 2 | GTVFVLLSK | 0.923 |
| 3 | VYIASSFKI | 0.988 |
| 4 | IQAPALLKV | 0.978 |
| 5 | METADRPEW | 0.982 |
| 6 | SHSLPAFTL | 0.911 |
| 7 | IYIPTNSIYKF | 0.941 |

TABLE 10-continued

IdentControl Results. The spectral correlation indicates the similarity of the MS/MS spectra from the endogenous detected peptide compared to the synthetic peptide, the higher the value the more alike the spectra are. The peptide is validated when a threshold of 0.872 is met, or spectra are considered identical by manual review.

| SEQ ID NO | Sequence | Spectral Correlation |
|---|---|---|
| 8 | VIYNQTLMK | 0.945 |
| 9 | LLGVVSHSV | 0.979 |
| 10 | ILMILQPQL | 0.967 |
| 11 | TEIGTVIKLF | 0.929 |
| 12 | RLQEGLAAL | 0.988 |
| 13 | LYDTVTHTF | 0.954 |
| 14 | ILAPPQRISF | 0.926 |
| 15 | SPVETRSLL | 0.900 |
| 16 | NFHTLAQQLLF | 0.964 |
| 17 | MVNWSLTNK | 0.945 |
| 18 | SLSKLVATV | 0.991 |
| 19 | RILEVVRQPK | 0.981 |
| 20 | ILAPPAILK | 0.960 |
| 21 | MLSAQFILK | 0.964 |
| 22 | RVIEVVMNSK | 0.925 |
| 23 | AETKQFWSA | 0.964 |
| 24 | LIYIPTNSIYK | 0.981 |
| 25 | GVCSTLTIK | 0.896 |
| 26 | ETNTIEFIY | 0.891 |
| 27 | SQAKQITIW | 0.952 |
| 28 | ATLQAVTLYKK | 0.919 |
| 29 | GTFIAPVMK | 0.908 |
| 30 | SLKSSILFL | 0.931 |
| 31 | VFLLLPYPRF | 0.936 |
| 32 | TAMTTLMAF | 0.920 |
| 33 | AYIPFPPLI | 0.958 |
| 34 | LLFKGLMWK | 0.923 |
| 35 | SLATAISAK | 0.959 |
| 36 | KEIEAQEAA | 0.981 |
| 37 | RLYSGSSFLY | 0.969 |
| 38 | AVVSHFILY | 0.966 |
| 39 | RELGVGIAL | 0.875 |
| 40 | LYQTTIELF | 0.873 |
| 41 | APQPRSLAA | 0.976 |
| 42 | LLSRGILIL | 0.975 |
| 43 | VFIPSVINL | 0.926 |
| 44 | SLFPYFLNK | 0.925 |
| 45 | SLFPISLTV | 0.875 |
| 46 | GESIYLLVRKW | 0.890 |
| 47 | LYIFTTRPF | 0.890 |
| 48 | TEMSVSALY | 0.883 |
| 49 | IYFHLNNWTI | 0.949 |
| 50 | KTIDLVIVR | 0.875 |
| 51 | SVFSLVHLFDK | 0.889 |
| 52 | SPLPHLGPL | 0.966 |
| 53 | TTLENLPQK | 0.875 |
| 54 | ASSPVILLL | 0.935 |
| 55 | SPVSASWIL | 0.913 |
| 56 | DVDIHKDLY | 0.959 |
| 57 | IIIDRILLL | 0.975 |
| 58 | REQLDGATL | 0.950 |
| 59 | AVDLGVLEL | 0.881 |
| 60 | VSPDEVLALW | 0.897 |
| 61 | GLIAFAIFK | 0.898 |
| 62 | SFSLLLPYL | 0.926 |
| 63 | MPANFETIGF | 0.941 |
| 64 | LPTRSLPAF | 0.918 |
| 65 | NSDLFYLLL | 0.898 |
| 66 | RPLILIRI | 0.911 |
| 67 | GRFWLPFNF | 0.958 |
| 68 | TVDKGELLY | 0.975 |
| 69 | KYPTIICGF | 0.975 |
| 70 | LIAGLIFLK | 0.953 |
| 71 | LIDSLLLLL | 0.914 |
| 72 | GSCSFALSR | 0.951 |
| 73 | NQKGLISL | 0.929 |
| 74 | TLNVLITL | 0.941 |
| 75 | TTAAVYILK | 0.918 |

TABLE 10-continued

IdentControl Results. The spectral correlation indicates the similarity of the MS/MS spectra from the endogenous detected peptide compared to the synthetic peptide, the higher the value the more alike the spectra are. The peptide is validated when a threshold of 0.872 is met, or spectra are considered identical by manual review.

| SEQ ID NO | Sequence | Spectral Correlation |
|---|---|---|
| 76 | VQSGVPSRF | 0.946 |
| 77 | YPDVPIGQL | 0.983 |
| 78 | TPSHSTPSF | 0.936 |
| 79 | SLFRLSISF | 0.908 |
| 80 | IFDLSDPRF | 0.944 |
| 81 | KLIAGLIFLK | 0.977 |
| 82 | VLQSLQHEL | 0.891 |
| 83 | EAAPNIMHY | 0.981 |
| 84 | KEFAFLEHSL | 0.877 |
| 85 | LPHPVNSGL | 0.939 |
| 86 | VANDRLSFL | 0.876 |
| 87 | LHLNPGLSF | 0.880 |
| 88 | KVGAVVHLK | 0.948 |
| 89 | SPSSPLLLLA | 0.911 |
| 90 | LALLGAPPPK | 0.929 |
| 91 | RIVTYIVAK | 0.972 |
| 92 | LNFSDVFLY | 0.890 |
| 93 | SPIGLSLIL | 0.941 |
| 94 | AVFLGNPSNQK | 0.916 |
| 95 | YAFRNQTL | 0.932 |
| 96 | HPRESLNMLVAF | 0.967 |
| 97 | ALIVLHLSL | 0.884 |
| 98 | FSEIFQDFL | 0.937 |
| 99 | RADEEQASF | 0.966 |
| 100 | SPAPSLARFLSL | 0.955 |
| 101 | ATNSFLLIK | 0.937 |
| 102 | FLLLEKGGEL | 0.888 |
| 103 | RPWLSSPTGL | 0.958 |
| 104 | GSLQTLPPK | 0.915 |
| 105 | LVFESVVAA | 0.937 |
| 106 | GLLDAFLRL | 0.980 |
| 107 | SVISVLTTPK | 0.893 |
| 108 | SLQESLPNA | 0.918 |
| 109 | MPKLFLTAC | 0.888 |
| 110 | APSLARFLSL | 0.920 |
| 111 | RPIWDVRSA | 0.956 |
| 112 | ETYGTFVLR | 0.965 |
| 113 | ALGPMAFRV | 0.972 |
| 114 | VPHHLLSSV | 0.891 |
| 115 | LWEEKPVCL | 0.972 |
| 116 | IYLTKSNLVNM | 0.919 |
| 117 | GEAAAARPV | 0.885 |
| 118 | RLLRLIPIL | 0.941 |
| 119 | VLHGLLFTL | 0.905 |
| 120 | APGPRSQGL | 0.935 |
| 121 | ILVTAWKGV | 0.971 |
| 122 | FTQKINSTW | 0.951 |
| 123 | TYLESSVRI | 0.969 |
| 124 | SPSSNSREL | 0.911 |
| 125 | ALAQGANLK | 0.967 |
| 126 | NPELLVILL | 0.914 |
| 127 | TVATQVATSK | 0.947 |
| 128 | MTFVPLLAR | 0.956 |
| 129 | IPISIFKMA | 0.894 |
| 130 | ITPDSIPSV | 0.947 |
| 131 | TILAKQNVL | 0.945 |
| 132 | LYLETRSEF | 0.976 |
| 133 | KFPPSASEF | 0.910 |
| 134 | MPCTTILRI | 0.957 |
| 135 | SADTAELLL | 0.973 |
| 136 | YSSEIVVDLY | 0.977 |
| 137 | MPIQVLKGL | 0.902 |
| 138 | RTLPLEGSPK | 0.981 |
| 139 | EEGRIITKW | 0.918 |
| 140 | QPAPQPLL | 0.973 |
| 141 | REVAGASAL | 0.873 |
| 142 | YMLEMDNSMKI | 0.914 |
| 143 | AVLGALLRH | 0.928 |

TABLE 10-continued

IdentControl Results. The spectral correlation indicates the similarity of the MS/MS spectra from the endogenous detected peptide compared to the synthetic peptide, the higher the value the more alike the spectra are. The peptide is validated when a threshold of 0.872 is met, or spectra are considered identical by manual review.

| SEQ ID NO | Sequence | Spectral Correlation |
|---|---|---|
| 144 | IIVPSFYK | 0.993 |
| 145 | HLFSVLSAI | 0.904 |
| 146 | KVLVDFLLK | 0.962 |
| 147 | VEAPHLPSF | 0.939 |
| 148 | SVYMATTLK | 0.941 |
| 149 | SMNSKALRWK | 0.890 |
| 150 | IVFLLQQGEK | 0.913 |
| 151 | AVFVNWEQTKK | 0.928 |
| 152 | KIMEILNLK | 0.970 |
| 153 | ALNLSRLTV | 0.966 |
| 154 | TVTSAIVNR | 0.948 |
| 155 | MPWVLMSPF | 0.962 |
| 156 | SLRVPSPAL | 0.968 |
| 157 | APLRAGWAA | 0.932 |
| 158 | FQLSGPVTF | 0.959 |
| 159 | ASAIPAGAK | 0.934 |
| 160 | EYLGSENVF | 0.956 |
| 161 | ILAASFQAR | 0.932 |
| 162 | LPVHGPLPLLL | 0.903 |
| 163 | LWALAIPSL | 0.996 |
| 164 | SHSSPTVSF | 0.973 |
| 165 | FYNPRPPLI | 0.940 |
| 166 | VIFLHQPPK | 0.962 |
| 167 | FALGPIIKQL | 0.867 |
| 168 | AEGPDHHSL | 0.904 |
| 169 | RPQGVGPAA | 0.900 |
| 170 | LLDSVVNILI | 0.895 |
| 171 | NVSFEVSLLY | 0.939 |
| 172 | LLYKTLIIL | 0.910 |
| 173 | IFTGRNAYF | 0.931 |
| 174 | LSGPVTFLR | 0.946 |
| 175 | MPFLKVPPL | 0.901 |
| 176 | AFLLSLISL | 0.913 |
| 177 | SYLKDHLSL | 0.959 |
| 178 | SLFGGLFTR | 0.925 |
| 179 | MIFSGVFLR | 0.962 |
| 180 | QYLTYYPSF | 0.950 |
| 181 | FDLNIGSAY | 0.896 |
| 182 | RPSLPCRSF | 0.921 |
| 183 | VFVISGSHLF | 0.936 |
| 184 | VVHGGMSIF | 0.953 |
| 185 | MPAFLSRASAL | 0.899 |
| 186 | SQIKSPVVF | 0.970 |
| 187 | RLCPAAPTGK | 0.926 |
| 188 | KLPFFTNFL | 0.951 |
| 189 | IWRALGSLF | 0.920 |
| 190 | STQSSLLYLK | 0.964 |
| 191 | APLLPGPAA | 0.944 |
| 192 | IPLHFSTAF | 0.951 |
| 193 | ILQLITVNR | 0.955 |
| 194 | VLYPSHSSF | 0.967 |
| 195 | AWNESSAWLL | 0.956 |
| 196 | NSENLLVY | 0.873 |
| 197 | HHTQLVFVF | 0.943 |
| 198 | MTYQQPFSNR | 0.959 |
| 199 | RAPLPLLLL | 0.962 |
| 200 | GLLGTLRVL | 0.945 |
| 201 | VWILQKVNLAF | 0.960 |
| 202 | KLLLLSSVK | 0.884 |
| 203 | AILVPQPPK | 0.961 |
| 204 | VVRASSGLK | 0.984 |
| 205 | SLIPIVPFKS | 0.949 |
| 206 | VEGVHFVQLL | 0.904 |
| 207 | LPALLRSL | 0.936 |
| 208 | YVGPTRLEL | 0.904 |
| 209 | AILLPQLPK | 0.976 |
| 210 | ASRIQVILL | 0.976 |
| 211 | VVTIVMHIYK | 0.940 |

TABLE 10-continued

IdentControl Results. The spectral correlation indicates the similarity of the MS/MS spectra from the endogenous detected peptide compared to the synthetic peptide, the higher the value the more alike the spectra are. The peptide is validated when a threshold of 0.872 is met, or spectra are considered identical by manual review.

| SEQ ID NO | Sequence | Spectral Correlation |
| --- | --- | --- |
| 212 | WETRLHNLW | 0.903 |
| 213 | TLLSFKTVLFK | 0.956 |
| 214 | RPSPVRVAAL | 0.874 |
| 215 | TPLTRTTL | 0.962 |
| 216 | ILRTVLPSL | 0.983 |

For further validation peptides were subjected to CoElution experiments using SIL internal standard peptides. To this end, SIL peptides were spiked into HLA peptidome extracts from samples and subjected to liquid chromatography-targeted mass spectrometry (LC-MS) to confirm peptide identity based on spectral similarity as well as CoElution in the retention time dimension. Spiked SIL-peptide amounts were adjusted to the peptide specific ionization factors (determined in calibration curves), if necessary. LC-MS was performed using pre-defined targeted MS2 scan events with non-overlapping isolation windows for SIL-peptide and natural peptide species to avoid co-fragmentation. To confirm isotopic purity and absence of co-fragmentation of SIL- and natural peptide, control experiments were performed in a non-HLA peptide containing tryptic matrix, which had to confirm absence of any unlabeled signal. Peptide detection and validation by CoElution was determined by manual expert review based on multiple pre-defined objective criteria, including dot product (dotP) of SIL peptide compared to unlabeled peptide MS2 traces, the presence of the most intense transitions in multiple consecutive scans and aligned peak apexes. A list which peptides were validated by CoElution can be found in table 11.

TABLE 11

Peptides with positive CoElution experiment

| SEQ ID NO | Sequence |
| --- | --- |
| 1 | AILAPPAILK |
| 2 | GTVFVLLSK |
| 3 | VYIASSFKI |
| 4 | IQAPALLKV |
| 5 | METADRPEW |
| 10 | ILMILQPQL |
| 11 | TEIGTVIKLF |
| 12 | RLQEGLAAL |
| 13 | LYDTVTHTF |
| 14 | ILAPPQRISF |
| 16 | NFHTLAQQLLF |
| 17 | MVNWSLTNK |
| 18 | SLSKLVATV |
| 19 | RILEVVRQPK |
| 20 | ILAPPAILK |
| 21 | MLSAQFILK |
| 22 | RVIEVVMNSK |
| 23 | AETKQFWSA |
| 24 | LIYIPTNSIYK |
| 25 | GVCSTLTIK |
| 28 | ATLQAVTLYKK |
| 29 | GTFIAPVMK |
| 31 | VFLLLPYPRF |
| 32 | TAMTTLMAF |
| 33 | AYIPFPPLI |
| 34 | LLFKGLMWK |
| 35 | SLATAISAK |
| 36 | KEIEAQEAA |
| 38 | AVVSHFILY |
| 39 | RELGVGIAL |
| 41 | APQPRSLAA |
| 44 | SLFPYFLNK |
| 50 | KTIDLVIVR |
| 53 | TTLENLPQK |
| 58 | REQLDGATL |
| 68 | TVDKGELLY |
| 69 | KYPTIICGF |
| 70 | LIAGLIFLK |
| 80 | IFDLSDPRF |
| 81 | KLIAGLIFLK |
| 84 | KEFAFLEHSL |
| 88 | KVGAVVHLK |
| 91 | RIVTYIVAK |
| 94 | AVFLGNPSNQK |
| 99 | RADEEQASF |
| 103 | RPWLSSPTGL |
| 107 | SVISVLTTPK |
| 109 | MPKLFLTAC |

TABLE 11-continued

Peptides with positive CoElution experiment

| SEQ ID NO | Sequence |
|---|---|
| 110 | APSLARFLSL |
| 113 | ALGPMAFRV |
| 114 | VPHHLLSSV |
| 115 | LWEEKPVCL |
| 116 | IYLTKSNLVNM |
| 122 | FTQKINSTW |
| 123 | TYLESSVRI |
| 124 | SPSSNSREL |
| 127 | TVATQVATSK |
| 128 | MTFVPLLAR |
| 132 | LYLETRSEF |
| 134 | MPCTTILRI |
| 135 | SADTAELLL |
| 138 | RTLPLEGSPK |
| 139 | EEGRIITKW |
| 143 | AVLGALLRH |
| 144 | IIVPSFYK |
| 145 | HLFSVLSAI |
| 146 | KVLVDFLLK |
| 147 | VEAPHLPSF |
| 148 | SVYMATTLK |
| 149 | SMNSKALRWK |
| 152 | KIMEILNLK |
| 158 | FQLSGPVTF |
| 169 | RPQGVGPAA |
| 173 | IFTGRNAYF |
| 177 | SYLKDHLSL |
| 179 | MIFSGVFLR |
| 180 | QYLTYYPSF |
| 182 | RPSLPCRSF |
| 185 | MPAFLSRASAL |
| 186 | SQIKSPVVF |
| 188 | KLPFFTNFL |
| 192 | IPLHFSTAF |
| 193 | ILQLITVNR |
| 198 | MTYQQPFSNR |
| 203 | AILVPQPPK |
| 204 | VVRASSGLK |

TABLE 11-continued

Peptides with positive CoElution experiment

| SEQ ID NO | Sequence |
|---|---|
| 212 | WETRLHNLW |
| 213 | TLLSFKTVLFK |
| 214 | RPSPVRVAAL |

Example 4

In Vitro Immunogenicity for MHC Class I Presented Peptides

In order to obtain information regarding the immunogenicity of the TUMAPs of the present invention, the inventors performed investigations using an in vitro T cell priming assay based on repeated stimulations of CD8+ T cells with artificial antigen presenting cells (aAPCs) loaded with peptide/MHC complexes and anti-CD28 antibody. This way the inventors could show immunogenicity for MHC class I restricted TUMAPs of the invention, demonstrating that these peptides are T cell epitopes against which CD8+ precursor T cells exist in humans (Table 12A through 12E).

In Vitro Priming of CD8+ T Cells

In order to perform in vitro stimulations by artificial antigen presenting cells loaded with peptide-MHC complex (pMHC) and anti-CD28 antibody, the inventors first isolated CD8+ T cells from fresh HLA-A*02, HLA-A*03, HLA-A*24, HLA-B*07 or HLA-B*44 leukapheresis products via positive selection using CD8 microbeads (Miltenyi Biotec, Bergisch-Gladbach, Germany) of healthy donors obtained from the University clinics Mannheim, Germany, after informed consent.

PBMCs and isolated CD8+ lymphocytes were incubated in T cell medium (TCM) until use consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nürnberg, Germany) were also added to the TCM at this step.

Generation of pMHC/anti-CD28 coated beads, T cell stimulations and readout was performed in a highly defined in vitro system using four different pMHC molecules per stimulation condition and 8 different pMHC molecules per readout condition.

The purified co-stimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.6 µm diameter streptavidin coated polystyrene particles (Bangs Laboratories, Illinois, USA).

pMHC used for positive and negative control stimulations were A*02:01/MLA-001 (peptide ELAGIGILTV (SEQ ID NO: 217) from modified Melan-A/MART-1) and A*02:01/DDX5-001 (YLLPAIVHI from DDX5, SEQ ID NO: 218), respectively.

800.000 beads/200 µl were coated in 96-well plates in the presence of 4×12.5 ng different biotin-pMHC, washed and 600 ng biotin anti-CD28 were added subsequently in a volume of 200 µl. Stimulations were initiated in 96-well plates by co-incubating $1\times10^6$ CD8+ T cells with $2\times10^5$ washed coated beads in 200 µl TCM supplemented with 5 ng/ml IL-12 (PromoCell) for 3 days at 37° C. Half of the medium was then exchanged by fresh TCM supplemented with 80 U/ml IL-2 and incubating was continued for 4 days at 37° C. This stimulation cycle was performed for a total of three times. For the pMHC multimer readout using 8 different pMHC molecules per condition, a two-dimensional combinatorial coding approach was used as previously described (Andersen et al., 2012) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oregon, USA). In vitro priming of specific multimer+CD8+ lymphocytes was detected by comparing to negative control stimulations. Immunogenicity for a given antigen was detected if at least one evaluable in vitro stimulated well of one healthy donor was found to contain a specific CD8+ T cell line after in vitro stimulation (i.e. this well contained at least 1% of specific multimer+ among CD8+ T cells and the percentage of specific multimer+ cells was at least 10× the median of the negative control stimulations).

In Vitro Immunogenicity

Figure 5A:
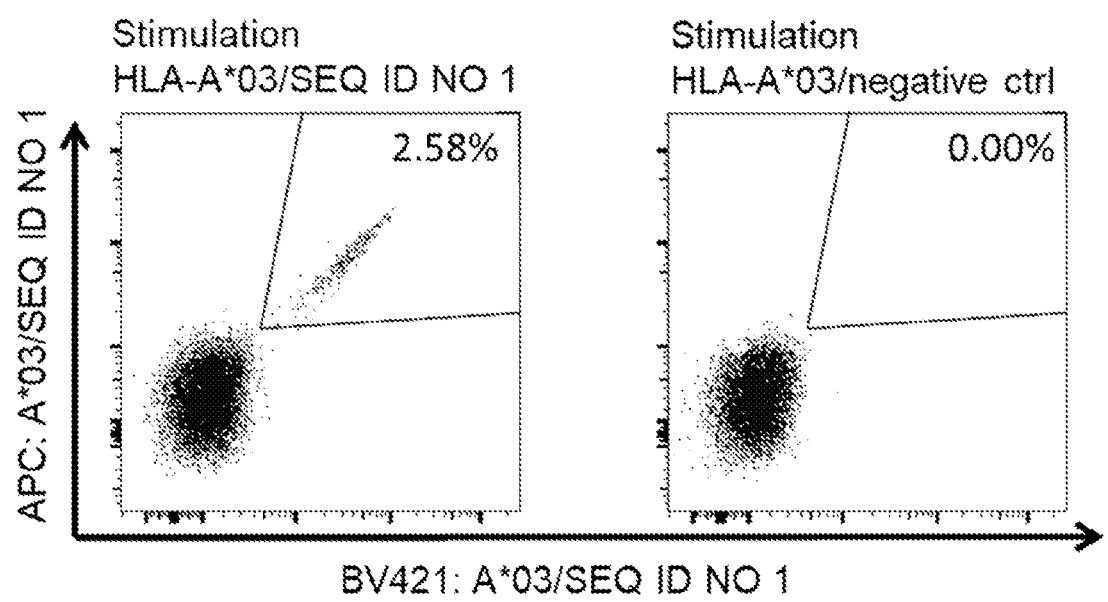
FIGS. 5A through 5E show exemplary results of peptide-specific in vitro CD8$^+$ T cell responses of healthy HLA-A*02+, A*03+, A*24+ or B*44+ donors. CD8+ T cells were primed using artificial APCs coated with anti-CD28 mAb and HLA-A*02, A*03, A*24 or B*44 in complex with SEQ ID NO 1 (A, left panel), SEQ ID NO 3 (B, left panel), SEQ ID NO 4 (C, left panel), SEQ ID NO 5 (D, left panel) or SEQ ID NO 11 (E, left panel). After three cycles of stimulation, the detection of peptide-reactive cells was performed by 2D multimer staining with A*03/SEQ ID NO 1 (A), A*24/SEQ ID NO 3 (B), A*02/SEQ ID NO 4 (C), B*44/SEQ ID NO 5 (D) or B*44/SEQ ID NO 11 (E). Right panels (A, B, C, D and E) show control staining of cells stimulated with irrelevant HLA/peptide complexes of the same allotype as the complex of interest. Viable single cells were gated for CD8+ lymphocytes. Boolean gates helped excluding false-positive events detected with multimers specific for different peptides. Frequencies of specific multimer+ cells among CD8+ lymphocytes are indicated.
Figure 5B:
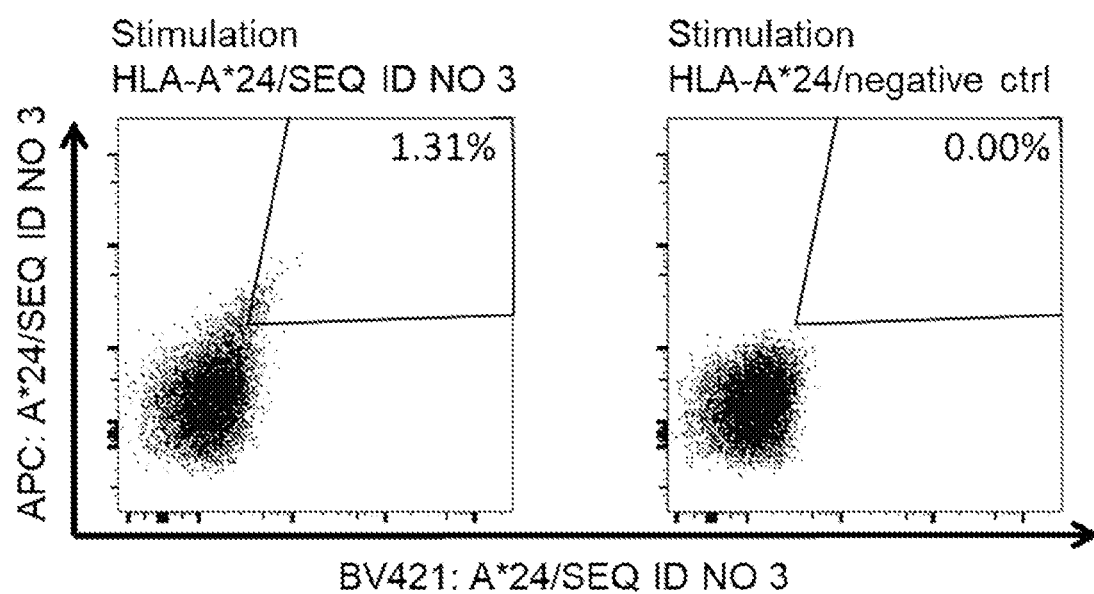
Figure 5C:
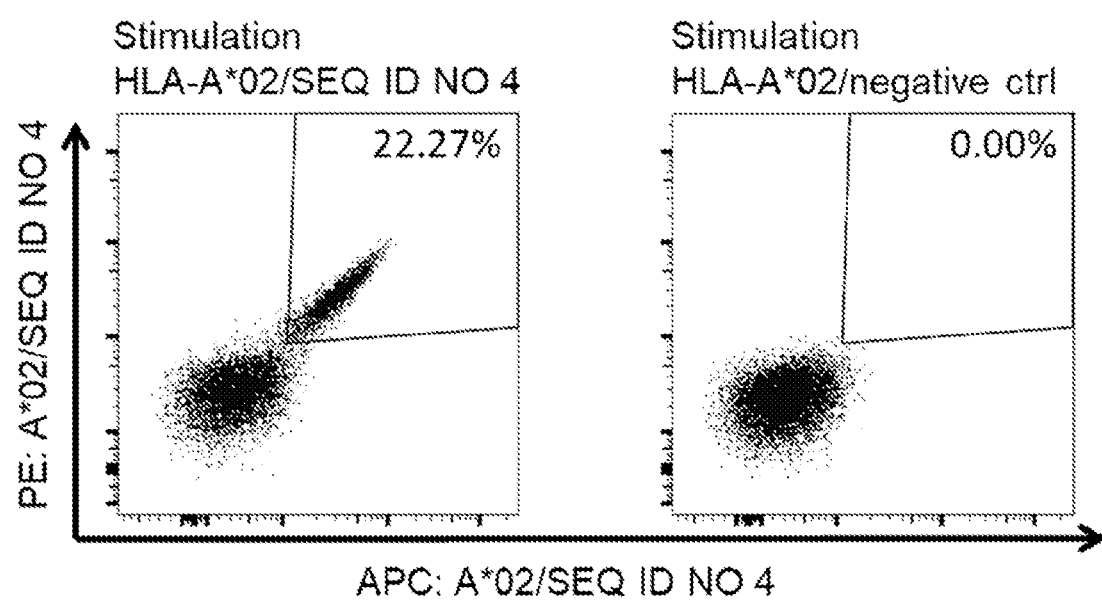
Figure 5D:
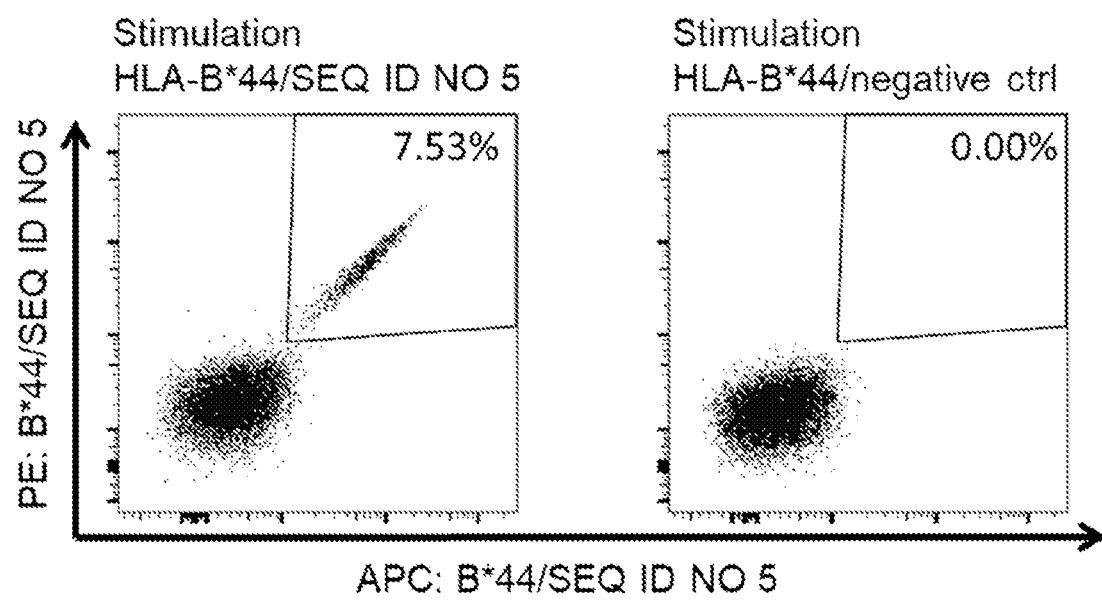
Figure 5E:
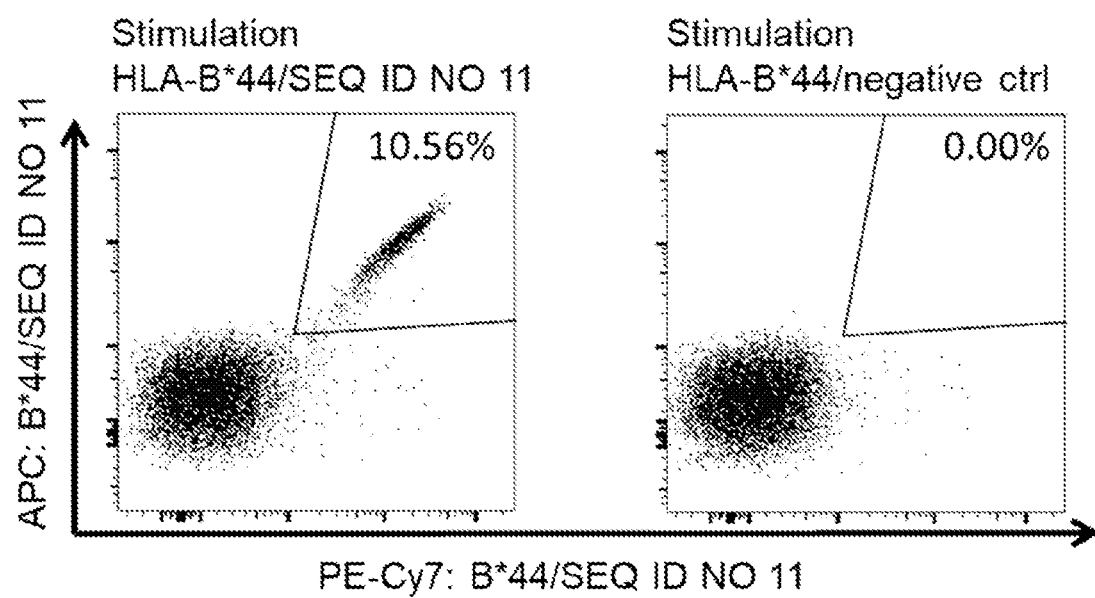

For tested HLA class I peptides, in vitro immunogenicity could be demonstrated by generation of peptide specific T cell lines. Exemplary flow cytometry results after TUMAP-specific multimer staining for 5 peptides of the invention are shown in FIG. 5 together with corresponding negative controls. Results for 33 peptides from the invention are summarized in Table 12A through 12E.

TABLE 12A in vitro immunogenicity of HLA-A*02 peptides of the invention
Exemplary results of in vitro immunogenicity experiments conducted by the applicant for HLA-A*02 restricted peptides of the invention. Results of in vitro immunogenicity experiments are indicated. Percentage of positive wells and donors (among evaluable) are summarized as indicated <20% = +; 20%-49% = ++; 50%-69% = +++; >=70% = ++++

| SEQ ID NO | Sequence | Wells positive [%] |
|---|---|---|
| 4 | IQAPALLKV | ++ |
| 10 | ILMILQPQL | + |
| 12 | RLQEGLAAL | + |
| 18 | SLSKLVATV | + |
| 113 | ALGPMAFRV | ++ |
| 188 | KLPFFTNFL | + |

TABLE 12B in vitro immunogenicity of HLA-A*03 peptides of the invention
Exemplary results of in vitro immunogenicity experiments conducted by the applicant for HLA-A*03 restricted peptides of the invention. Results of in vitro immunogenicity experiments are indicated. Percentage of positive wells and donors (among evaluable) are summarized as indicated <20% = +; 20%-49% = ++; 50%-69% = +++; >=70% = ++++

| SEQ ID NO | Sequence | Wells positive [%] |
|---|---|---|
| 1 | AILAPPAILK | + |
| 2 | GTVFVLLSK | + |
| 17 | MVNWSLTNK | ++++ |
| 20 | ILAPPAILK | ++ |
| 21 | MLSAQFILK | + |
| 22 | RVIEVVMNSK | + |
| 25 | GVCSTLTIK | + |
| 38 | AVVSHFILY | + |
| 50 | KTIDLVIVR | + |
| 91 | RIVTYIVAK | + |
| 94 | AVFLGNPSNQK | + |
| 128 | MTFVPLLAR | + |
| 146 | KVLVDFLLK | + |
| 148 | SVYMATTLK | + |
| 149 | SMNSKALRWK | ++ |

TABLE 12C in vitro immunogenicity of HLA-A*24 peptides of the invention
Exemplary results of in vitro immunogenicity experiments conducted by the applicant for HLA-A*24 restricted peptides of the invention. Results of in vitro immunogenicity experiments are indicated. Percentage of positive wells and donors (among evaluable) are summarized as indicated <20% = +; 20%-49% = ++; 50%-69% = +++; >=70% = ++++

| SEQ ID NO | Sequence | Wells positive [%] |
|---|---|---|
| 3 | VYIASSFKI | + |
| 16 | NFHTLAQQLLF | + |
| 31 | VFLLLPYPRF | +++ |
| 33 | AYIPFPPLI | ++ |
| 116 | IYLTKSNLVNM | + |
| 123 | TYLESSVRI | ++ |
| 132 | LYLETRSEF | + |
| 180 | QYLTYYPSF | + |

TABLE 12D in vitro immunogenicity of HLA-B*07 peptides of
the invention
Exemplary results of in vitro immunogenicity
experiments conducted by the applicant for
HLA-B*07 restricted peptides of the invention.
Results of in vitro immunogenicity experiments
are indicated. Percentage of positive wells and
donors (among evaluable) are summarized as
indicated <20% = +; 20%-49% = ++; 50%-69% = +++;
>=70% = ++++

| SEQ ID NO | Sequence | Wells positive [%] |
| --- | --- | --- |
| 41 | APQPRSLAA | + |
| 109 | MPKLFLTAC | + |
| 110 | APSLARFLSL | ++++ |
| 114 | VPHHLLSSV | + |
| 124 | SPSSNSREL | + |
| 134 | MPCTTILRI | + |
| 169 | RPQGVGPAA | ++ |
| 182 | RPSLPCRSF | ++ |
| 185 | MPAFLSRASAL | ++ |
| 214 | RPSPVRVAAL | + |

TABLE 12E in vitro immunogenicity of HLA-B*44 peptides
of the invention
Exemplary results of in vitro immunogenicity
experiments conducted by the applicant for
HLA-B*44 restricted peptides of the invention.
Results of in vitro immunogenicity experiments
are indicated. Percentage of positive wells and
donors (among evaluable) are summarized as
indicated <20% = +; 20%-49% = ++; 50%-69% = +++;
>=70% = ++++

| SEQ ID NO | Sequence | Wells positive [%] |
| --- | --- | --- |
| 5 | METADRPEW | + |
| 11 | TEIGTVIKLF | ++ |
| 39 | RELGVGIAL | + |
| 212 | WETRLHNLW | ++ |

Example 5

MHC Binding Assays

Candidate peptides for T cell based therapies according to the present invention were further tested for their MHC binding capacity (affinity). The individual peptide-MHC complexes were produced by UV-ligand exchange, where a UV-sensitive peptide is cleaved upon UV-irradiation and exchanged with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (B2m) of stabilized MHC complexes. The assay was performed as generally described in Rodenko et al. (Rodenko et al., 2006).

96 well MAXISorp plates (NUNC) were coated over night with 2 μg/ml streptavidin in PBS at room temperature, washed 4× and blocked for 1 h at 37° C. in 2% BSA containing blocking buffer. Refolded HLA-A*02: 01/MLA-001 monomers served as standards, covering the range of 15-500 ng/ml. Peptide-MHC monomers of the UV-exchange reaction were diluted 100-fold in blocking buffer. Samples were incubated for 1 h at 37° C., washed four times, incubated with 2 μg/ml HRP conjugated anti-B2m for 1 h at 37° C., washed again and detected with TMB solution that is stopped with $NH_2SO_4$. Absorption was measured at 450 nm. Candidate peptides that show a high exchange yield (preferably higher than 50%, most preferred higher than 75%) are generally preferred for a generation and production of antibodies or fragments thereof, and/or T cell receptors or fragments thereof, as they show sufficient avidity to the MHC molecules and prevent dissociation of the MHC complexes. MHC-peptide binding results for 208 peptides from the invention are summarized in Table 13A through G.

TABLE 13A

MHC class I binding scores.
Binding of HLA-class I restricted peptides to
HLA-A*01:01 was ranged by peptide exchange yield:
≥10% = +; ≥20% = ++; ≥50% = +++; ≥75% = ++++

| SEQ ID NO | Sequence | Peptide exchange |
| --- | --- | --- |
| 26 | ETNTIEFIY | ++++ |
| 54 | ASSPVILLL | ++ |
| 56 | DVDIHKDLY | ++++ |
| 60 | VSPDEVLALW | ++ |
| 65 | NSDLFYLLL | ++++ |
| 68 | TVDKGELLY | ++++ |
| 71 | LIDSLLLLL | +++ |
| 83 | EAAPNIMHY | ++ |
| 92 | LNFSDVFLY | ++ |
| 98 | FSEIFQDFL | +++ |
| 99 | RADEEQASF | ++ |
| 122 | FTQKINSTW | ++ |
| 135 | SADTAELLL | ++ |
| 136 | YSSEIWDLY | ++++ |
| 171 | NVSFEVSLLY | ++++ |
| 196 | NSENLLVY | +++ |

TABLE 13B

MHC class I binding scores.
Binding of HLA-class I restricted peptides to
HLA-A*02:01 was ranged by peptide exchange yield:
≥10% = +; ≥20% = ++; ≥50% = +++; ≥75% = ++++

| SEQ ID NO | Sequence | Peptide exchange |
| --- | --- | --- |
| 4 | IQAPALLKV | ++++ |
| 9 | LLGVVSHSV | ++++ |
| 10 | ILMILQPQL | ++++ |

TABLE 13B-continued

MHC class I binding scores.
Binding of HLA-class I restricted peptides to
HLA-A*02:01 was ranged by peptide exchange yield:
≥10% = +; ≥20% = ++; ≥50% = +++; ≥75% = ++++

| SEQ ID NO | Sequence | Peptide exchange |
| --- | --- | --- |
| 12 | RLQEGLAAL | ++++ |
| 18 | SLSKLVATV | ++++ |
| 30 | SLKSSILFL | +++ |
| 42 | LLSRGILIL | ++++ |
| 45 | SLFPISLTV | ++++ |
| 57 | IIIDRILLL | ++++ |
| 74 | TLNVLITL | ++ |
| 82 | VLQSLQHEL | ++++ |
| 97 | ALIVLHLSL | ++ |
| 102 | FLLLEKGGEL | ++++ |
| 105 | LVFESVVAA | ++++ |
| 106 | GLLDAFLRL | ++++ |
| 108 | SLQESLPNA | +++ |
| 113 | ALGPMAFRV | ++++ |
| 118 | RLLRLIPIL | ++++ |
| 121 | ILVTAWKGV | +++ |
| 130 | ITPDSIPSV | +++ |
| 142 | YMLEMDNSMKI | ++++ |
| 145 | HLFSVLSAI | ++++ |
| 153 | ALNLSRLTV | ++++ |
| 167 | FALGPIIKQL | +++ |
| 170 | LLDSWNILI | ++++ |
| 188 | KLPFFTNFL | ++++ |
| 200 | GLLGTLRVL | ++++ |

TABLE 13C

MHC class I binding scores.
Binding of HLA-class I restricted peptides to
HLA-A*03:01 was ranged by peptide exchange yield:
≥10% = +; ≥20% = ++; ≥50% = +++; ≥75% = ++++

| SEQ ID NO | Sequence | Peptide exchange |
| --- | --- | --- |
| 1 | AILAPPAILK | ++++ |
| 2 | GTVFVLLSK | ++ |
| 8 | VIYNQTLMK | ++++ |
| 17 | MVNWSLTNK | ++++ |
| 19 | RILEVVRQPK | ++++ |
| 20 | ILAPPAILK | ++++ |
| 21 | MLSAQFILK | ++++ |
| 22 | RVIEVVMNSK | ++++ |
| 24 | LIYIPTNSIYK | ++++ |
| 25 | GVCSTLTIK | ++++ |
| 28 | ATLQAVTLYKK | ++++ |
| 29 | GTFIAPVMK | ++++ |
| 34 | LLFKGLMWK | ++++ |
| 35 | SLATAISAK | +++ |
| 37 | RLYSGSSFLY | ++++ |
| 38 | AVVSHFILY | +++ |
| 44 | SLFPYFLNK | ++++ |
| 50 | KTIDLVIVR | ++++ |
| 51 | SVFSLVHLFDK | ++++ |
| 53 | TTLENLPQK | +++ |
| 70 | LIAGLIFLK | +++ |
| 72 | GSCSFALSR | ++++ |
| 75 | TTAAVYILK | +++ |
| 81 | KLIAGLIFLK | +++ |
| 88 | KVGAVVHLK | +++ |
| 90 | LALLGAPPPK | ++ |
| 91 | RIVTYIVAK | +++ |
| 94 | AVFLGNPSNQK | ++++ |
| 101 | ATNSFLLIK | ++++ |
| 104 | GSLQTLPPK | +++ |
| 107 | SVISVLTTPK | ++++ |
| 112 | ETYGTFVLR | +++ |
| 125 | ALAQGANLK | +++ |
| 127 | TVATQVATSK | +++ |
| 128 | MTFVPLLAR | ++++ |
| 138 | RTLPLEGSPK | +++ |
| 143 | AVLGALLRH | ++++ |
| 144 | IIVPSFYK | +++ |
| 146 | KVLVDFLLK | +++ |
| 148 | SVYMATTLK | ++++ |
| 149 | SMNSKALRWK | +++ |
| 150 | IVFLLQQGEK | +++ |
| 151 | AVFVNWEQTKK | ++++ |

TABLE 13C-continued

MHC class I binding scores.
Binding of HLA-class I restricted peptides to
HLA-A*03:01 was ranged by peptide exchange yield:
≥10% = +; ≥20% = ++; ≥50% = +++; ≥75% = ++++

| SEQ ID NO | Sequence | Peptide exchange |
|---|---|---|
| 152 | KIMEILNLK | ++++ |
| 154 | TVTSAIVNR | +++ |
| 159 | ASAIPAGAK | +++ |
| 161 | ILAASFQAR | +++ |
| 166 | VIFLHQPPK | ++++ |
| 174 | LSGPVTFLR | +++ |
| 178 | SLFGGLFTR | ++++ |
| 179 | MIFSGVFLR | ++++ |
| 187 | RLCPAAPTGK | ++++ |
| 190 | STQSSLLYLK | +++ |
| 193 | ILQLITVNR | +++ |
| 198 | MTYQQPFSNR | ++++ |
| 202 | KLLLLSSVK | +++ |
| 203 | AILVPQPPK | +++ |
| 204 | VVRASSGLK | +++ |
| 205 | SLIPIVPFKS | ++ |
| 209 | AILLPQLPK | ++++ |
| 213 | TLLSFKTVLFK | ++++ |

TABLE 13D

MHC class I binding scores.
Binding of HLA-class I restricted peptides to
HLA-A*24:02 was ranged by peptide exchange yield:
10% = +; 20% = ++; 50% = +++; 75% = ++++

| SEQ ID NO | Sequence | Peptide exchange |
|---|---|---|
| 3 | VYIASSFKI | ++++ |
| 6 | SHSLPAFTL | ++ |
| 7 | IYIPTNSIYKF | ++++ |
| 13 | LYDTVTHTF | ++++ |
| 14 | ILAPPQRISF | ++++ |
| 16 | NFHTLAQQLLF | ++++ |
| 31 | VFLLLPYPRF | ++++ |
| 33 | AYIPFPPLI | ++++ |
| 40 | LYQTTIELF | ++++ |
| 43 | VFIPSVINL | ++++ |
| 47 | LYIFTTRPF | ++++ |
| 49 | IYFHLNNWTI | ++++ |

TABLE 13D-continued

MHC class I binding scores.
Binding of HLA-class I restricted peptides to
HLA-A*24:02 was ranged by peptide exchange yield:
10% = +; 20% = ++; 50% = +++; 75% = ++++

| SEQ ID NO | Sequence | Peptide exchange |
|---|---|---|
| 62 | SFSLLLPYL | +++ |
| 67 | GRFWLPFNF | ++ |
| 69 | KYPTIICGF | ++++ |
| 76 | VQSGVPSRF | ++ |
| 80 | IFDLSDPRF | ++ |
| 87 | LHLNPGLSF | ++ |
| 115 | LVVEEKPVCL | ++ |
| 116 | IYLTKSNLVNM | ++++ |
| 123 | TYLESSVRI | ++++ |
| 132 | LYLETRSEF | ++++ |
| 133 | KFPPSASEF | ++++ |
| 158 | FQLSGPVTF | ++ |
| 160 | EYLGSENVF | +++ |
| 163 | LWALAIPSL | +++ |
| 164 | SHSSPTVSF | ++ |
| 165 | FYNPRPPLI | ++++ |
| 173 | IFTGRNAYF | ++++ |
| 177 | SYLKDHLSL | ++++ |
| 180 | QYLTYYPSF | ++++ |
| 183 | VFVISGSHLF | ++++ |
| 186 | SQIKSPVVF | + |
| 189 | IWRALGSLF | ++++ |
| 194 | VLYPSHSSF | ++ |
| 195 | AWNESSAWLL | ++++ |
| 201 | VWILQKVNLAF | +++ |

TABLE 13E

MHC class I binding scores.
Binding of HLA-class I restricted peptides to
HLA-B*07:0 was ranged by peptide exchange yield:
≥10% = +; ≥20% = ++; ≥50% = +++; ≥75% = ++++

| SEQ ID NO | Sequence | Peptide exchange |
|---|---|---|
| 15 | SPVETRSLL | +++ |
| 41 | APQPRSLAA | ++++ |
| 52 | SPLPHLGPL | +++ |
| 55 | SPVSASWIL | ++++ |
| 59 | AVDLGVLEL | +++ |
| 63 | MPANFETIGF | ++++ |

TABLE 13E-continued

MHC class I binding scores.
Binding of HLA-class I restricted peptides to
HLA-B*07:0 was ranged by peptide exchange yield:
≥10% = +; ≥20% = ++; ≥50% = +++; ≥75% = ++++

| SEQ ID NO | Sequence | Peptide exchange |
|---|---|---|
| 64 | LPTRSLPAF | +++ |
| 66 | RPLILIRI | ++ |
| 77 | YPDVPIGQL | +++ |
| 78 | TPSHSTPSF | +++ |
| 85 | LPHPVNSGL | +++ |
| 89 | SPSSPLLLLA | +++ |
| 93 | SPIGLSLIL | ++++ |
| 96 | HPRESLNMLVAF | ++++ |
| 100 | SPAPSLARFLSL | ++++ |
| 103 | RPWLSSPTGL | ++++ |
| 109 | MPKLFLTAC | ++++ |
| 110 | APSLARFLSL | ++++ |
| 111 | RPIWDVRSA | ++++ |
| 114 | VPHHLLSSV | ++++ |
| 120 | APGPRSQGL | +++ |
| 124 | SPSSNSREL | +++ |
| 126 | NPELLVILL | +++ |
| 129 | IPISIFKMA | +++ |
| 134 | MPCTTILRI | ++++ |
| 137 | MPIQVLKGL | ++++ |
| 140 | QPAPQPLL | +++ |
| 155 | MPWVLMSPF | ++++ |
| 156 | SLRVPSPAL | +++ |
| 157 | APLRAGWAA | ++++ |
| 162 | LPVHGPLPLLL | +++ |
| 169 | RPQGVGPAA | ++++ |
| 175 | MPFLKVPPL | ++++ |
| 182 | RPSLPCRSF | +++ |
| 184 | VVHGGMSIF | ++ |
| 185 | MPAFLSRASAL | ++++ |
| 191 | APLLPGPAA | ++++ |
| 192 | IPLHFSTAF | ++++ |
| 199 | RAPLPLLLL | +++ |
| 207 | LPALLRSL | ++++ |
| 208 | YVGPTRLEL | ++++ |
| 210 | ASRIQVILL | +++ |

TABLE 13E-continued

MHC class I binding scores.
Binding of HLA-class I restricted peptides to
HLA-B*07:0 was ranged by peptide exchange yield:
≥10% = +; ≥20% = ++; ≥50% = +++; ≥75% = ++++

| SEQ ID NO | Sequence | Peptide exchange |
|---|---|---|
| 214 | RPSPVRVAAL | ++++ |
| 215 | TPLTRTTL | +++ |

TABLE 13F

MHC class I binding scores.
Binding of HLA-class I restricted peptides to
HLA-B*08:01 was ranged by peptide exchange yield:
≥10% = +; ≥20% = ++; ≥50% = +++; ≥75% = ++++

| SEQ ID NO | Sequence | Peptide exchange |
|---|---|---|
| 32 | TAMTTLMAF | +++ |
| 73 | NQKGLISL | +++ |
| 86 | VANDRLSFL | +++ |
| 95 | YAFRNQTL | +++ |
| 131 | TILAKQNVL | +++ |
| 216 | ILRTVLPSL | +++ |

TABLE 13G

MHC class I binding scores.
Binding of HLA-class I restricted peptides to
HLA-B*44:05 was ranged by peptide exchange yield:
10% = +; 20% = ++; 50% = +++; 75% = ++++

| SEQ ID NO | Sequence | Peptide exchange |
|---|---|---|
| 5 | METADRPEW | ++++ |
| 11 | TEIGTVIKLF | ++++ |
| 23 | AETKQFWSA | ++++ |
| 27 | SQAKQITIW | ++++ |
| 36 | KEIEAQEAA | ++++ |
| 39 | RELGVGIAL | ++++ |
| 48 | TEMSVSALY | ++++ |
| 58 | REQLDGATL | ++++ |
| 84 | KEFAFLEHSL | ++++ |
| 117 | GEAAAARPV | +++ |
| 139 | EEGRIITKW | ++++ |
| 141 | REVAGASAL | +++ |
| 147 | VEAPHLPSF | ++++ |
| 168 | AEGPDHHSL | ++++ |
| 181 | FDLNIGSAY | ++++ |
| 206 | VEGVHFVQLL | ++++ |
| 212 | WETRLHNLW | ++++ |

REFERENCE LIST

Alcoser, S. Y. et al., BMC.Biotechnol. 11 (2011): 124.
Allison, J. P. et al., Science 270 (1995): 932-933.
Andersen, R. S. et al., Nat Protoc. 7 (2012): 891-902.
Appay, V. et al., Eur.J Immunol. 36 (2006): 1805-1814.
Balbás R and Lorence A. "Methods in Molecular Biology Recombinant Gene Expression, Reviews and Protocols" (2004).
Banchereau, J. et al., Cell 106 (2001): 271-274.
Banker, G. and Rhodes, C. "Modern Pharmaceutics", CRC Press (2002).
Beggs, J. D. et al., Nature 275 (1978): 104-109.
Benjamini, Y. et al., Journal of the Royal Statistical Society.Series B (Methodological), Vol. 57 (1995): 289-300.
Berge, S. M. et al., Journal of Pharmaceutical Science 66 (1977): 1-19.
Better, M. et al., Science 240 (1988): 1041-1043.
Boulianne, G. L. et al. Nature 312 (1984): 643-646.
Boulter, J. M. et al., Protein Eng 16 (2003): 707-711.
Brossart, P. et al., Blood 90 (1997): 1594-1599.
Bruckdorfer, T. et al., Curr.Pharm.Biotechnol. 5 (2004): 29-43.
Cabilly, S. et al. Proc Natl Acad Sci 81 (1984): 3273-3277.
Card, K. F. et al., Cancer Immunol. Immunother. 53 (2004): 345-357.
Cohen, C. J. et al., J Immunol. 170 (2003b): 4349-4361.
Cohen, C. J. et al., J Mol.Recognit. 16 (2003a): 324-332.
Cohen, S. N. et al., Proc. Natl.Acad.Sci.U.S.A 69 (1972): 2110-2114.
Coligan, J. E. et al., Current Protocols in Protein Science (1995).
Colombetti, S. et al., J Immunol. 176 (2006): 2730-2738
Dayhoff, M. O. et al., "The Atlas of Protein Sequence and Structure" Natl Biomedical Research (1965).
Dengjel, J. et al., Clin Cancer Res 12 (2006): 4163-4170.
Denkberg, G. et al., J Immunol. 171 (2003): 2197-2207.
Falk, K. et al., Nature 351 (1991): 290-296.
Follenzi, A. et al., Nat Genet. 25 (2000): 217-222.
Fong, L. et al., Proc.Natl.Acad.Sci.U.S.A 98 (2001): 8809-8814.
Forsey, R. W. et al., Biotechnol.Lett. 31 (2009): 819-823.
Gabrilovich, D. I. et al., Nat.Med 2 (1996): 1096-1103.
Gattinoni, L. et al., Nat.Rev.Immunol. 6 (2006): 383-393.
Gennaro, A. "Remington's: The Science and Practice of Pharmacy", Lippincott Williams & Wilkins (1997).
Gilliland, D. G. et al., Proc Natl Acad Sci 77 (1980): 4539
Green, M. R. et al., Molecular Cloning, A Laboratory Manual 4th (2012).
Greenfield, E. A., Antibodies: A Laboratory Manual 2nd (2014).
Guo, H. H. et al., Proc Natl Acad Sci 101 (25): 9205-9210 (2004).
Gustafsson, C. et al., Trends Biotechnol. 22 (2004): 346-353.
Harlow, E. & Lane, D. "Using Antibodies-A laboratory manual", Cold Spring Harbor Laboratory, (1989).
Holliger, P. et al. Proc Natl Acad Sci, 90 (1993): 6444-6448.
Howard, G. C. & Kaser, M. R. "Making and Using antibodies: A practical handbook", CRC Press (2007).
Jung, G. et al., Proc Natl Acad Sci USA. 84 (1987): 4611-4615.
Kibbe, A. H., Handbook of Pharmaceutical Excipients rd (2000).
Krieg, A. M., Nat.Rev.Drug Discov. 5 (2006): 471-484.
Krolick, K. A. et al., Proc Nat'l Acad Sci 77 (1980): 5419.
Kuball, J. et al., Blood 109 (2007): 2331-2338.
Liddy, N. et al., Nat.Med. 18 (2012): 980-987.
Liu, et al., Proc Natl Acad Sci 84 (1987): 3439-3443
Ljunggren, H. G. et al., J Exp.Med 162 (1985): 1745-1759.
Longenecker, B. M. et al., Ann N.Y.Acad.Sci. 690 (1993): 276-291
Lonsdale, J., Nat.Genet. 45 (2013): 580-585
Lukas, T. J. et al., Proc.Natl.Acad.Sci.U.S.A 78 (1981): 2791-2795
Lundblad, R. L., Chemical Reagents for Protein Modification 3rd (2004)
Meziere, C. et al., J Immunol 159 (1997): 3230-3237.
Mondon R et al Front BioSci 13 (2008): 1117-1129, 1008.
Morgan, R. A. et al., Science 314 (2006): 126-129.
Morrison S. L. et al., Proc Natl Acad Sci (1984): 6851-6855.
Mueller, L. N. et al., J Proteome.Res. 7 (2008): 51-61.
Mueller, L. N. et al., Proteomics. 7 (2007): 3470-3480.
Olexiouk, V. et al., Nucleic Acids Res 44 (2016): D324-D329.
Pinheiro, J. et al., nlme: Linear and Nonlinear Mixed Effects Models (CRAN.R-project.org/packe=nlme) (2015)
Plebanski, M. et al., Eur.J Immunol 25 (1995): 1783-1787.
Porta, C. et al., Virology 202 (1994): 949-955.
Rammensee, H. G. et al., Immunogenetics 50 (1999): 213-219
Rini, B. I. et al., Cancer 107 (2006): 67-74.
Rock, K. L. et al., Science 249 (1990): 918-921.
Rodenko, B. et al., Nat Protoc. 1 (2006): 1120-1132.
Russell, S. J. et al., Nucl Acids Res 21 (1993): 1081-1085.
Saiki, R. K. et al., Science 239 (1988): 487-491
Schmitt, T. M. et al., Hum.Gene Ther. 20 (2009): 1240-1248.
Scholten, K. B. et al., Clin Immunol. 119 (2006): 135-145.
Seeger, F. H. et al., Immunogenetics 49 (1999): 571-576.
Sherman, F. et al., Laboratory Course Manual for Methods in Yeast Genetics (1986).
Silva, L. P. et al., Anal. Chem. 85 (2013): 9536-9542.
Singh-Jasuja, H. et al., Cancer Immunol.Immunother. 53 (2004): 187-195.
Small, E. J. et al., J Clin Oncol. 24 (2006): 3089-3094.
Sternberg, N. et al. Proc Natl Acad Sci 92 (1995): 1609-1613.
Sturm, M. et al., BMC.Bioinformatics. 9 (2008): 163.
Subramanian, R. P. et al., Retrovirology. 8 (2011): 90.
Sun, L. K. et al., Proc Natl Acad Sci 84 (1987): 214-218.
Teufel, R. et al., Cell Mol.Life Sci. 62 (2005): 1755-1762.
Traunecker, A. et al., EMBO 10 (1991): 3655-3659.
Walter, S. et al., J.Immunol. 171 (2003): 4974-4978.
Walter, S. et al., Nat Med. 18 (2012): 1254-1261.
Willcox, B. E. et al., Protein Sci. 8 (1999): 2418-2423.
Youle, R. J. et al., Proc Natl Acad Sci 77 (1980): 5483-5486.
Zaremba, S. et al., Cancer Res. 57 (1997): 4570-4577.
Zufferey, R. et al., J Virol. 73 (1999): 2886-2892.

SEQUENCE LISTING

```
Sequence total quantity: 218
SEQ ID NO: 1          moltype = AA  length = 10
FEATURE               Location/Qualifiers
```

-continued

```
source                    1..10
                          mol_type = protein
                          organism = Homo sapiens
SEQUENCE: 1
AILAPPAILK                                                                    10

SEQ ID NO: 2              moltype = AA   length = 9
FEATURE                   Location/Qualifiers
source                    1..9
                          mol_type = protein
                          organism = Homo sapiens
SEQUENCE: 2
GTVFVLLSK                                                                     9

SEQ ID NO: 3              moltype = AA   length = 9
FEATURE                   Location/Qualifiers
source                    1..9
                          mol_type = protein
                          organism = Homo sapiens
SEQUENCE: 3
VYIASSFKI                                                                     9

SEQ ID NO: 4              moltype = AA   length = 9
FEATURE                   Location/Qualifiers
source                    1..9
                          mol_type = protein
                          organism = Homo sapiens
SEQUENCE: 4
IQAPALLKV                                                                     9

SEQ ID NO: 5              moltype = AA   length = 9
FEATURE                   Location/Qualifiers
source                    1..9
                          mol_type = protein
                          organism = Homo sapiens
SEQUENCE: 5
METADRPEW                                                                     9

SEQ ID NO: 6              moltype = AA   length = 9
FEATURE                   Location/Qualifiers
source                    1..9
                          mol_type = protein
                          organism = Homo sapiens
SEQUENCE: 6
SHSLPAFTL                                                                     9

SEQ ID NO: 7              moltype = AA   length = 11
FEATURE                   Location/Qualifiers
source                    1..11
                          mol_type = protein
                          organism = Homo sapiens
SEQUENCE: 7
IYIPTNSIYK F                                                                  11

SEQ ID NO: 8              moltype = AA   length = 9
FEATURE                   Location/Qualifiers
source                    1..9
                          mol_type = protein
                          organism = Homo sapiens
SEQUENCE: 8
VIYNQTLMK                                                                     9

SEQ ID NO: 9              moltype = AA   length = 9
FEATURE                   Location/Qualifiers
source                    1..9
                          mol_type = protein
                          organism = Homo sapiens
SEQUENCE: 9
LLGVVSHSV                                                                     9

SEQ ID NO: 10             moltype = AA   length = 9
FEATURE                   Location/Qualifiers
source                    1..9
                          mol_type = protein
                          organism = Homo sapiens
SEQUENCE: 10
ILMILQPQL                                                                     9

SEQ ID NO: 11             moltype = AA   length = 10
```

```
FEATURE              Location/Qualifiers
source               1..10
                     mol_type = protein
                     organism = Homo sapiens
SEQUENCE: 11
TEIGTVIKLF                                                              10

SEQ ID NO: 12        moltype = AA  length = 9
FEATURE              Location/Qualifiers
source               1..9
                     mol_type = protein
                     organism = Homo sapiens
SEQUENCE: 12
RLQEGLAAL                                                               9

SEQ ID NO: 13        moltype = AA  length = 9
FEATURE              Location/Qualifiers
source               1..9
                     mol_type = protein
                     organism = Homo sapiens
SEQUENCE: 13
LYDTVTHTF                                                               9

SEQ ID NO: 14        moltype = AA  length = 10
FEATURE              Location/Qualifiers
source               1..10
                     mol_type = protein
                     organism = Homo sapiens
SEQUENCE: 14
ILAPPQRISF                                                              10

SEQ ID NO: 15        moltype = AA  length = 9
FEATURE              Location/Qualifiers
source               1..9
                     mol_type = protein
                     organism = Homo sapiens
SEQUENCE: 15
SPVETRSLL                                                               9

SEQ ID NO: 16        moltype = AA  length = 11
FEATURE              Location/Qualifiers
source               1..11
                     mol_type = protein
                     organism = Homo sapiens
SEQUENCE: 16
NFHTLAQQLL F                                                            11

SEQ ID NO: 17        moltype = AA  length = 9
FEATURE              Location/Qualifiers
source               1..9
                     mol_type = protein
                     organism = Homo sapiens
SEQUENCE: 17
MVNWSLTNK                                                               9

SEQ ID NO: 18        moltype = AA  length = 9
FEATURE              Location/Qualifiers
source               1..9
                     mol_type = protein
                     organism = Homo sapiens
SEQUENCE: 18
SLSKLVATV                                                               9

SEQ ID NO: 19        moltype = AA  length = 10
FEATURE              Location/Qualifiers
source               1..10
                     mol_type = protein
                     organism = Homo sapiens
SEQUENCE: 19
RILEVVRQPK                                                              10

SEQ ID NO: 20        moltype = AA  length = 9
FEATURE              Location/Qualifiers
source               1..9
                     mol_type = protein
                     organism = Homo sapiens
SEQUENCE: 20
ILAPPAILK                                                               9
```

-continued

| | | |
|---|---|---|
| SEQ ID NO: 21<br>FEATURE<br>source | moltype = AA   length = 9<br>Location/Qualifiers<br>1..9<br>mol_type = protein<br>organism = Homo sapiens | |
| SEQUENCE: 21<br>MLSAQFILK | | 9 |
| SEQ ID NO: 22<br>FEATURE<br>source | moltype = AA   length = 10<br>Location/Qualifiers<br>1..10<br>mol_type = protein<br>organism = Homo sapiens | |
| SEQUENCE: 22<br>RVIEVVMNSK | | 10 |
| SEQ ID NO: 23<br>FEATURE<br>source | moltype = AA   length = 9<br>Location/Qualifiers<br>1..9<br>mol_type = protein<br>organism = Homo sapiens | |
| SEQUENCE: 23<br>AETKQFWSA | | 9 |
| SEQ ID NO: 24<br>FEATURE<br>source | moltype = AA   length = 11<br>Location/Qualifiers<br>1..11<br>mol_type = protein<br>organism = Homo sapiens | |
| SEQUENCE: 24<br>LIYIPTNSIY K | | 11 |
| SEQ ID NO: 25<br>FEATURE<br>source | moltype = AA   length = 9<br>Location/Qualifiers<br>1..9<br>mol_type = protein<br>organism = Homo sapiens | |
| SEQUENCE: 25<br>GVCSTLTIK | | 9 |
| SEQ ID NO: 26<br>FEATURE<br>source | moltype = AA   length = 9<br>Location/Qualifiers<br>1..9<br>mol_type = protein<br>organism = Homo sapiens | |
| SEQUENCE: 26<br>ETNTIEFIY | | 9 |
| SEQ ID NO: 27<br>FEATURE<br>source | moltype = AA   length = 9<br>Location/Qualifiers<br>1..9<br>mol_type = protein<br>organism = Homo sapiens | |
| SEQUENCE: 27<br>SQAKQITIW | | 9 |
| SEQ ID NO: 28<br>FEATURE<br>source | moltype = AA   length = 11<br>Location/Qualifiers<br>1..11<br>mol_type = protein<br>organism = Homo sapiens | |
| SEQUENCE: 28<br>ATLQAVTLYK K | | 11 |
| SEQ ID NO: 29<br>FEATURE<br>source | moltype = AA   length = 9<br>Location/Qualifiers<br>1..9<br>mol_type = protein<br>organism = Homo sapiens | |
| SEQUENCE: 29<br>GTFIAPVMK | | 9 |
| SEQ ID NO: 30<br>FEATURE<br>source | moltype = AA   length = 9<br>Location/Qualifiers<br>1..9<br>mol_type = protein<br>organism = Homo sapiens | |
| SEQUENCE: 30<br>SLKSSILFL | | 9 |

```
SEQ ID NO: 31            moltype = AA   length = 10
FEATURE                  Location/Qualifiers
source                   1..10
                         mol_type = protein
                         organism = Homo sapiens SEQUENCE: 31
VFLLLPYPRF                                                                    10

SEQ ID NO: 32            moltype = AA   length = 9
FEATURE                  Location/Qualifiers
source                   1..9
                         mol_type = protein
                         organism = Homo sapiens SEQUENCE: 32
TAMTTLMAF                                                                      9

SEQ ID NO: 33            moltype = AA   length = 9
FEATURE                  Location/Qualifiers
source                   1..9
                         mol_type = protein
                         organism = Homo sapiens SEQUENCE: 33
AYIPFPPLI                                                                      9

SEQ ID NO: 34            moltype = AA   length = 9
FEATURE                  Location/Qualifiers
source                   1..9
                         mol_type = protein
                         organism = Homo sapiens SEQUENCE: 34
LLFKGLMWK                                                                      9

SEQ ID NO: 35            moltype = AA   length = 9
FEATURE                  Location/Qualifiers
source                   1..9
                         mol_type = protein
                         organism = Homo sapiens SEQUENCE: 35
SLATAISAK                                                                      9

SEQ ID NO: 36            moltype = AA   length = 9
FEATURE                  Location/Qualifiers
source                   1..9
                         mol_type = protein
                         organism = Homo sapiens SEQUENCE: 36
KEIEAQEAA                                                                      9

SEQ ID NO: 37            moltype = AA   length = 10
FEATURE                  Location/Qualifiers
source                   1..10
                         mol_type = protein
                         organism = Homo sapiens SEQUENCE: 37
RLYSGSSFLY                                                                    10

SEQ ID NO: 38            moltype = AA   length = 9
FEATURE                  Location/Qualifiers
source                   1..9
                         mol_type = protein
                         organism = Homo sapiens SEQUENCE: 38
AVVSHFILY                                                                      9

SEQ ID NO: 39            moltype = AA   length = 9
FEATURE                  Location/Qualifiers
source                   1..9
                         mol_type = protein
                         organism = Homo sapiens SEQUENCE: 39
RELGVGIAL                                                                      9

SEQ ID NO: 40            moltype = AA   length = 9
FEATURE                  Location/Qualifiers
source                   1..9
                         mol_type = protein
                         organism = Homo sapiens

SEQUENCE: 40
```

-continued

```
LYQTTIELF                                                                    9

SEQ ID NO: 41           moltype = AA  length = 9
FEATURE                 Location/Qualifiers
source                  1..9
                        mol_type = protein
                        organism = Homo sapiens SEQUENCE: 41
APQPRSLAA                                                                    9

SEQ ID NO: 42           moltype = AA  length = 9
FEATURE                 Location/Qualifiers
source                  1..9
                        mol_type = protein
                        organism = Homo sapiens SEQUENCE: 42
LLSRGILIL                                                                    9

SEQ ID NO: 43           moltype = AA  length = 9
FEATURE                 Location/Qualifiers
source                  1..9
                        mol_type = protein
                        organism = Homo sapiens SEQUENCE: 43
VFIPSVINL                                                                    9

SEQ ID NO: 44           moltype = AA  length = 9
FEATURE                 Location/Qualifiers
source                  1..9
                        mol_type = protein
                        organism = Homo sapiens SEQUENCE: 44
SLFPYFLNK                                                                    9

SEQ ID NO: 45           moltype = AA  length = 9
FEATURE                 Location/Qualifiers
source                  1..9
                        mol_type = protein
                        organism = Homo sapiens SEQUENCE: 45
SLFPISLTV                                                                    9

SEQ ID NO: 46           moltype = AA  length = 11
FEATURE                 Location/Qualifiers
source                  1..11
                        mol_type = protein
                        organism = Homo sapiens SEQUENCE: 46
GESIYLLVRK W                                                                11

SEQ ID NO: 47           moltype = AA  length = 9
FEATURE                 Location/Qualifiers
source                  1..9
                        mol_type = protein
                        organism = Homo sapiens SEQUENCE: 47
LYIFTTRPF                                                                    9

SEQ ID NO: 48           moltype = AA  length = 9
FEATURE                 Location/Qualifiers
source                  1..9
                        mol_type = protein
                        organism = Homo sapiens SEQUENCE: 48
TEMSVSALY                                                                    9

SEQ ID NO: 49           moltype = AA  length = 10
FEATURE                 Location/Qualifiers
source                  1..10
                        mol_type = protein
                        organism = Homo sapiens SEQUENCE: 49
IYFHLNNWTI                                                                  10

SEQ ID NO: 50           moltype = AA  length = 9
FEATURE                 Location/Qualifiers
source                  1..9
                        mol_type = protein
                        organism = Homo sapiens
```

```
SEQUENCE: 50
KTIDLVIVR                                                                    9

SEQ ID NO: 51         moltype = AA  length = 11
FEATURE               Location/Qualifiers
source                1..11
                      mol_type = protein
                      organism = Homo sapiens
SEQUENCE: 51
SVFSLVHLFD K                                                                 11

SEQ ID NO: 52         moltype = AA  length = 9
FEATURE               Location/Qualifiers
source                1..9
                      mol_type = protein
                      organism = Homo sapiens
SEQUENCE: 52
SPLPHLGPL                                                                    9

SEQ ID NO: 53         moltype = AA  length = 9
FEATURE               Location/Qualifiers
source                1..9
                      mol_type = protein
                      organism = Homo sapiens
SEQUENCE: 53
TTLENLPQK                                                                    9

SEQ ID NO: 54         moltype = AA  length = 9
FEATURE               Location/Qualifiers
source                1..9
                      mol_type = protein
                      organism = Homo sapiens
SEQUENCE: 54
ASSPVILLL                                                                    9

SEQ ID NO: 55         moltype = AA  length = 9
FEATURE               Location/Qualifiers
source                1..9
                      mol_type = protein
                      organism = Homo sapiens
SEQUENCE: 55
SPVSASWIL                                                                    9

SEQ ID NO: 56         moltype = AA  length = 9
FEATURE               Location/Qualifiers
source                1..9
                      mol_type = protein
                      organism = Homo sapiens
SEQUENCE: 56
DVDIHKDLY                                                                    9

SEQ ID NO: 57         moltype = AA  length = 9
FEATURE               Location/Qualifiers
source                1..9
                      mol_type = protein
                      organism = Homo sapiens
SEQUENCE: 57
IIIDRILLL                                                                    9

SEQ ID NO: 58         moltype = AA  length = 9
FEATURE               Location/Qualifiers
source                1..9
                      mol_type = protein
                      organism = Homo sapiens
SEQUENCE: 58
REQLDGATL                                                                    9

SEQ ID NO: 59         moltype = AA  length = 9
FEATURE               Location/Qualifiers
source                1..9
                      mol_type = protein
                      organism = Homo sapiens
SEQUENCE: 59
AVDLGVLEL                                                                    9

SEQ ID NO: 60         moltype = AA  length = 10
FEATURE               Location/Qualifiers
source                1..10
                      mol_type = protein
```

```
                           organism = Homo sapiens
SEQUENCE: 60
VSPDEVLALW                                                                     10

SEQ ID NO: 61              moltype = AA   length = 9
FEATURE                    Location/Qualifiers
source                     1..9
                           mol_type = protein
                           organism = Homo sapiens
SEQUENCE: 61
GLIAFAIFK                                                                       9

SEQ ID NO: 62              moltype = AA   length = 9
FEATURE                    Location/Qualifiers
source                     1..9
                           mol_type = protein
                           organism = Homo sapiens
SEQUENCE: 62
SFSLLLPYL                                                                       9

SEQ ID NO: 63              moltype = AA   length = 10
FEATURE                    Location/Qualifiers
source                     1..10
                           mol_type = protein
                           organism = Homo sapiens
SEQUENCE: 63
MPANFETIGF                                                                     10

SEQ ID NO: 64              moltype = AA   length = 9
FEATURE                    Location/Qualifiers
source                     1..9
                           mol_type = protein
                           organism = Homo sapiens
SEQUENCE: 64
LPTRSLPAF                                                                       9

SEQ ID NO: 65              moltype = AA   length = 9
FEATURE                    Location/Qualifiers
source                     1..9
                           mol_type = protein
                           organism = Homo sapiens
SEQUENCE: 65
NSDLFYLLL                                                                       9

SEQ ID NO: 66              moltype = AA   length = 8
FEATURE                    Location/Qualifiers
source                     1..8
                           mol_type = protein
                           organism = Homo sapiens
SEQUENCE: 66
RPLILIRI                                                                        8

SEQ ID NO: 67              moltype = AA   length = 9
FEATURE                    Location/Qualifiers
source                     1..9
                           mol_type = protein
                           organism = Homo sapiens
SEQUENCE: 67
GRFWLPFNF                                                                       9

SEQ ID NO: 68              moltype = AA   length = 9
FEATURE                    Location/Qualifiers
source                     1..9
                           mol_type = protein
                           organism = Homo sapiens
SEQUENCE: 68
TVDKGELLY                                                                       9

SEQ ID NO: 69              moltype = AA   length = 9
FEATURE                    Location/Qualifiers
source                     1..9
                           mol_type = protein
                           organism = Homo sapiens
SEQUENCE: 69
KYPTIICGF                                                                       9

SEQ ID NO: 70              moltype = AA   length = 9
FEATURE                    Location/Qualifiers
source                     1..9
```

```
                        mol_type = protein
                        organism = Homo sapiens
SEQUENCE: 70
LIAGLIFLK                                                               9

SEQ ID NO: 71           moltype = AA   length = 9
FEATURE                 Location/Qualifiers
source                  1..9
                        mol_type = protein
                        organism = Homo sapiens
SEQUENCE: 71
LIDSLLLLL                                                               9

SEQ ID NO: 72           moltype = AA   length = 9
FEATURE                 Location/Qualifiers
source                  1..9
                        mol_type = protein
                        organism = Homo sapiens
SEQUENCE: 72
GSCSFALSR                                                               9

SEQ ID NO: 73           moltype = AA   length = 8
FEATURE                 Location/Qualifiers
source                  1..8
                        mol_type = protein
                        organism = Homo sapiens
SEQUENCE: 73
NQKGLISL                                                                8

SEQ ID NO: 74           moltype = AA   length = 8
FEATURE                 Location/Qualifiers
source                  1..8
                        mol_type = protein
                        organism = Homo sapiens
SEQUENCE: 74
TLNVLITL                                                                8

SEQ ID NO: 75           moltype = AA   length = 9
FEATURE                 Location/Qualifiers
source                  1..9
                        mol_type = protein
                        organism = Homo sapiens
SEQUENCE: 75
TTAAVYILK                                                               9

SEQ ID NO: 76           moltype = AA   length = 9
FEATURE                 Location/Qualifiers
source                  1..9
                        mol_type = protein
                        organism = Homo sapiens
SEQUENCE: 76
VQSGVPSRF                                                               9

SEQ ID NO: 77           moltype = AA   length = 9
FEATURE                 Location/Qualifiers
source                  1..9
                        mol_type = protein
                        organism = Homo sapiens
SEQUENCE: 77
YPDVPIGQL                                                               9

SEQ ID NO: 78           moltype = AA   length = 9
FEATURE                 Location/Qualifiers
source                  1..9
                        mol_type = protein
                        organism = Homo sapiens
SEQUENCE: 78
TPSHSTPSF                                                               9

SEQ ID NO: 79           moltype = AA   length = 9
FEATURE                 Location/Qualifiers
source                  1..9
                        mol_type = protein
                        organism = Homo sapiens
SEQUENCE: 79
SLFRLSISF                                                               9

SEQ ID NO: 80           moltype = AA   length = 9
FEATURE                 Location/Qualifiers
```

```
source                      1..9
                            mol_type = protein
                            organism = Homo sapiens
SEQUENCE: 80
IFDLSDPRF                                                                                    9

SEQ ID NO: 81               moltype = AA   length = 10
FEATURE                     Location/Qualifiers
source                      1..10
                            mol_type = protein
                            organism = Homo sapiens
SEQUENCE: 81
KLIAGLIFLK                                                                                  10

SEQ ID NO: 82               moltype = AA   length = 9
FEATURE                     Location/Qualifiers
source                      1..9
                            mol_type = protein
                            organism = Homo sapiens
SEQUENCE: 82
VLQSLQHEL                                                                                    9

SEQ ID NO: 83               moltype = AA   length = 9
FEATURE                     Location/Qualifiers
source                      1..9
                            mol_type = protein
                            organism = Homo sapiens
SEQUENCE: 83
EAAPNIMHY                                                                                    9

SEQ ID NO: 84               moltype = AA   length = 10
FEATURE                     Location/Qualifiers
source                      1..10
                            mol_type = protein
                            organism = Homo sapiens
SEQUENCE: 84
KEFAFLEHSL                                                                                  10

SEQ ID NO: 85               moltype = AA   length = 9
FEATURE                     Location/Qualifiers
source                      1..9
                            mol_type = protein
                            organism = Homo sapiens
SEQUENCE: 85
LPHPVNSGL                                                                                    9

SEQ ID NO: 86               moltype = AA   length = 9
FEATURE                     Location/Qualifiers
source                      1..9
                            mol_type = protein
                            organism = Homo sapiens
SEQUENCE: 86
VANDRLSFL                                                                                    9

SEQ ID NO: 87               moltype = AA   length = 9
FEATURE                     Location/Qualifiers
source                      1..9
                            mol_type = protein
                            organism = Homo sapiens
SEQUENCE: 87
LHLNPGLSF                                                                                    9

SEQ ID NO: 88               moltype = AA   length = 9
FEATURE                     Location/Qualifiers
source                      1..9
                            mol_type = protein
                            organism = Homo sapiens
SEQUENCE: 88
KVGAVVHLK                                                                                    9

SEQ ID NO: 89               moltype = AA   length = 10
FEATURE                     Location/Qualifiers
source                      1..10
                            mol_type = protein
                            organism = Homo sapiens
SEQUENCE: 89
SPSSPLLLLA                                                                                  10

SEQ ID NO: 90               moltype = AA   length = 10
```

```
FEATURE              Location/Qualifiers
source               1..10
                     mol_type = protein
                     organism = Homo sapiens
SEQUENCE: 90
LALLGAPPPK                                                              10

SEQ ID NO: 91        moltype = AA  length = 9
FEATURE              Location/Qualifiers
source               1..9
                     mol_type = protein
                     organism = Homo sapiens
SEQUENCE: 91
RIVTYIVAK                                                                9

SEQ ID NO: 92        moltype = AA  length = 9
FEATURE              Location/Qualifiers
source               1..9
                     mol_type = protein
                     organism = Homo sapiens
SEQUENCE: 92
LNFSDVFLY                                                                9

SEQ ID NO: 93        moltype = AA  length = 9
FEATURE              Location/Qualifiers
source               1..9
                     mol_type = protein
                     organism = Homo sapiens
SEQUENCE: 93
SPIGLSLIL                                                                9

SEQ ID NO: 94        moltype = AA  length = 11
FEATURE              Location/Qualifiers
source               1..11
                     mol_type = protein
                     organism = Homo sapiens
SEQUENCE: 94
AVFLGNPSNQ K                                                            11

SEQ ID NO: 95        moltype = AA  length = 8
FEATURE              Location/Qualifiers
source               1..8
                     mol_type = protein
                     organism = Homo sapiens
SEQUENCE: 95
YAFRNQTL                                                                 8

SEQ ID NO: 96        moltype = AA  length = 12
FEATURE              Location/Qualifiers
source               1..12
                     mol_type = protein
                     organism = Homo sapiens
SEQUENCE: 96
HPRESLNMLV AF                                                           12

SEQ ID NO: 97        moltype = AA  length = 9
FEATURE              Location/Qualifiers
source               1..9
                     mol_type = protein
                     organism = Homo sapiens
SEQUENCE: 97
ALIVLHLSL                                                                9

SEQ ID NO: 98        moltype = AA  length = 9
FEATURE              Location/Qualifiers
source               1..9
                     mol_type = protein
                     organism = Homo sapiens
SEQUENCE: 98
FSEIFQDFL                                                                9

SEQ ID NO: 99        moltype = AA  length = 9
FEATURE              Location/Qualifiers
source               1..9
                     mol_type = protein
                     organism = Homo sapiens
SEQUENCE: 99
RADEEQASF                                                                9
```

```
SEQ ID NO: 100          moltype = AA   length = 12
FEATURE                 Location/Qualifiers
source                  1..12
                        mol_type = protein
                        organism = Homo sapiens
SEQUENCE: 100
SPAPSLARFL SL                                                              12

SEQ ID NO: 101          moltype = AA   length = 9
FEATURE                 Location/Qualifiers
source                  1..9
                        mol_type = protein
                        organism = Homo sapiens
SEQUENCE: 101
ATNSFLLIK                                                                   9

SEQ ID NO: 102          moltype = AA   length = 10
FEATURE                 Location/Qualifiers
source                  1..10
                        mol_type = protein
                        organism = Homo sapiens
SEQUENCE: 102
FLLLEKGGEL                                                                 10

SEQ ID NO: 103          moltype = AA   length = 10
FEATURE                 Location/Qualifiers
source                  1..10
                        mol_type = protein
                        organism = Homo sapiens
SEQUENCE: 103
RPWLSSPTGL                                                                 10

SEQ ID NO: 104          moltype = AA   length = 9
FEATURE                 Location/Qualifiers
source                  1..9
                        mol_type = protein
                        organism = Homo sapiens
SEQUENCE: 104
GSLQTLPPK                                                                   9

SEQ ID NO: 105          moltype = AA   length = 9
FEATURE                 Location/Qualifiers
source                  1..9
                        mol_type = protein
                        organism = Homo sapiens
SEQUENCE: 105
LVFESVVAA                                                                   9

SEQ ID NO: 106          moltype = AA   length = 9
FEATURE                 Location/Qualifiers
source                  1..9
                        mol_type = protein
                        organism = Homo sapiens
SEQUENCE: 106
GLLDAFLRL                                                                   9

SEQ ID NO: 107          moltype = AA   length = 10
FEATURE                 Location/Qualifiers
source                  1..10
                        mol_type = protein
                        organism = Homo sapiens
SEQUENCE: 107
SVISVLTTPK                                                                 10

SEQ ID NO: 108          moltype = AA   length = 9
FEATURE                 Location/Qualifiers
source                  1..9
                        mol_type = protein
                        organism = Homo sapiens
SEQUENCE: 108
SLQESLPNA                                                                   9

SEQ ID NO: 109          moltype = AA   length = 9
FEATURE                 Location/Qualifiers
source                  1..9
                        mol_type = protein
                        organism = Homo sapiens
SEQUENCE: 109
MPKLFLTAC                                                                   9
```

```
SEQ ID NO: 110            moltype = AA   length = 10
FEATURE                   Location/Qualifiers
source                    1..10
                          mol_type = protein
                          organism = Homo sapiens
SEQUENCE: 110
APSLARFLSL                                                                10

SEQ ID NO: 111            moltype = AA   length = 9
FEATURE                   Location/Qualifiers
source                    1..9
                          mol_type = protein
                          organism = Homo sapiens
SEQUENCE: 111
RPIWDVRSA                                                                  9

SEQ ID NO: 112            moltype = AA   length = 9
FEATURE                   Location/Qualifiers
source                    1..9
                          mol_type = protein
                          organism = Homo sapiens
SEQUENCE: 112
ETYGTFVLR                                                                  9

SEQ ID NO: 113            moltype = AA   length = 9
FEATURE                   Location/Qualifiers
source                    1..9
                          mol_type = protein
                          organism = Homo sapiens
SEQUENCE: 113
ALGPMAFRV                                                                  9

SEQ ID NO: 114            moltype = AA   length = 9
FEATURE                   Location/Qualifiers
source                    1..9
                          mol_type = protein
                          organism = Homo sapiens
SEQUENCE: 114
VPHHLLSSV                                                                  9

SEQ ID NO: 115            moltype = AA   length = 9
FEATURE                   Location/Qualifiers
source                    1..9
                          mol_type = protein
                          organism = Homo sapiens
SEQUENCE: 115
LWEEKPVCL                                                                  9

SEQ ID NO: 116            moltype = AA   length = 11
FEATURE                   Location/Qualifiers
source                    1..11
                          mol_type = protein
                          organism = Homo sapiens
SEQUENCE: 116
IYLTKSNLVN M                                                              11

SEQ ID NO: 117            moltype = AA   length = 9
FEATURE                   Location/Qualifiers
source                    1..9
                          mol_type = protein
                          organism = Homo sapiens
SEQUENCE: 117
GEAAAARPV                                                                  9

SEQ ID NO: 118            moltype = AA   length = 9
FEATURE                   Location/Qualifiers
source                    1..9
                          mol_type = protein
                          organism = Homo sapiens
SEQUENCE: 118
RLLRLIPIL                                                                  9

SEQ ID NO: 119            moltype = AA   length = 9
FEATURE                   Location/Qualifiers
source                    1..9
                          mol_type = protein
                          organism = Homo sapiens
SEQUENCE: 119
```

-continued

```
VLHGLLFTL                                                                    9

SEQ ID NO: 120         moltype = AA   length = 9
FEATURE                Location/Qualifiers
source                 1..9
                       mol_type = protein
                       organism = Homo sapiens
SEQUENCE: 120
APGPRSQGL                                                                    9

SEQ ID NO: 121         moltype = AA   length = 9
FEATURE                Location/Qualifiers
source                 1..9
                       mol_type = protein
                       organism = Homo sapiens
SEQUENCE: 121
ILVTAWKGV                                                                    9

SEQ ID NO: 122         moltype = AA   length = 9
FEATURE                Location/Qualifiers
source                 1..9
                       mol_type = protein
                       organism = Homo sapiens
SEQUENCE: 122
FTQKINSTW                                                                    9

SEQ ID NO: 123         moltype = AA   length = 9
FEATURE                Location/Qualifiers
source                 1..9
                       mol_type = protein
                       organism = Homo sapiens
SEQUENCE: 123
TYLESSVRI                                                                    9

SEQ ID NO: 124         moltype = AA   length = 9
FEATURE                Location/Qualifiers
source                 1..9
                       mol_type = protein
                       organism = Homo sapiens
SEQUENCE: 124
SPSSNSREL                                                                    9

SEQ ID NO: 125         moltype = AA   length = 9
FEATURE                Location/Qualifiers
source                 1..9
                       mol_type = protein
                       organism = Homo sapiens
SEQUENCE: 125
ALAQGANLK                                                                    9

SEQ ID NO: 126         moltype = AA   length = 9
FEATURE                Location/Qualifiers
source                 1..9
                       mol_type = protein
                       organism = Homo sapiens
SEQUENCE: 126
NPELLVILL                                                                    9

SEQ ID NO: 127         moltype = AA   length = 10
FEATURE                Location/Qualifiers
source                 1..10
                       mol_type = protein
                       organism = Homo sapiens
SEQUENCE: 127
TVATQVATSK                                                                  10

SEQ ID NO: 128         moltype = AA   length = 9
FEATURE                Location/Qualifiers
source                 1..9
                       mol_type = protein
                       organism = Homo sapiens
SEQUENCE: 128
MTFVPLLAR                                                                    9

SEQ ID NO: 129         moltype = AA   length = 9
FEATURE                Location/Qualifiers
source                 1..9
                       mol_type = protein
                       organism = Homo sapiens
```

```
SEQUENCE: 129
IPISIFKMA                                                                         9

SEQ ID NO: 130          moltype = AA  length = 9
FEATURE                 Location/Qualifiers
source                  1..9
                        mol_type = protein
                        organism = Homo sapiens
SEQUENCE: 130
ITPDSIPSV                                                                         9

SEQ ID NO: 131          moltype = AA  length = 9
FEATURE                 Location/Qualifiers
source                  1..9
                        mol_type = protein
                        organism = Homo sapiens
SEQUENCE: 131
TILAKQNVL                                                                         9

SEQ ID NO: 132          moltype = AA  length = 9
FEATURE                 Location/Qualifiers
source                  1..9
                        mol_type = protein
                        organism = Homo sapiens
SEQUENCE: 132
LYLETRSEF                                                                         9

SEQ ID NO: 133          moltype = AA  length = 9
FEATURE                 Location/Qualifiers
source                  1..9
                        mol_type = protein
                        organism = Homo sapiens
SEQUENCE: 133
KFPPSASEF                                                                         9

SEQ ID NO: 134          moltype = AA  length = 9
FEATURE                 Location/Qualifiers
source                  1..9
                        mol_type = protein
                        organism = Homo sapiens
SEQUENCE: 134
MPCTTILRI                                                                         9

SEQ ID NO: 135          moltype = AA  length = 9
FEATURE                 Location/Qualifiers
source                  1..9
                        mol_type = protein
                        organism = Homo sapiens
SEQUENCE: 135
SADTAELLL                                                                         9

SEQ ID NO: 136          moltype = AA  length = 9
FEATURE                 Location/Qualifiers
source                  1..9
                        mol_type = protein
                        organism = Homo sapiens
SEQUENCE: 136
YSSEIWDLY                                                                         9

SEQ ID NO: 137          moltype = AA  length = 9
FEATURE                 Location/Qualifiers
source                  1..9
                        mol_type = protein
                        organism = Homo sapiens
SEQUENCE: 137
MPIQVLKGL                                                                         9

SEQ ID NO: 138          moltype = AA  length = 10
FEATURE                 Location/Qualifiers
source                  1..10
                        mol_type = protein
                        organism = Homo sapiens
SEQUENCE: 138
RTLPLEGSPK                                                                       10

SEQ ID NO: 139          moltype = AA  length = 9
FEATURE                 Location/Qualifiers
source                  1..9
                        mol_type = protein
```

-continued

```
                          organism = Homo sapiens
SEQUENCE: 139
EEGRIITKW                                                                    9

SEQ ID NO: 140          moltype = AA   length = 8
FEATURE                 Location/Qualifiers
source                  1..8
                        mol_type = protein
                        organism = Homo sapiens
SEQUENCE: 140
QPAPQPLL                                                                     8

SEQ ID NO: 141          moltype = AA   length = 9
FEATURE                 Location/Qualifiers
source                  1..9
                        mol_type = protein
                        organism = Homo sapiens
SEQUENCE: 141
REVAGASAL                                                                    9

SEQ ID NO: 142          moltype = AA   length = 11
FEATURE                 Location/Qualifiers
source                  1..11
                        mol_type = protein
                        organism = Homo sapiens
SEQUENCE: 142
YMLEMDNSMK I                                                                11

SEQ ID NO: 143          moltype = AA   length = 9
FEATURE                 Location/Qualifiers
source                  1..9
                        mol_type = protein
                        organism = Homo sapiens
SEQUENCE: 143
AVLGALLRH                                                                    9

SEQ ID NO: 144          moltype = AA   length = 8
FEATURE                 Location/Qualifiers
source                  1..8
                        mol_type = protein
                        organism = Homo sapiens
SEQUENCE: 144
IIVPSFYK                                                                     8

SEQ ID NO: 145          moltype = AA   length = 9
FEATURE                 Location/Qualifiers
source                  1..9
                        mol_type = protein
                        organism = Homo sapiens
SEQUENCE: 145
HLFSVLSAI                                                                    9

SEQ ID NO: 146          moltype = AA   length = 9
FEATURE                 Location/Qualifiers
source                  1..9
                        mol_type = protein
                        organism = Homo sapiens
SEQUENCE: 146
KVLVDFLLK                                                                    9

SEQ ID NO: 147          moltype = AA   length = 9
FEATURE                 Location/Qualifiers
source                  1..9
                        mol_type = protein
                        organism = Homo sapiens
SEQUENCE: 147
VEAPHLPSF                                                                    9

SEQ ID NO: 148          moltype = AA   length = 9
FEATURE                 Location/Qualifiers
source                  1..9
                        mol_type = protein
                        organism = Homo sapiens
SEQUENCE: 148
SVYMATTLK                                                                    9

SEQ ID NO: 149          moltype = AA   length = 10
FEATURE                 Location/Qualifiers
source                  1..10
```

```
                              mol_type = protein
                              organism = Homo sapiens
SEQUENCE: 149
SMNSKALRWK                                                                10

SEQ ID NO: 150                moltype = AA  length = 10
FEATURE                       Location/Qualifiers
source                        1..10
                              mol_type = protein
                              organism = Homo sapiens
SEQUENCE: 150
IVFLLQQGEK                                                                10

SEQ ID NO: 151                moltype = AA  length = 11
FEATURE                       Location/Qualifiers
source                        1..11
                              mol_type = protein
                              organism = Homo sapiens
SEQUENCE: 151
AVFVNWEQTK K                                                              11

SEQ ID NO: 152                moltype = AA  length = 9
FEATURE                       Location/Qualifiers
source                        1..9
                              mol_type = protein
                              organism = Homo sapiens
SEQUENCE: 152
KIMEILNLK                                                                 9

SEQ ID NO: 153                moltype = AA  length = 9
FEATURE                       Location/Qualifiers
source                        1..9
                              mol_type = protein
                              organism = Homo sapiens
SEQUENCE: 153
ALNLSRLTV                                                                 9

SEQ ID NO: 154                moltype = AA  length = 9
FEATURE                       Location/Qualifiers
source                        1..9
                              mol_type = protein
                              organism = Homo sapiens
SEQUENCE: 154
TVTSAIVNR                                                                 9

SEQ ID NO: 155                moltype = AA  length = 9
FEATURE                       Location/Qualifiers
source                        1..9
                              mol_type = protein
                              organism = Homo sapiens
SEQUENCE: 155
MPWVLMSPF                                                                 9

SEQ ID NO: 156                moltype = AA  length = 9
FEATURE                       Location/Qualifiers
source                        1..9
                              mol_type = protein
                              organism = Homo sapiens
SEQUENCE: 156
SLRVPSPAL                                                                 9

SEQ ID NO: 157                moltype = AA  length = 9
FEATURE                       Location/Qualifiers
source                        1..9
                              mol_type = protein
                              organism = Homo sapiens
SEQUENCE: 157
APLRAGWAA                                                                 9

SEQ ID NO: 158                moltype = AA  length = 9
FEATURE                       Location/Qualifiers
source                        1..9
                              mol_type = protein
                              organism = Homo sapiens
SEQUENCE: 158
FQLSGPVTF                                                                 9

SEQ ID NO: 159                moltype = AA  length = 9
FEATURE                       Location/Qualifiers
```

```
source                  1..9
                        mol_type = protein
                        organism = Homo sapiens
SEQUENCE: 159
ASAIPAGAK                                                                    9

SEQ ID NO: 160          moltype = AA   length = 9
FEATURE                 Location/Qualifiers
source                  1..9
                        mol_type = protein
                        organism = Homo sapiens
SEQUENCE: 160
EYLGSENVF                                                                    9

SEQ ID NO: 161          moltype = AA   length = 9
FEATURE                 Location/Qualifiers
source                  1..9
                        mol_type = protein
                        organism = Homo sapiens
SEQUENCE: 161
ILAASFQAR                                                                    9

SEQ ID NO: 162          moltype = AA   length = 11
FEATURE                 Location/Qualifiers
source                  1..11
                        mol_type = protein
                        organism = Homo sapiens
SEQUENCE: 162
LPVHGPLPLL L                                                                11

SEQ ID NO: 163          moltype = AA   length = 9
FEATURE                 Location/Qualifiers
source                  1..9
                        mol_type = protein
                        organism = Homo sapiens
SEQUENCE: 163
LWALAIPSL                                                                    9

SEQ ID NO: 164          moltype = AA   length = 9
FEATURE                 Location/Qualifiers
source                  1..9
                        mol_type = protein
                        organism = Homo sapiens
SEQUENCE: 164
SHSSPTVSF                                                                    9

SEQ ID NO: 165          moltype = AA   length = 9
FEATURE                 Location/Qualifiers
source                  1..9
                        mol_type = protein
                        organism = Homo sapiens
SEQUENCE: 165
FYNPRPPLI                                                                    9

SEQ ID NO: 166          moltype = AA   length = 9
FEATURE                 Location/Qualifiers
source                  1..9
                        mol_type = protein
                        organism = Homo sapiens
SEQUENCE: 166
VIFLHQPPK                                                                    9

SEQ ID NO: 167          moltype = AA   length = 10
FEATURE                 Location/Qualifiers
source                  1..10
                        mol_type = protein
                        organism = Homo sapiens
SEQUENCE: 167
FALGPIIKQL                                                                  10

SEQ ID NO: 168          moltype = AA   length = 9
FEATURE                 Location/Qualifiers
source                  1..9
                        mol_type = protein
                        organism = Homo sapiens
SEQUENCE: 168
AEGPDHHSL                                                                    9

SEQ ID NO: 169          moltype = AA   length = 9
```

```
FEATURE                 Location/Qualifiers
source                  1..9
                        mol_type = protein
                        organism = Homo sapiens
SEQUENCE: 169
RPQGVGPAA                                                                          9

SEQ ID NO: 170          moltype = AA  length = 9
FEATURE                 Location/Qualifiers
source                  1..9
                        mol_type = protein
                        organism = Homo sapiens
SEQUENCE: 170
LLDSWNILI                                                                          9

SEQ ID NO: 171          moltype = AA  length = 10
FEATURE                 Location/Qualifiers
source                  1..10
                        mol_type = protein
                        organism = Homo sapiens
SEQUENCE: 171
NVSFEVSLLY                                                                        10

SEQ ID NO: 172          moltype = AA  length = 9
FEATURE                 Location/Qualifiers
source                  1..9
                        mol_type = protein
                        organism = Homo sapiens
SEQUENCE: 172
LLYKTLIIL                                                                          9

SEQ ID NO: 173          moltype = AA  length = 9
FEATURE                 Location/Qualifiers
source                  1..9
                        mol_type = protein
                        organism = Homo sapiens
SEQUENCE: 173
IFTGRNAYF                                                                          9

SEQ ID NO: 174          moltype = AA  length = 9
FEATURE                 Location/Qualifiers
source                  1..9
                        mol_type = protein
                        organism = Homo sapiens
SEQUENCE: 174
LSGPVTFLR                                                                          9

SEQ ID NO: 175          moltype = AA  length = 9
FEATURE                 Location/Qualifiers
source                  1..9
                        mol_type = protein
                        organism = Homo sapiens
SEQUENCE: 175
MPFLKVPPL                                                                          9

SEQ ID NO: 176          moltype = AA  length = 9
FEATURE                 Location/Qualifiers
source                  1..9
                        mol_type = protein
                        organism = Homo sapiens
SEQUENCE: 176
AFLLSLISL                                                                          9

SEQ ID NO: 177          moltype = AA  length = 9
FEATURE                 Location/Qualifiers
source                  1..9
                        mol_type = protein
                        organism = Homo sapiens
SEQUENCE: 177
SYLKDHLSL                                                                          9

SEQ ID NO: 178          moltype = AA  length = 9
FEATURE                 Location/Qualifiers
source                  1..9
                        mol_type = protein
                        organism = Homo sapiens
SEQUENCE: 178
SLFGGLFTR                                                                          9
```

```
SEQ ID NO: 179          moltype = AA  length = 9
FEATURE                 Location/Qualifiers
source                  1..9
                        mol_type = protein
                        organism = Homo sapiens
SEQUENCE: 179
MIFSGVFLR                                                                 9

SEQ ID NO: 180          moltype = AA  length = 9
FEATURE                 Location/Qualifiers
source                  1..9
                        mol_type = protein
                        organism = Homo sapiens
SEQUENCE: 180
QYLTYYPSF                                                                 9

SEQ ID NO: 181          moltype = AA  length = 9
FEATURE                 Location/Qualifiers
source                  1..9
                        mol_type = protein
                        organism = Homo sapiens
SEQUENCE: 181
FDLNIGSAY                                                                 9

SEQ ID NO: 182          moltype = AA  length = 9
FEATURE                 Location/Qualifiers
source                  1..9
                        mol_type = protein
                        organism = Homo sapiens
SEQUENCE: 182
RPSLPCRSF                                                                 9

SEQ ID NO: 183          moltype = AA  length = 10
FEATURE                 Location/Qualifiers
source                  1..10
                        mol_type = protein
                        organism = Homo sapiens
SEQUENCE: 183
VFVISGSHLF                                                               10

SEQ ID NO: 184          moltype = AA  length = 9
FEATURE                 Location/Qualifiers
source                  1..9
                        mol_type = protein
                        organism = Homo sapiens
SEQUENCE: 184
VVHGGMSIF                                                                 9

SEQ ID NO: 185          moltype = AA  length = 11
FEATURE                 Location/Qualifiers
source                  1..11
                        mol_type = protein
                        organism = Homo sapiens
SEQUENCE: 185
MPAFLSRASA L                                                             11

SEQ ID NO: 186          moltype = AA  length = 9
FEATURE                 Location/Qualifiers
source                  1..9
                        mol_type = protein
                        organism = Homo sapiens
SEQUENCE: 186
SQIKSPVVF                                                                 9

SEQ ID NO: 187          moltype = AA  length = 10
FEATURE                 Location/Qualifiers
source                  1..10
                        mol_type = protein
                        organism = Homo sapiens
SEQUENCE: 187
RLCPAAPTGK                                                               10

SEQ ID NO: 188          moltype = AA  length = 9
FEATURE                 Location/Qualifiers
source                  1..9
                        mol_type = protein
                        organism = Homo sapiens
SEQUENCE: 188
KLPFFTNFL                                                                 9
```

```
SEQ ID NO: 189          moltype = AA   length = 9
FEATURE                 Location/Qualifiers
source                  1..9
                        mol_type = protein
                        organism = Homo sapiens SEQUENCE: 189
IWRALGSLF                                                               9

SEQ ID NO: 190          moltype = AA   length = 10
FEATURE                 Location/Qualifiers
source                  1..10
                        mol_type = protein
                        organism = Homo sapiens SEQUENCE: 190
STQSSLLYLK                                                              10

SEQ ID NO: 191          moltype = AA   length = 9
FEATURE                 Location/Qualifiers
source                  1..9
                        mol_type = protein
                        organism = Homo sapiens SEQUENCE: 191
APLLPGPAA                                                               9

SEQ ID NO: 192          moltype = AA   length = 9
FEATURE                 Location/Qualifiers
source                  1..9
                        mol_type = protein
                        organism = Homo sapiens SEQUENCE: 192
IPLHFSTAF                                                               9

SEQ ID NO: 193          moltype = AA   length = 9
FEATURE                 Location/Qualifiers
source                  1..9
                        mol_type = protein
                        organism = Homo sapiens SEQUENCE: 193
ILQLITVNR                                                               9

SEQ ID NO: 194          moltype = AA   length = 9
FEATURE                 Location/Qualifiers
source                  1..9
                        mol_type = protein
                        organism = Homo sapiens SEQUENCE: 194
VLYPSHSSF                                                               9

SEQ ID NO: 195          moltype = AA   length = 10
FEATURE                 Location/Qualifiers
source                  1..10
                        mol_type = protein
                        organism = Homo sapiens SEQUENCE: 195
AWNESSAWLL                                                              10

SEQ ID NO: 196          moltype = AA   length = 8
FEATURE                 Location/Qualifiers
source                  1..8
                        mol_type = protein
                        organism = Homo sapiens SEQUENCE: 196
NSENLLVY                                                                8

SEQ ID NO: 197          moltype = AA   length = 9
FEATURE                 Location/Qualifiers
source                  1..9
                        mol_type = protein
                        organism = Homo sapiens SEQUENCE: 197
HHTQLVFVF                                                               9

SEQ ID NO: 198          moltype = AA   length = 10
FEATURE                 Location/Qualifiers
source                  1..10
                        mol_type = protein
                        organism = Homo sapiens

SEQUENCE: 198
```

```
MTYQQPFSNR                                                                      10

SEQ ID NO: 199          moltype = AA  length = 9
FEATURE                 Location/Qualifiers
source                  1..9
                        mol_type = protein
                        organism = Homo sapiens SEQUENCE: 199
RAPLPLLLL                                                                        9

SEQ ID NO: 200          moltype = AA  length = 9
FEATURE                 Location/Qualifiers
source                  1..9
                        mol_type = protein
                        organism = Homo sapiens SEQUENCE: 200
GLLGTLRVL                                                                        9

SEQ ID NO: 201          moltype = AA  length = 11
FEATURE                 Location/Qualifiers
source                  1..11
                        mol_type = protein
                        organism = Homo sapiens SEQUENCE: 201
VWILQKVNLA F                                                                    11

SEQ ID NO: 202          moltype = AA  length = 9
FEATURE                 Location/Qualifiers
source                  1..9
                        mol_type = protein
                        organism = Homo sapiens SEQUENCE: 202
KLLLLSSVK                                                                        9

SEQ ID NO: 203          moltype = AA  length = 9
FEATURE                 Location/Qualifiers
source                  1..9
                        mol_type = protein
                        organism = Homo sapiens SEQUENCE: 203
AILVPQPPK                                                                        9

SEQ ID NO: 204          moltype = AA  length = 9
FEATURE                 Location/Qualifiers
source                  1..9
                        mol_type = protein
                        organism = Homo sapiens SEQUENCE: 204
VVRASSGLK                                                                        9

SEQ ID NO: 205          moltype = AA  length = 10
FEATURE                 Location/Qualifiers
source                  1..10
                        mol_type = protein
                        organism = Homo sapiens SEQUENCE: 205
SLIPIVPFKS                                                                      10

SEQ ID NO: 206          moltype = AA  length = 10
FEATURE                 Location/Qualifiers
source                  1..10
                        mol_type = protein
                        organism = Homo sapiens SEQUENCE: 206
VEGVHFVQLL                                                                      10

SEQ ID NO: 207          moltype = AA  length = 8
FEATURE                 Location/Qualifiers
source                  1..8
                        mol_type = protein
                        organism = Homo sapiens SEQUENCE: 207
LPALLRSL                                                                         8

SEQ ID NO: 208          moltype = AA  length = 9
FEATURE                 Location/Qualifiers
source                  1..9
                        mol_type = protein
                        organism = Homo sapiens
```

```
SEQUENCE: 208
YVGPTRLEL                                                                    9

SEQ ID NO: 209         moltype = AA  length = 9
FEATURE                Location/Qualifiers
source                 1..9
                       mol_type = protein
                       organism = Homo sapiens
SEQUENCE: 209
AILLPQLPK                                                                    9

SEQ ID NO: 210         moltype = AA  length = 9
FEATURE                Location/Qualifiers
source                 1..9
                       mol_type = protein
                       organism = Homo sapiens
SEQUENCE: 210
ASRIQVILL                                                                    9

SEQ ID NO: 211         moltype = AA  length = 10
FEATURE                Location/Qualifiers
source                 1..10
                       mol_type = protein
                       organism = Homo sapiens
SEQUENCE: 211
VVTIVMHIYK                                                                  10

SEQ ID NO: 212         moltype = AA  length = 9
FEATURE                Location/Qualifiers
source                 1..9
                       mol_type = protein
                       organism = Homo sapiens
SEQUENCE: 212
WETRLHNLW                                                                    9

SEQ ID NO: 213         moltype = AA  length = 11
FEATURE                Location/Qualifiers
source                 1..11
                       mol_type = protein
                       organism = Homo sapiens
SEQUENCE: 213
TLLSFKTVLF K                                                                11

SEQ ID NO: 214         moltype = AA  length = 10
FEATURE                Location/Qualifiers
source                 1..10
                       mol_type = protein
                       organism = Homo sapiens
SEQUENCE: 214
RPSPVRVAAL                                                                  10

SEQ ID NO: 215         moltype = AA  length = 8
FEATURE                Location/Qualifiers
source                 1..8
                       mol_type = protein
                       organism = Homo sapiens
SEQUENCE: 215
TPLTRTTL                                                                     8

SEQ ID NO: 216         moltype = AA  length = 9
FEATURE                Location/Qualifiers
source                 1..9
                       mol_type = protein
                       organism = Homo sapiens
SEQUENCE: 216
ILRTVLPSL                                                                    9

SEQ ID NO: 217         moltype = AA  length = 10
FEATURE                Location/Qualifiers
source                 1..10
                       mol_type = protein
                       organism = Homo sapiens
SEQUENCE: 217
ELAGIGILTV                                                                  10
```

```
SEQ ID NO: 218        moltype = AA  length = 9
FEATURE               Location/Qualifiers
source                1..9
                      mol_type = protein
                      organism = Homo sapiens
SEQUENCE: 218
YLLPAIVHI                                                                    9
```

What is claimed is:

1. A peptide consisting of the amino acid sequence VYIASSFKI (SEQ ID NO: 3) in the form of a pharmaceutically acceptable salt.

2. The peptide of claim 1, wherein the pharmaceutically acceptable salt is chloride salt.

3. The peptide of claim 1, wherein the pharmaceutically acceptable salt is acetate salt.

4. A composition comprising the peptide of claim 1 and a pharmaceutically acceptable carrier.

5. The composition of claim 4, wherein the peptide is in the form of a chloride salt.

6. The composition of claim 4, wherein the peptide is in the form of an acetate salt.

7. The composition of claim 4, further comprising an adjuvant selected from the group consisting of anti-CD40 antibody, imiquimod, resiquimod, cyclophosphamide, sunitinib, bevacizumab, interferon-alpha, interferon-beta, CpG oligonucleotides and derivatives, poly-(I:C) and derivatives, RNA, sildenafil, particulate formulations with poly (lactide co-glycolide) (PLG), virosomes, and cytokines comprising Eotaxin, granulocyte colony-stimulating factor (G-CSF), granulocyte-macrophage colony-stimulating factor (GM-CSF), interferon (INF)-γ, interleukin (IL)-1α, macrophage colony-stimulating factor (M-CSF), IL-1β, IL-2, IL-3, IL-4, IL-5, IL-6, IL-7, IL-10, IL-12p40, IL-13, IL-18, IL-15, IL-17, interferon γ-induced protein 10 kDa (IP-10), macrophage inflammatory protein (MIP)-2, keratinocyte chemoattractant (KC), leukemia inhibitory factor (LIF), lipopolysaccharide-induced CXC chemokine (LIX), monocyte chemoattractant protein-1 (MCP-1), MIP-1α, MIP-1β, monokine induced by gamma (MIG), RANTES, tumor necrosis factor (TNF)-α, IL-12p70, vascular endothelial growth factor (VEGF), IL-9, and IL-21.

8. The composition of claim 7, wherein the adjuvant is IL-2.

9. The composition of claim 7, wherein the adjuvant is IL-15.

10. A pegylated peptide consisting of the amino acid sequence of VYIASSFKI (SEQ ID NO: 3) or a pharmaceutically acceptable salt thereof modified with PEG.

11. The pegylated peptide of claim 10, wherein the pharmaceutically acceptable salt is chloride salt.

12. The pegylated peptide of claim 10, wherein the pharmaceutically acceptable salt is acetate salt.

13. A peptide consisting of the amino acid sequence VYIASSFKI (SEQ ID NO: 3) in the form of a salt.

14. A method of treating a patient who has cancer, comprising administering to said patient a population of activated T cells that kill cancer cells that present a peptide consisting of the amino acid sequence of VYIASSFKI (SEQ ID NO: 3), wherein the cancer is selected from the group consisting of acute myeloid leukemia, breast cancer, cholangiocellular carcinoma, chronic lymphocytic leukemia, colorectal cancer, gallbladder cancer, glioblastoma, gastric cancer, gastro-esophageal junction cancer, hepatocellular carcinoma, head and neck squamous cell carcinoma, melanoma, non-Hodgkin lymphoma, non-small cell lung cancer, ovarian cancer, esophageal cancer, pancreatic cancer, prostate cancer, renal cell carcinoma, small cell lung cancer, urinary bladder carcinoma, and uterine endometrial cancer.

15. The method of claim 14, wherein the T cells are transduced with a T cell receptor (TCR) that binds the peptide in a complex with an MHC class I molecule on the surface of the cancer cells.

16. The method of claim 14, wherein the cancer is hepatocellular carcinoma.

17. The method of claim 14, wherein the cancer is non-small cell lung cancer.

18. The method of claim 14, further comprising administering to said patient an adjuvant selected from the group consisting of anti-CD40 antibody, imiquimod, resiquimod, cyclophosphamide, sunitinib, bevacizumab, interferon-alpha, interferon-beta, CpG oligonucleotides and derivatives, poly-(I:C) and derivatives, RNA, sildenafil, particulate formulations with poly (lactide co-glycolide) (PLG), virosomes, and cytokines comprising Eotaxin, granulocyte colony-stimulating factor (G-CSF), granulocyte-macrophage colony-stimulating factor (GM-CSF), interferon (INF)-γ, interleukin (IL)-1α, macrophage colony-stimulating factor (M-CSF), IL-1β, IL-2, IL-3, IL-4, IL-5, IL-6, IL-7, IL-10, IL-12p40, IL-13, IL-18, IL-15, IL-17, interferon γ-induced protein 10 kDa (IP-10), macrophage inflammatory protein (MIP)-2, keratinocyte chemoattractant (KC), leukemia inhibitory factor (LIF), lipopolysaccharide-induced CXC chemokine (LIX), monocyte chemoattractant protein-1 (MCP-1), MIP-1α, MIP-1β, monokine induced by gamma (MIG), RANTES, tumor necrosis factor (TNF)-α, IL-12p70, vascular endothelial growth factor (VEGF), IL-9, and IL-21.

19. The method of claim 18, wherein the adjuvant is IL-2.

20. The method of claim 18, wherein the adjuvant is IL-15.

* * * * *